(12) United States Patent
Whitehead et al.

(10) Patent No.: US 10,842,791 B2
(45) Date of Patent: Nov. 24, 2020

(54) SMALL MOLECULE INHIBITORS OF EGFR AND PI3K

(71) Applicant: The Regents of the University of Michigan, Ann Arbor, MI (US)

(72) Inventors: Christopher Emil Whitehead, Ann Arbor, MI (US); Judith S. Leopold, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/207,998

(22) Filed: Dec. 3, 2018

(65) Prior Publication Data

US 2019/0167686 A1 Jun. 6, 2019

Related U.S. Application Data

(62) Division of application No. 15/536,528, filed as application No. PCT/US2015/065827 on Dec. 15, 2015, now Pat. No. 10,206,924.

(60) Provisional application No. 62/091,969, filed on Dec. 14, 2014.

(51) Int. Cl.
| | |
|---|---|
| *A61K 45/06* | (2006.01) |
| *A61P 35/04* | (2006.01) |
| *A61K 31/517* | (2006.01) |
| *C07D 401/04* | (2006.01) |
| *C07D 401/14* | (2006.01) |
| *C07D 403/04* | (2006.01) |
| *C07D 403/14* | (2006.01) |
| *C07D 413/14* | (2006.01) |
| *C07D 471/04* | (2006.01) |
| *A61K 31/4706* | (2006.01) |
| *A61K 31/4709* | (2006.01) |
| *A61K 31/5377* | (2006.01) |

(52) U.S. Cl.
CPC ........ *A61K 31/517* (2013.01); *A61K 31/4706* (2013.01); *A61K 31/4709* (2013.01); *A61K 31/5377* (2013.01); *A61K 45/06* (2013.01); *A61P 35/04* (2018.01); *C07D 401/04* (2013.01); *C07D 401/14* (2013.01); *C07D 403/04* (2013.01); *C07D 403/14* (2013.01); *C07D 413/14* (2013.01); *C07D 471/04* (2013.01)

(58) Field of Classification Search
CPC ............ A61K 31/4706; A61K 31/4709; A61K 31/5377; A61K 31/517; A61P 35/04; C07D 471/04; C07D 403/14; C07D 403/04; C07D 401/04; C07D 401/14
See application file for complete search history.

(56) References Cited

U.S. PATENT DOCUMENTS

| | | | |
|---|---|---|---|
| 5,866,572 A | 2/1999 | Barker et al. | |
| 6,002,008 A | 12/1999 | Wissner et al. | |
| 6,225,318 B1 | 5/2001 | Sobolov-Jaynes et al. | |
| 6,689,772 B1 * | 2/2004 | Boschelli ............ | C07D 215/54 514/183 |
| 6,897,214 B2 | 5/2005 | Barker | |
| 2002/0026052 A1 | 2/2002 | Boschelli et al. | |
| 2009/0069320 A1 | 3/2009 | Reich et al. | |
| 2009/0258882 A1 | 10/2009 | Stauffer | |
| 2010/0035919 A1 | 2/2010 | Vasudevan | |
| 2010/0179144 A1 | 7/2010 | Adams | |
| 2012/0238587 A1 | 9/2012 | Lee | |
| 2012/0245350 A1 | 9/2012 | Fontana | |
| 2013/0053341 A1 | 2/2013 | Suzuki et al. | |
| 2013/0165458 A1 | 6/2013 | Huang et al. | |
| 2013/0210819 A1 | 8/2013 | Klein | |
| 2013/0217671 A1 | 8/2013 | Matsuo et al. | |
| 2013/0331405 A1 | 12/2013 | Korkola et al. | |
| 2014/0315886 A1 | 10/2014 | Suzuki et al. | |

FOREIGN PATENT DOCUMENTS

| | | |
|---|---|---|
| EP | 1029853 | 8/2000 |
| EP | 1990337 | 11/2008 |
| EP | 2060565 | 5/2009 |
| EP | 2551270 | 1/2013 |
| EP | 2740729 | 6/2014 |
| JP | 2000-504713 | 4/2000 |
| JP | 2003-528857 | 9/2003 |
| WO | 97/30034 | 8/1997 |
| WO | 1998/002434 | 1/1998 |
| WO | 1999/009016 | 2/1999 |
| WO | 99/35146 | 7/1999 |
| WO | 2001/072711 | 10/2001 |
| WO | 2003082867 | 10/2003 |
| WO | 2006/071017 | 7/2006 |
| WO | 2007/013950 | 2/2007 |

(Continued)

OTHER PUBLICATIONS

Apsel et al. "Targeted polypharmacology: discovery of dual inhibitors of tyrosine and phosphoinositide kinases." Nat Chem Biol. 2008;4: 691-699.

(Continued)

*Primary Examiner* — Shirley V Gembeh

(74) *Attorney, Agent, or Firm* — Casimir Jones, SC; Robert A. Goetz

(57) ABSTRACT

This invention is in the field of medicinal chemistry. In particular, the invention relates to a new class of small-molecules having a quinazoline structure or a quinoline structure which function as dual inhibitors of EGFR proteins and PI3K proteins, and their use as therapeutics for the treatment of cancer and other diseases.

12 Claims, 24 Drawing Sheets

(56) References Cited

FOREIGN PATENT DOCUMENTS

| WO | 2007/059257 | 5/2007 |
| WO | 2008012326 | 1/2008 |
| WO | 2008157191 | 12/2008 |
| WO | 2009155527 | 12/2009 |
| WO | 2013141586 | 9/2013 |

OTHER PUBLICATIONS

Apsel, B. "Dual-specificity inhibitors of lipid and protein kinases" University of California, San Francisco, ProQuest Dissertations Publishing, 2008. 3311357.

Atreya CE, et al. "PTEN expression is consistent in colorectal cancer primaries and metastases and associates with patient survival." Cancer Med. 2013;2: 496-506.

Bethune G, et al., "Epidermal growth factor receptor (EGFR) in lung cancer: an overview and update" J Thorac Dis. 2010;2(1): 48-51.

Buck E, et al., "Rapamycin synergizes with the epidermal growth factor receptor inhibitor erlotinib in non-small-cell lung, pancreatic, colon, and breast tumors." Mol Cancer Ther. 2006;5: 2676-2684.

Cheng et al. "Discovery of the Highly Potent PI3K/mTOR Dual Inhibitor PF-04979064 through Structure-Based Drug Design." ACS Med Chem Lett. 2013;4: 91-97.

Eichhorn PJ, et al., "Phosphatidylinositol 3-kinase hyperactivation results in lapatinib resistance that is reversed by the mTOR/ phosphatidylinositol 3-kinase inhibitor NVP-BEZ235." Cancer Res. 2008;68: 9221-9230.

Fan QW, et al., "A dual phosphoinositide-3-kinase alpha/mTOR inhibitor cooperates with blockade of epidermal growth factor receptor in PTEN-mutant glioma." Cancer Res. 2007;67: 7960-7965.

Gadgeel SM, et al., "Preclinical Rationale for PI3K/Akt/mTOR Pathway Inhibitors as Therapy for Epidermal Growth Factor Receptor Inhibitor-Resistant Non-Small-Cell Lung Cancer" Clin Lung Cancer. 2013;14: 322-332.

Hamada K, et al., "The PTEN/PI3K pathway governs normal vascular development and tumor angiogenesis" 2005 Genes Dev 19 (17): 2054-65.

Heimberger AB, et al., "The natural history of EGFR and EGFRvIII in glioblastoma patients" J Transl Med. 2005;3: 38.

International Search Report and Written Opinion, International Application No. PCT/US2015/065827, dated May 2, 2016.

Jin G, et al.,"PTEN mutations and relationship to EGFR, ERBB2, KRAS, and TP53 mutations in non-small cell lung cancers" Lung Cancer. 2010;69: 279-283.

Knight et al. Discovery of GSK2126458, a Highly Potent Inhibitor of PI3K and the Mammalian Target of Rapamycin. ACS Med Chem Lett. 2010;1: 39-43.

Lui VW, et al., "Frequent mutation of the PI3K pathway in head and neck cancer defines predictive biomarkers." Cancer Discov. 2013;3: 761-769.

Nishimura et al. "Phospshoinositide 3-kinase (PI3K)/mammalian target of rapamycin (mTOR) dual inhibitors: discovery and structure-activity relationships of a series of quinoline and quinoxaline derivatives." J Med Chem. 2011;54: 4735-4751.

Psyrri A, et al., "Molecular Pathways in Head and Neck Cancer: EGFR, PI3K, and More" Am Soc Clin Oncol Educ Book. 2013: 246-255.

Ratushny V, et al., "Targeting EGFR resistance networks in Head and Neck Cancer" Cell Signal. 2009;21: 1255-1268.

Sawai H, et al., "Loss of PTEN expression is associated with colorectal cancer liver metastasis and poor patient survival" BMC Gastroenterol. 2008;8: 56.

Spano JP, et al., "Epidermal growth factor receptor signaling in colorectal cancer: preclinical data and therapeutic perspectives" Ann Oncol. 2005;16: 189-194.

Stamos et al. "Structure of the epidermal growth factor receptor kinase domain alone and in complex with a 4-anilinoquinazoline inhibitor." J Biol Chem. 2002;277(48): 46265-46272.

Yun CH, et al. "The T790M mutation in EGFR kinase causes drug resistance by increasing the affinity for ATP." Proc Natl Acad Sci U S A. 2008;105: 2070-2075.

European Search Report, EP Patent Application No. 15870877.6, dated May 3, 2018, 6 pages.

ptcl.chem.ox.ac.uk/MSDS structure activity relationship; Jaworska, 1-8, 2004.

Cecil Text book of Medicine, 20th Edition vol. 1 W.B. Saunders Company, 1997, pp. 1004-1010.

Barrios Sosa, Ana C. et al. "Further studies on ethenyl and ethynyl-4-phenylamino-3-quinolinecarbonitriles: identification of a subnanomolar Src kinase inhibitor" Bioorg. Med. Chem. Letter. 2005, v. 15, pp. 1743-1747.

Boschelli, D. et al_ "Optimization of 7-alkene-3-quinolinecarbonitriles as Src kinase inhibitors" Bioorg. Med. Chem. Lett. 2010, v. 20, pp. 2924-2927.

* cited by examiner

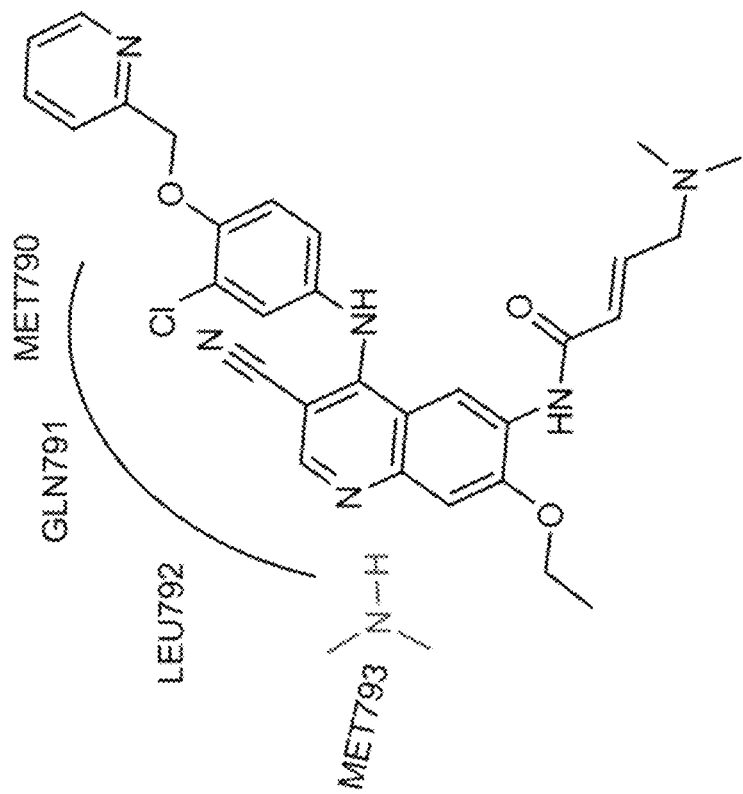
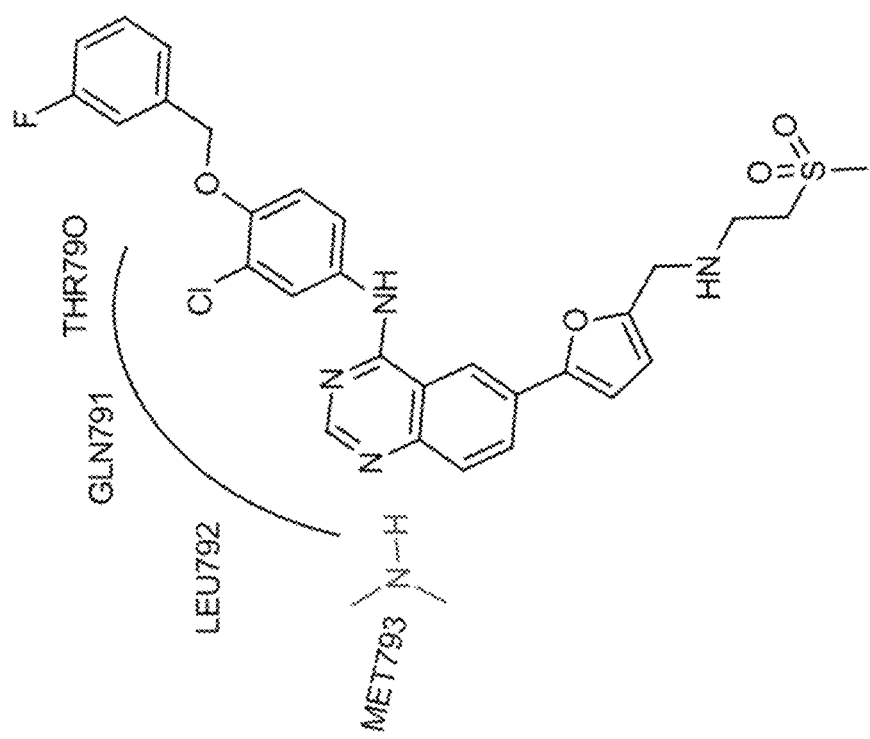
FIG. 3

FIG. 5A
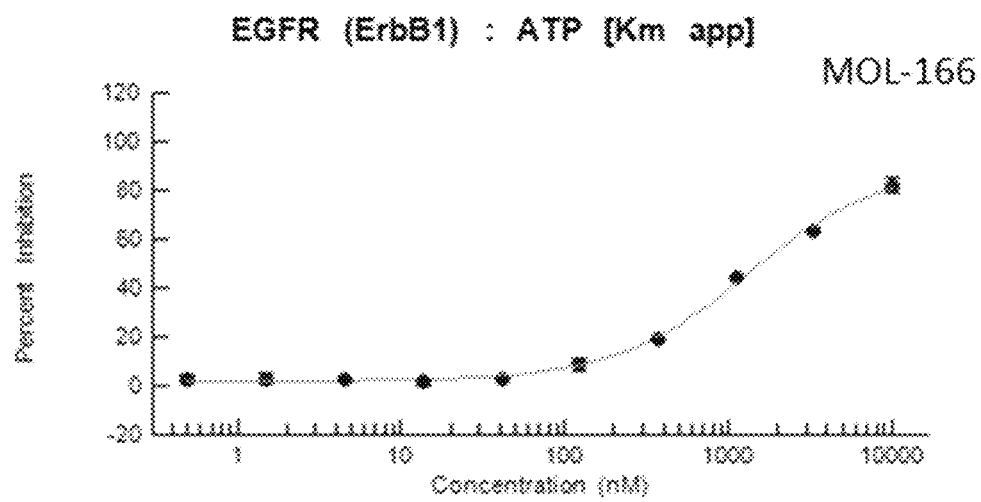
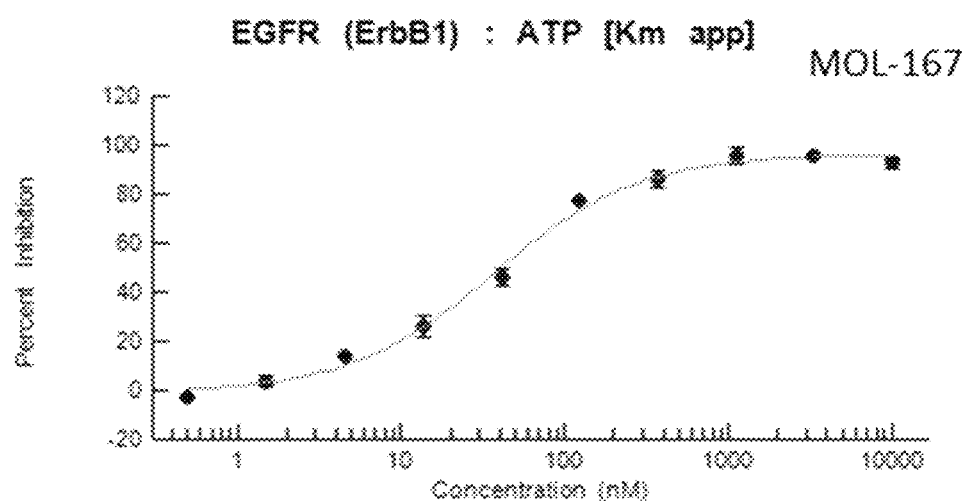
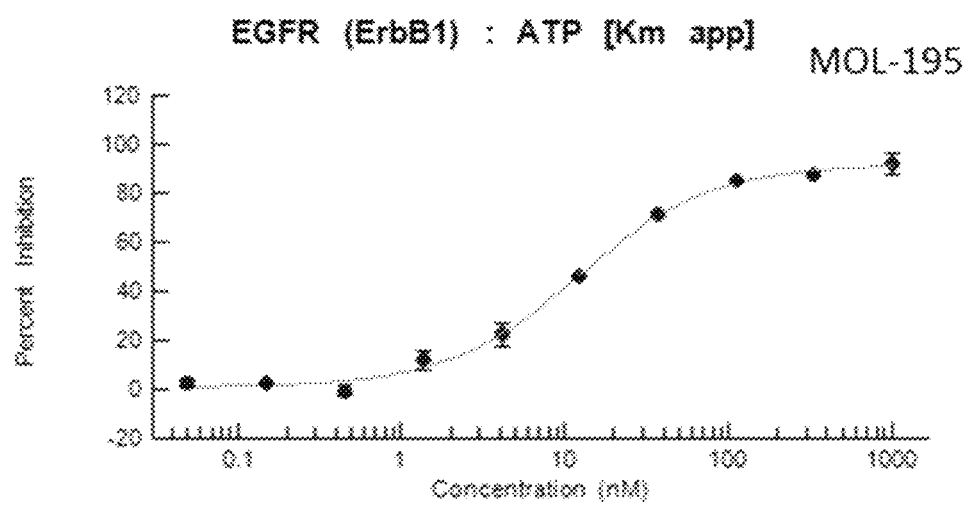

FIG. 5A (CONT'D)
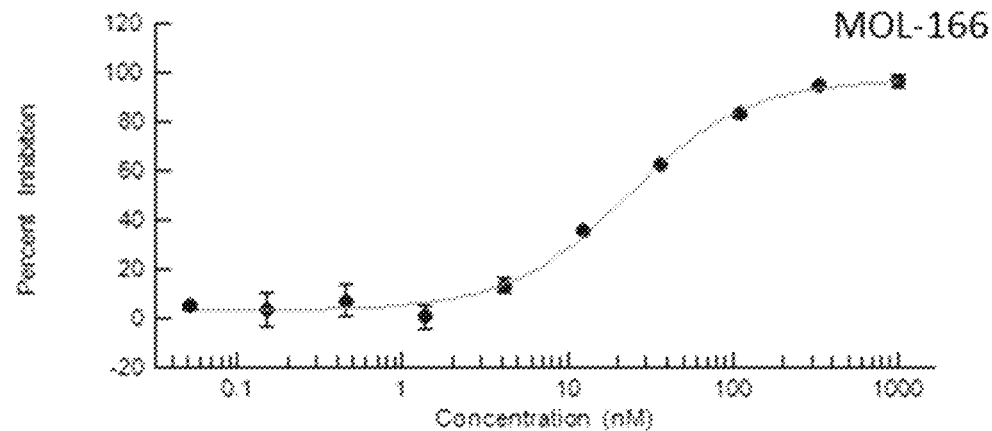
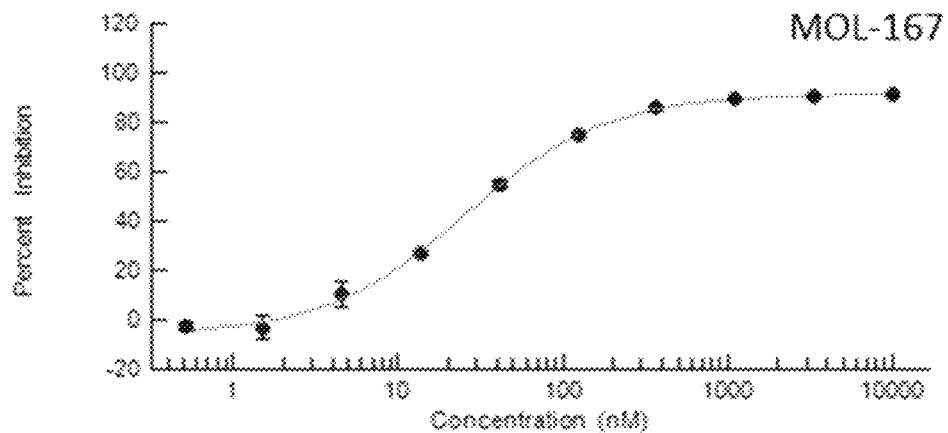
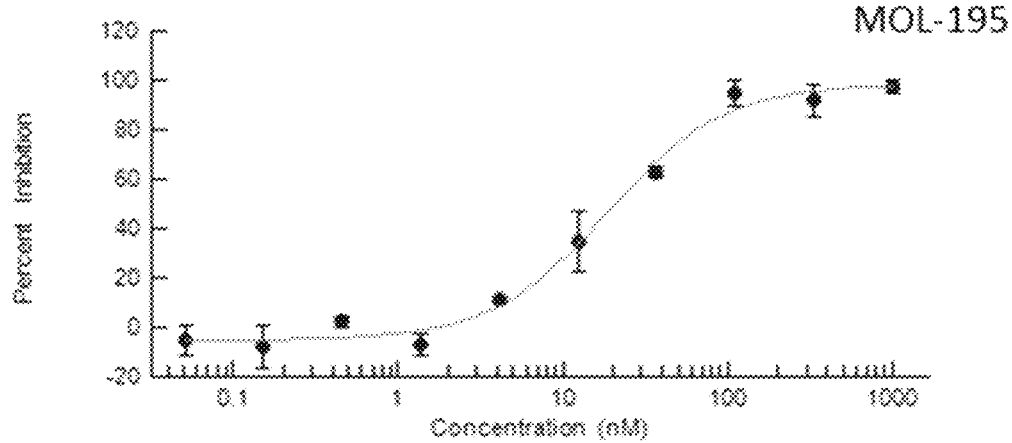

FIG. 5B
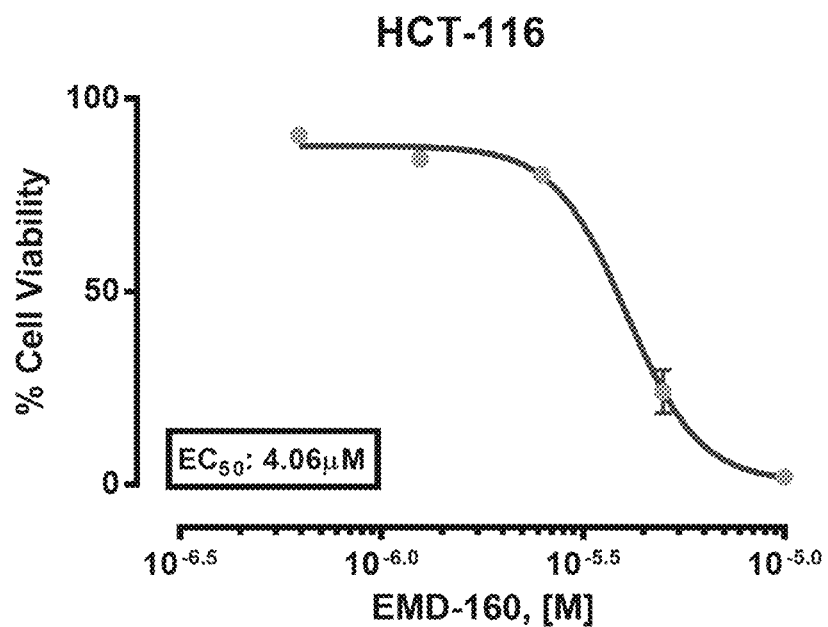
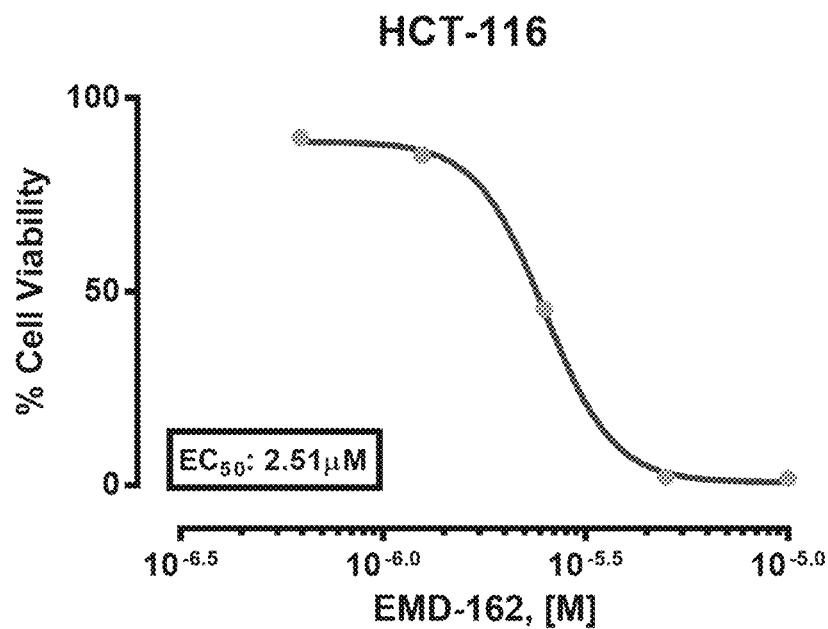

FIG. 5B (CONT'D)
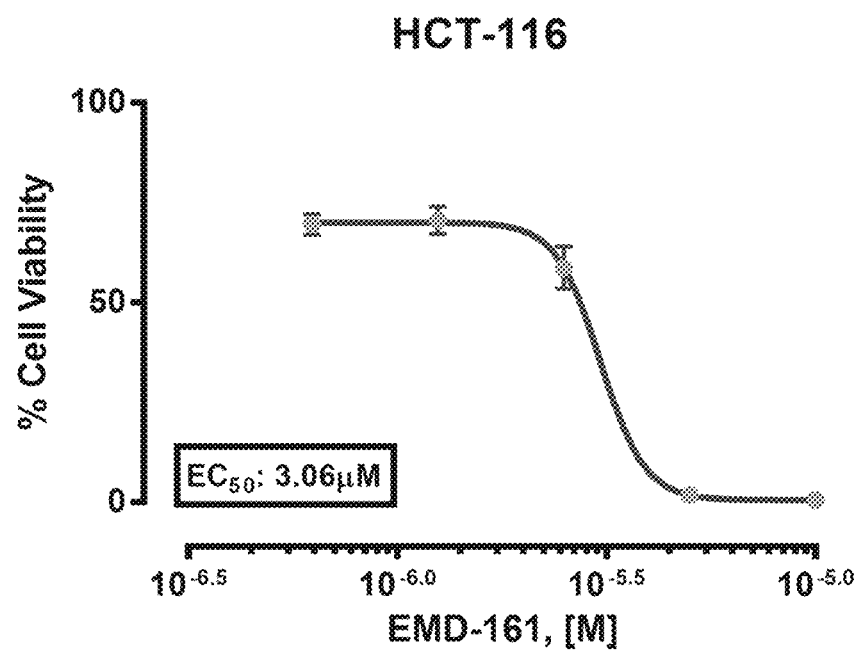
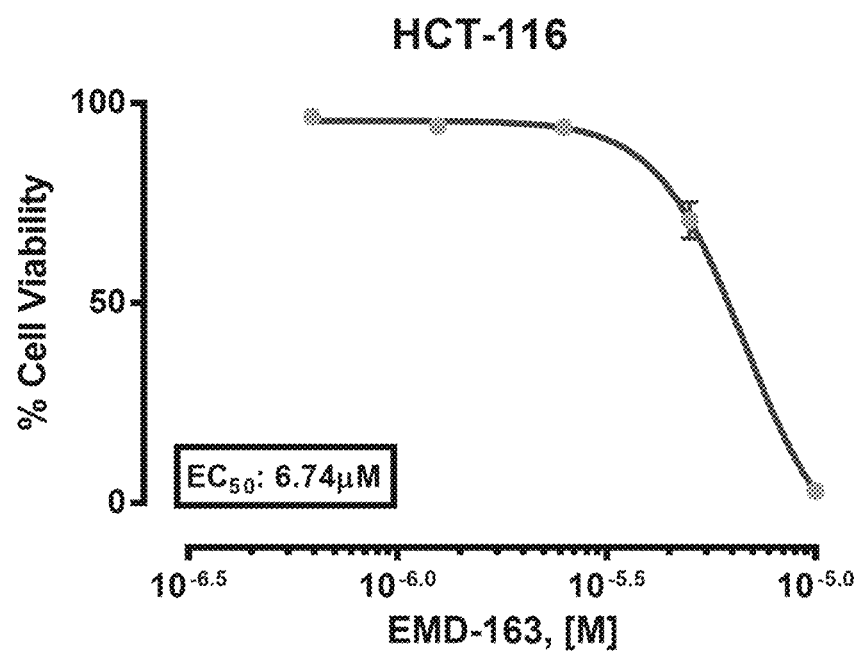

FIG. 5C

| Compound | HCT-116 Cell Viability at 10 μM |
|---|---|
| EMD-167 | 88% |
| EMD-171 | 32% |
| EMD-172 | 97% |
| EMD-173 | 65% |
| EMD-174 | 16% |
| EMD-176 | 75% |
| EMD-181 | 3% |
| EMD-182 | 34% |
| EMD-183 | 74% |
| EMD-184 | 32% |
| EMD-186 | 64% |
| EMD-191 | 94% |
| EMD-194 | 49% |
| EMD-196 | 88% |

FIG. 6

| Compound ID | EGFR | PI3K Alpha |
|---|---|---|
| MOL-150 | D | D |
| MOL-151 | A | D |
| MOL-153 | B | A |
| MOL-154 | D | B |
| MOL-160 | A | A |
| MOL-162 | A | A |
| MOL-163 | A | A |
| MOL-165 | A | A |
| MOL-166 | A | A |
| MOL-167 | A | A |
| MOL-167 | A | A |
| MOL-171 | A | B |
| MOL-172 | A | D |
| MOL-173 | A | D |
| MOL-174 | A | D |
| MOL-175 | A | B |
| MOL-176 | A | D |
| MOL-177 | A | B |
| MOL-181 | A | C |
| MOL-181 | A | C |
| MOL-182 | A | C |
| MOL-183 | A | D |
| MOL-184 | A | C |
| MOL-185 | A | B |
| MOL-186 | A | D |
| MOL-191 | A | B |
| MOL-192 | A | D |
| MOL-193 | A | D |
| MOL-194 | A | B |
| MOL-194 | A | B |
| MOL-195 | A | A |
| MOL-196 | A | D |
| MOL-200 | A | D |
| MOL-201 | A | A |
| MOL-501 | A | A |
| MOL-202 | A | A |
| MOL-502 | A | B |
| MOL-204 | A | B |
| MOL-205 | A | A |
| MOL-207 | A | B |
| MOL-210 | A | C |
| MOL-211 | A | A |
| MOL-212 | A | D |
| MOL-213 | A | B |
| MOL-214 | A | B |
| MOL-310 | A | C |
| MOL-311 | A | B |
| MOL-312 | A | B |
| MOL-313 | A | A |
| MOL-400 | D | B |
| MOL-401 | C | A |
| MOL-402 | D | C |
| MOL-403 | B | C |

A – IC50 < 100 nM
B – IC50 >100 nM and <1 uM
C – IC50 > 1uM and < 10 uM
D – IC50 > 10 uM

SMALL MOLECULE INHIBITORS OF EGFR AND PI3K

The present application is a divisional of U.S. patent application Ser. No. 15/536,528, filed Jun. 15, 2017, which is a 371-national entry application of Application No. PCT/US2015/065827, filed Dec. 15, 2015, which claims priority to U.S. Provisional Patent Application No. 62/091,969, filed Dec. 15, 2014, the contents of which are herein incorporated by reference in their entireties.

STATEMENT REGARDING FEDERALLY SPONSORED RESEARCH OR DEVELOPMENT

This invention was made with government support under Grant No. CA130810 awarded by the National Institutes of Health. The government has certain rights in the invention.

FIELD OF THE INVENTION

This invention is in the field of medicinal chemistry. In particular, the invention relates to a new class of small-molecules having a quinazoline structure or a quinoline structure which function as dual inhibitors of EGFR proteins and PI3K proteins, and their use as therapeutics for the treatment of cancer and other diseases.

INTRODUCTION

Colorectal cancer is the third most prevalent malignancy in the United States with approximately 145,000 new diagnoses and 56,000 deaths estimated for 2005 (see, e.g., Cancer Facts and Figures 2005, Surveillance Research (Washington, D.C.: American Cancer Society, Inc.), 2005). Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recurrence.

Improved methods for preventing and/or treating colorectal cancer are needed.

SUMMARY OF THE INVENTION

Experiments conducted during the course of developing embodiments for the present invention synthesized quinazoline derivatives and quinoline derivatives for the modulation (e.g., inhibition) of the activity or function of proteins of the phosphoinositide 3' OH kinase family (PIK3) (e.g., PIK3Cα, PIK3δ, PIK3β, PIK3Cγ, PI3Kα) and modulation (e.g., inhibition) of the activity or function of proteins of the epidermal growth factor EGFR family (e.g., ERBB receptor tyrosine kinase family (e.g., ERBB1, ERBB2, ERBB4, ERBB1)). In particular, utilizing x-ray crystal structure and structure-activity relationships gleaned from known PI3K and EGFR inhibiting agents, such experiments resulted in the identification of "active cores" for PI3K inhibiting agents facilitating high inhibitory activity against PI3K, and the identification of "active cores" for EGFR inhibiting agents facilitating high inhibitory activity against EGFR, respectively (see, Example I). The quinazoline compounds and quinoline compounds of the present invention were accordingly synthesized to target the "active cores" for PI3K and the "active cores" for EGFR, thereby rendering such compounds as having "dual potency" against PI3K and EGFR.

PI3K is negatively regulated by phosphatase and tensin homolog (PTEN) (see, e.g., Hamada K, et al., 2005 Genes Dev 19 (17): 2054-65). Numerous studies have shown a link between PIK3CA mutation/PTEN loss and EGFR targeted resistance leading to poor overall survival (see, e.g., Atreya C E, Sangale Z, Xu N, et al. Cancer Med. 2013; 2: 496-506; Sawai H, et al., BMC Gastroenterol. 2008; 8: 56; Bethune G, et al., J Thorac Dis. 2010; 2: 48-51; Spano J P, et al., Ann Oncol. 2005; 16: 189-194; Heimberger A B, et al., J Transl Med. 2005; 3: 38). The quinazoline compounds and quinoline compounds synthesized during the course of developing embodiments for the present invention were designed based on a central hypothesis that dual targeting of EGFR and PIK3CA would be efficacious in patients with colorectal cancer that are EGFR positive and are either PIK3CA mutated or null PTEN expressers (see, e.g., Psyrri A, et al., Am Soc Clin Oncol Educ Book. 2013: 246-255; Lui V W, et al., Cancer Discov. 2013; 3: 761-769; Jin G, et al., Lung Cancer. 2010; 69: 279-283; Buck E, et al., Mol Cancer Ther. 2006; 5: 2676-2684; Fan Q W, et al., Cancer Res. 2007; 67: 7960-7965; Gadgeel S M, et al., Clin Lung Cancer. 2013; 14: 322-332.

As such, the present invention relates to a new class of small-molecules having a quinazoline structure or quinoline structure which function as dual inhibitors of EGFR protein and PI3K protein, and their use as therapeutics for the treatment of conditions characterized by aberrant EGFR and PI3K expression (e.g., cancer and other diseases (e.g., autoimmune disorders, inflammatory diseases, cardiovascular diseases, neurodegenerative diseases, allergy, asthma, pancreatitis, multiorgan failure, kidney diseases, platelet aggregation, sperm motility, transplantation rejection, graft rejection, lung injuries, etc)). Indeed, through targeting both EGFR and PI3K, the compounds of the present invention are useful in treating subjects with EGFR positive colorectal cancer that harbor an activating mutation in PI3Kα or are PTEN null.

Accordingly, the present invention contemplates that exposure of animals (e.g., humans) suffering from a condition characterized by aberrant EGFR protein activity (e.g., ERBB1) and PI3K protein activity (e.g., PI3Kα) (e.g., cancer (e.g., and/or cancer related disorders)) to therapeutically effective amounts of drug(s) having a quinazoline structure (e.g., small molecules having a quinazoline structure) or a quinoline structures (e.g., small molecules having a quinoline structure) that inhibit the activity of both EGFR and PI3K will inhibit the growth of cells characterized by aberrant EGFR and PI3K protein expression (e.g., colorectal cancer cells having aberrant EGFR and PI3K protein expression) and/or render such cells as a population more susceptible to the cell death-inducing activity of additional therapeutic drugs (e.g., cancer therapeutic drugs or radiation therapies). The present invention contemplates that inhibitors of both EGFR and PI3K satisfy an unmet need for the treatment of multiple conditions characterized with aberrant EGFR and PI3K activity (e.g., cancer), either when administered as monotherapy to induce cell growth inhibition, apoptosis and/or cell cycle arrest in such cells (e.g., cancer cells), or when administered in a temporal relationship with additional agent(s), such as other cell death-inducing or cell cycle disrupting therapeutic drugs (e.g., cancer therapeutic drugs or radiation therapies) (combination therapies), so as to render a greater proportion of the cells (e.g., cancer cells) or supportive cells susceptible to executing the apoptosis program compared to the corresponding proportion of cells in an animal treated only with the therapeutic drug or radiation therapy alone.

In certain embodiments of the invention wherein the condition being treated is cancer characterized with aberrant EGFR protein activity (e.g., ERBB1) and PI3K protein activity (e.g., PI3Kα) (e.g., colorectal cancer), combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

As noted, the Applicants have found that certain quinazoline compounds and quinoline compounds function as inhibitors of both EGFR and PI3K, and serve as therapeutics for the treatment of cancer and other diseases. Thus, the present invention relates to quinazoline compounds and quinoline compounds useful for inhibiting EGFR and PI3K activity (e.g., thereby facilitating cell apoptosis), and increasing the sensitivity of cells to inducers of apoptosis and/or cell cycle arrest. Certain quinazoline compounds and quinoline compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, quinazoline compounds having Formula I

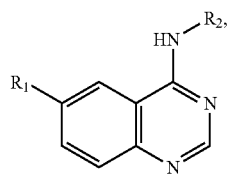

(Formula I)

including pharmaceutically acceptable salts, solvates, and/or prodrugs thereof, are provided.

In a particular embodiment, quinoline compounds having Formula II

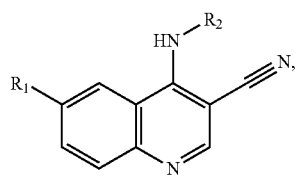

(Formula II)

including pharmaceutically acceptable salts, solvates, and/or prodrugs thereof, are provided.

Formulas I and II are not limited to a particular chemical moiety for R1 and R2. In some embodiments, the particular chemical moiety for R1 and R2 independently include any chemical moiety that permits the resulting compound to inhibit an EGFR protein (e.g., ERBB1) and inhibit a PI3K protein (e.g., PI3Kα).

In some embodiments, R1 is a substituted or non-substituted aryl moiety. In some embodiments, R1 is selected from

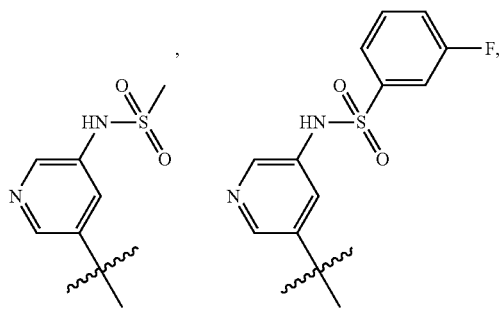

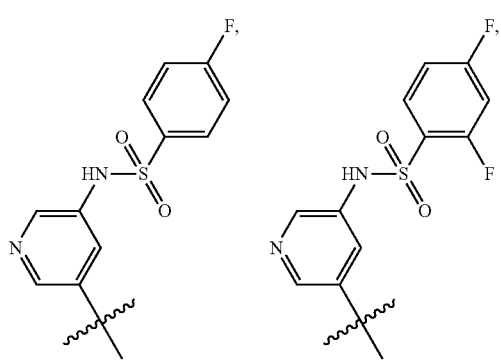

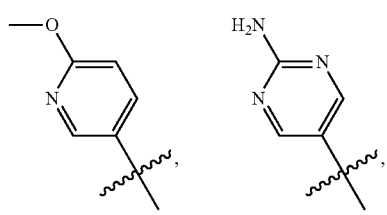

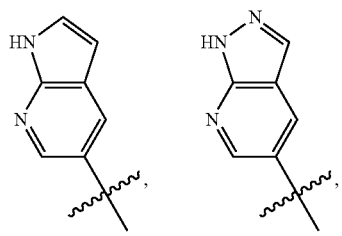

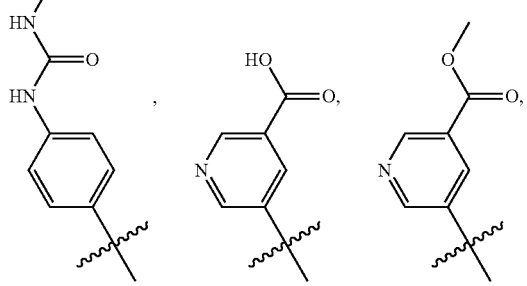

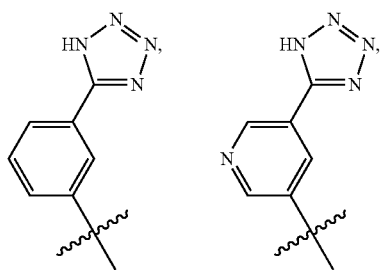
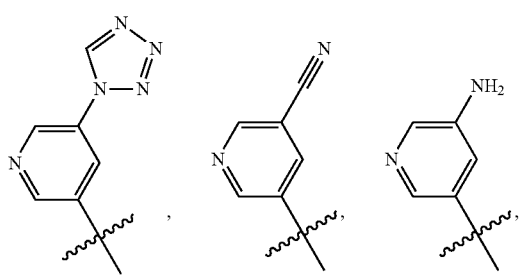
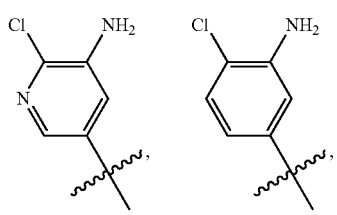
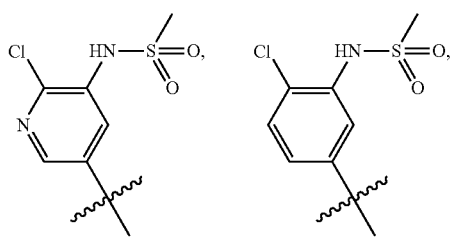
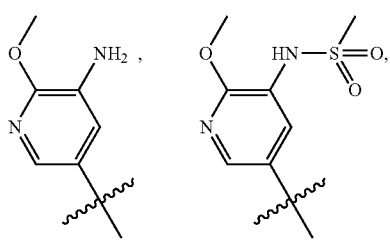
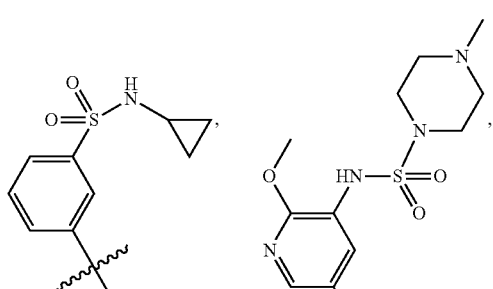
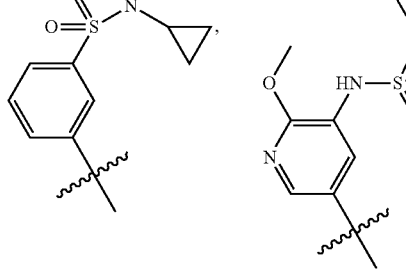
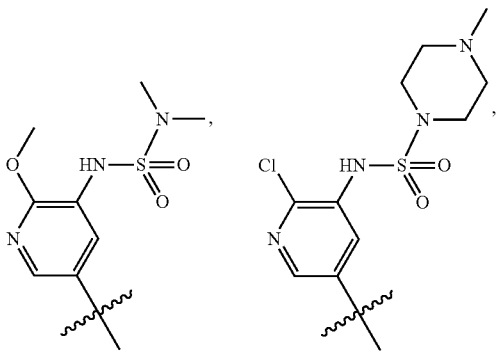
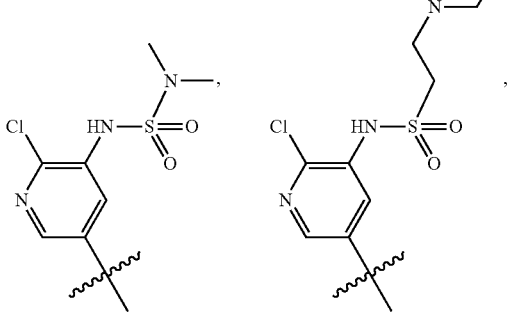
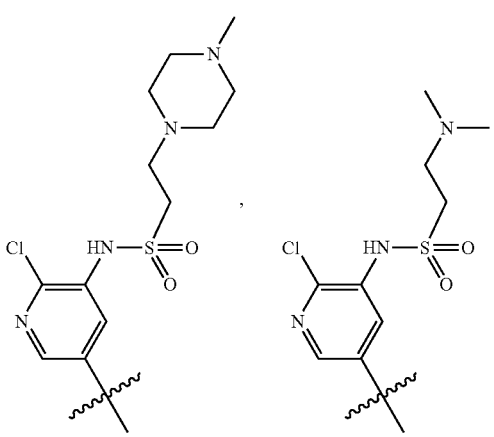
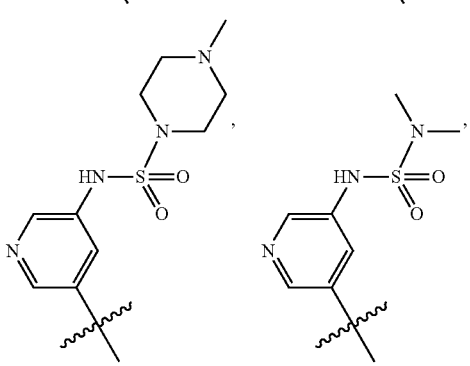

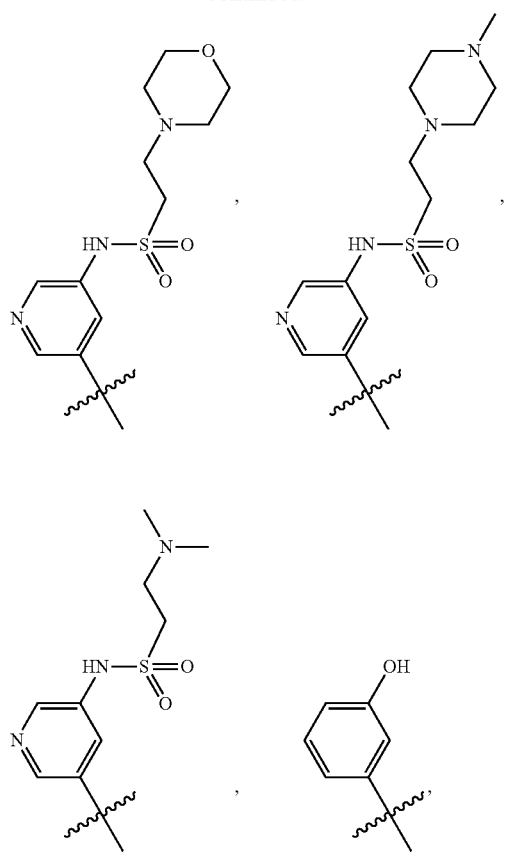
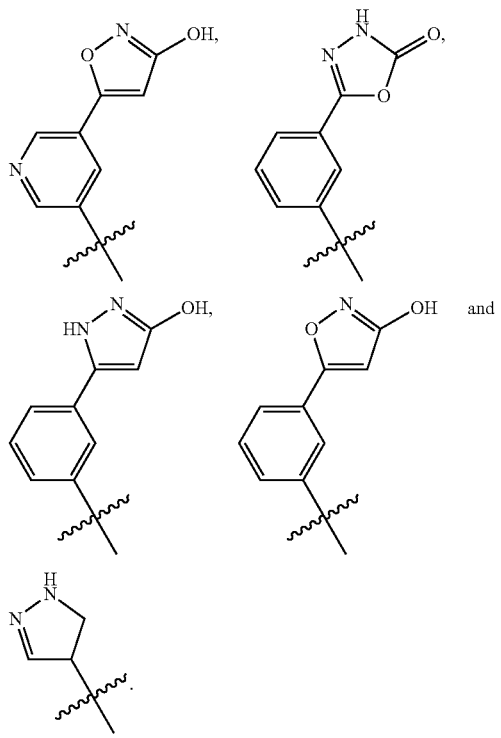
In some embodiments, R2 is a substituted or non-substituted aryl moiety. In some embodiments, R2 is selected from -continued
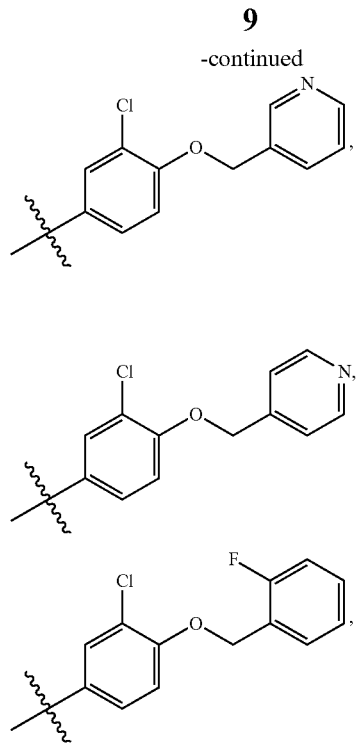
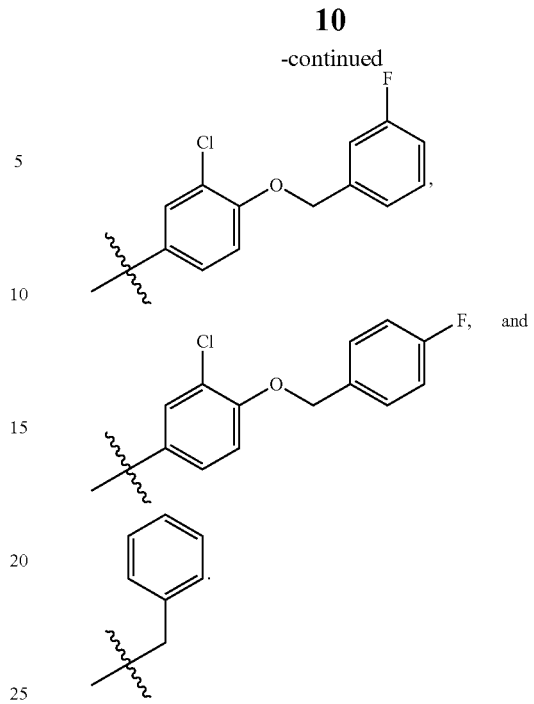
In some embodiments, the following compounds are contemplated for Formulas I and II:
| IUPAC Name and Chemical Structure | Compound ID |
|---|---|
| 4-((3-chloro-4-fluorophenyl)amino)-6-(6-methoxypyridin-3-yl)quinoline-3-carbonitrile 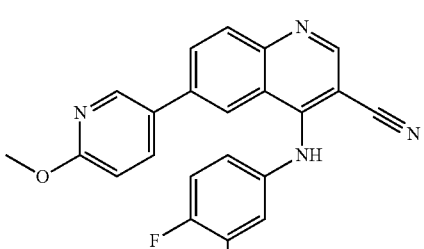 | MOL-150 |
| N-(3-chloro-4-flluorophenyl)-6-(6-methoxypyridin-3-yl)quinazolin-4-amine 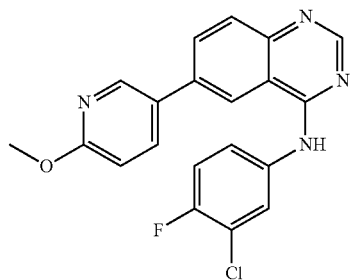 | MOL-151 |

-continued

| IUPAC Name and Chemical Structure | Compound ID |
|---|---|
| N-(5-(4-((3-chloro-4-methoxyphenyl)amino)quinazolin-6-yl)pyridin-3-yl)methanesulfonamide | MOL-153 |

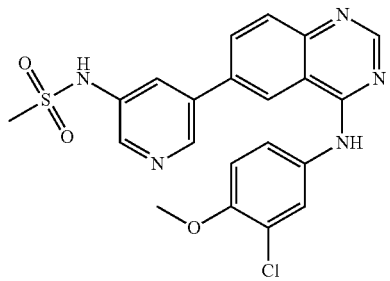

| N-(5-4-((3-chloro-4-methoxyphenyl)amino)quinazolin-6-yl)pyridin-3-yl)-3-fluorobenzenesulfonamide | MOL-154 |

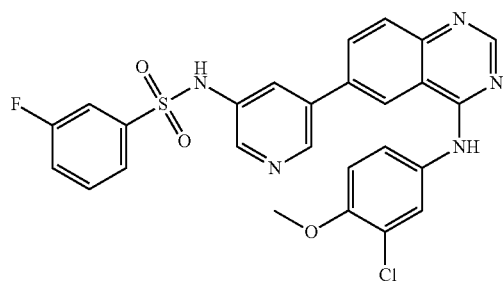

MOL-160

| N-(5-(4-((3-chloro-4-fluorophenyl)amino)quinazolin-6-yl)pyridin-3-yl)methanesulfonamide | |

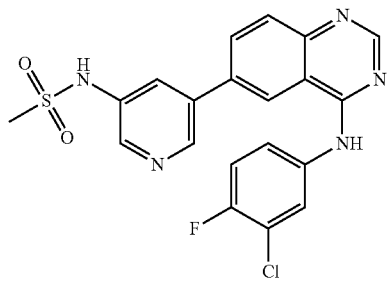

| N-(5-(4-((3-ethynylphenyl)amino)quinazolin-6-yl)pyridin-3-yl)methanesulfonamide | MOL-161 |

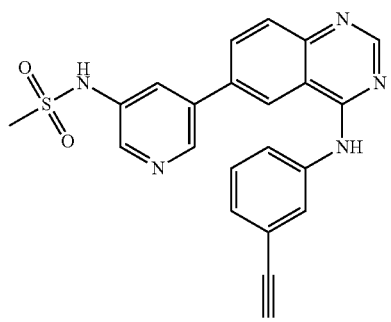

| IUPAC Name and Chemical Structure | Compound ID |
|---|---|
| N-(5-(4-((3-chlorophenyl)amino)quinazolin-6-yl)pyridin-3-yl)methanesulfonamide | MOL-162 |
| N-(5-(4-((5-chloropyridin-3-yl)amino)quinazolin-6-yl)pyridin-3-yl)methanesulfonamide | MOL-163 |
| N-(5-(4-((3-bromophenyl)amino)quinazolin-6-yl)pyridin-3-yl)methanesulfonamide | MOL-165 |
| N-(5-(4-((4-(pyridin-4-yloxy)phenyl)amino)quinazolin-6-yl)pyridin-3-yl)methanesulfonamide | MOL-166 |

-continued
| IUPAC Name and Chemical Structure | Compound ID |
|---|---|
| N-(5-(4-(benzylamino)quinazolin-6-yl)pyridin-3-yl)methanesulfonamide 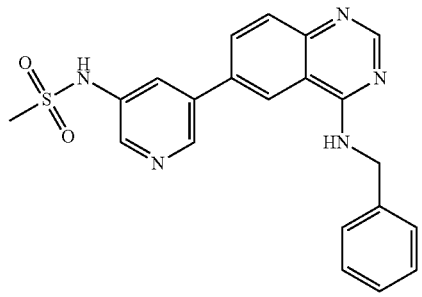 | MOL-167 |
| 6-(2-aminopyrimidin-5-yl)-N-(3-chlorophenyl)quinazolin-4-amine 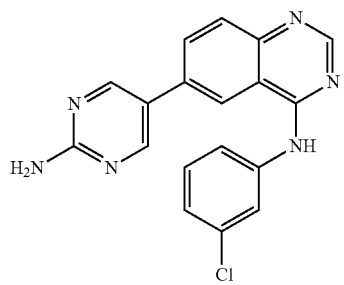 | MOL-171 |
| N-(3-chlorophenyl)-6-(1H-pyrrolo[2,3-b]pyridin-5-yl)quinazolin-4-amine 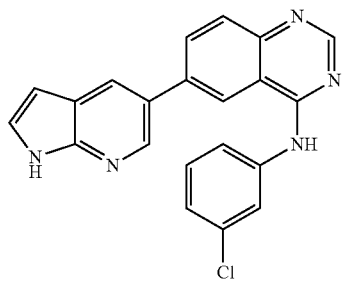 | MOL-172 |
| 1-(4-(4-((3-chllorophenyl)amino)quinazolin-6-yl)phenyl)-3-methylurea 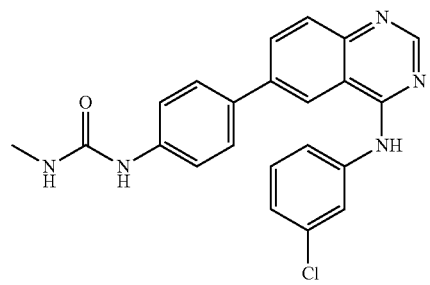 | MOL-173 |

-continued
| IUPAC Name and Chemical Structure | Compound ID |
|---|---|
| N-(3-(4-((3-chlorophenyl)amino)quinazolin-6-yl)phenyl)methanesulfonamide 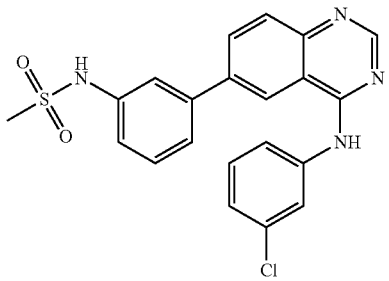 | MOL-174 |
| 6-(3-(1H-tetrazol-5-yl)phenyl)-N-(3-chlorophenyl)quinazollin-4-amine 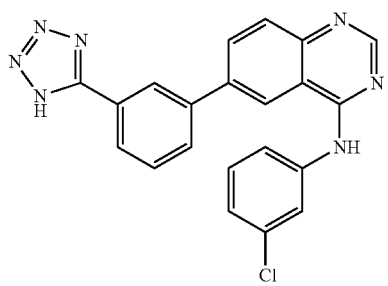 | MOL-175 |
| N-(3-chlorophenyl)-6-(1H-pyrazol-4-yl)quinazolin-4-amine 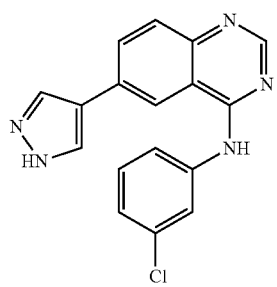 | MOL-176 |
| 6-(2-aminopyrimidin-5-yl)-N-(3-chloro-4-fluorophenyl)quinazolin-4-amine 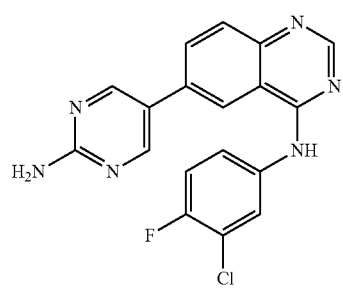 | MOL-181 |

| IUPAC Name and Chemical Structure | Compound ID |
|---|---|
| N-(3-chloro-4-fluorophenyl)-6-(1H-pyrrolo[2,3-b]pyridin-5-yl)quinazolin-4-amine 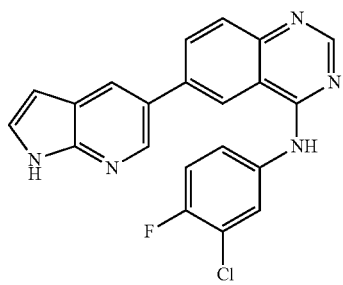 | MOL-182 |
| 1-(4-(4-((3-chloro-4-fluorophenyl)amino)quinazolin-6-yl)phenyl)-3-methylurea 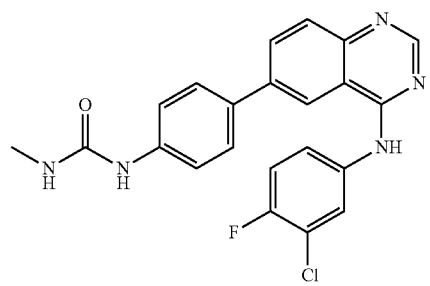 | MOL-183 |
|  | MOL-184 |
| N-(3-(4-((3-chloro-4-fluorophenyl)amino)quinazolin-6-yl)phenyl)methanesulfonamide 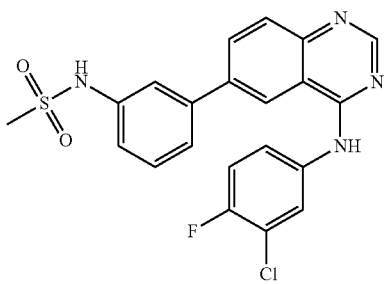 |  |
| 6-(3-(1H-tetrazol-5-yl)phenyl)-N-(3-chloro-4-fluorophenyl)quinazolin-4-amine 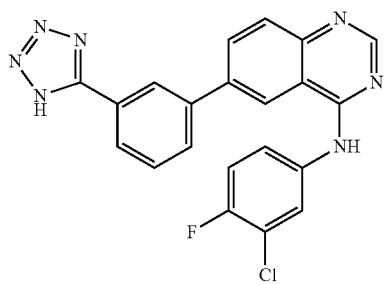 | MOL-185 |

-continued
| IUPAC Name and Chemical Structure | Compound ID |
|---|---|
| N-(3-chloro-4-fluorophenyl)-6-(1H-pyrazol-4-yl)quinazolin-4-amine 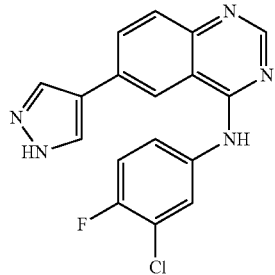 | MOL-186 |
| 6-(2-aminopyrimidin-5-yl)-N-(5-chloropyridin-3-yl)quinazolin-4-amine 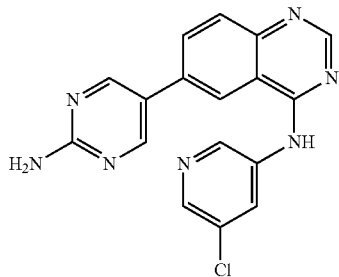 | MOL-191 |
| N-(5-chloropyridin-3-yl)-6-(1H-pyrrolo[2,3-b]pyridin-5-yl)quinazolin-4-amine 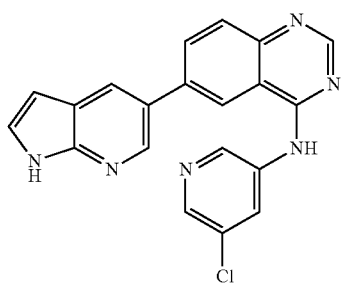 | MOL-192 |
| 1-(4-(4-((5-chloropyridin-3-yl)amino)quinazolin-6-yl)phenyl)-3-methylurea 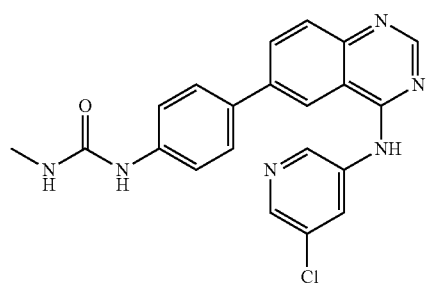 | MOL-193 |

| IUPAC Name and Chemical Structure | Compound ID |
|---|---|
| N-(3-(4-((5-chloropyridin-3-yl)amino)quinazolin-6-yl)phenyl)methanesulfonamide 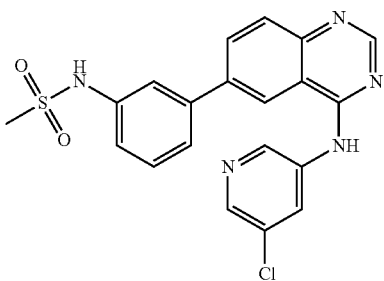 | MOL-194 |
| | MOL-195 |
| 6-(3-(1H-tetrazol-5-yl)phenyl)-N-(5-chloropyridin-3-yl)quinazolin-4-amine 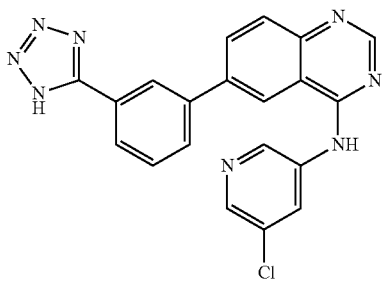 | |
| N-(5-chloropyridin-3-yl)-6-(1H-pyrazol-4-yl)quinazolin-4-amine 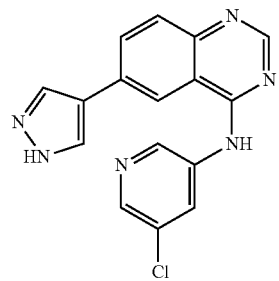 | MOL-196 |
| | MOL-177 |
| N-(3-chlorophenyl)-6-(1H-pyrazolo[3,4-b]pyridin-5-yl)quinazolin-4-amine 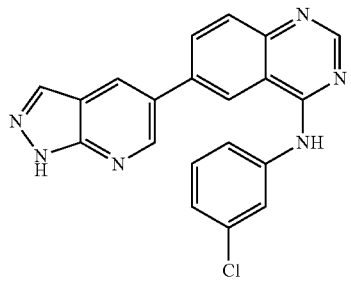 | |

| IUPAC Name and Chemical Structure | Compound ID |
|---|---|
| 6-(5-amino-6-chloropyridin-3-yl)-N-(3-chlorophenyl)quinazolin-4-amine 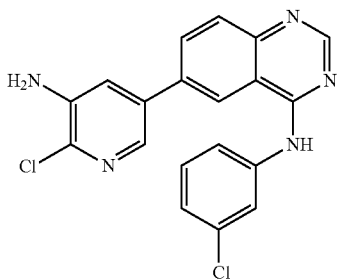 | MOL-200 |
| N-(2-chloro-5-(4-((3-chlorophenyl)amino)quinazolin-6-yl)pyridin-3-yl)methanesulfonamide 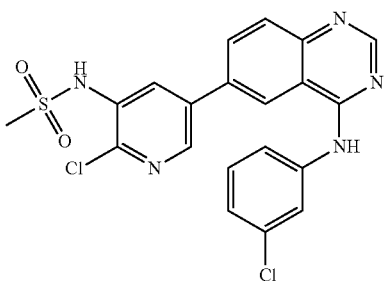 | MOL-201 |
| N-(2-chloro-5-(4-((3-chlorophenyl)amino)quinazolin-6-yl)pyridin-3-yl)-N-(methylsulfonyl)methanesulfonamide 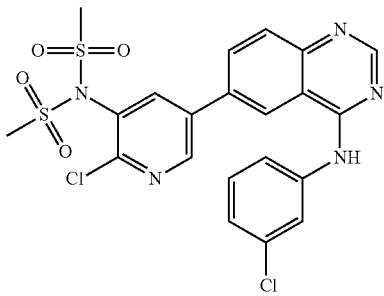 | MOL-201B |
| N-(5-(4-((3-chlorophenyl)amino)quinaolin-6-yl)-2-methoxypyridin-3-yl)methanesulfonamide 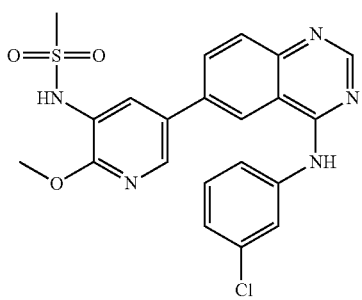 | MOL-202 |

| IUPAC Name and Chemical Structure | Compound ID |
|---|---|
| N-(5-(4-((3-chlorophenyl)amino)quinazolin-6-yl)-2-methoxypyridin-3-yl)-N-(methylsulfonyl)methanesulfonamide 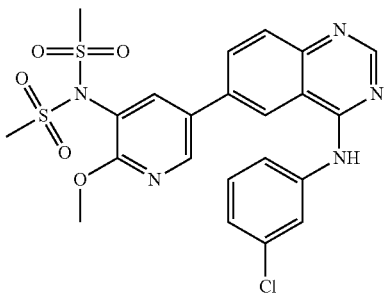 | MOL-202B |
| N-(5-(4-((3-chlorophenyl)amino)quinazolin-6-yl)-2-methoxypyridin-3-yl)ethenesulfonamide 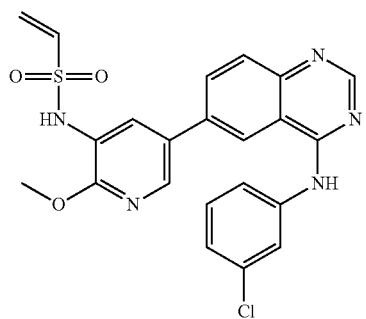 | MOL-203 |
| N-(5-(4-((3-chlorophenyl)amino)quinazollin-6-yl)-2-methoxypyridin-3-yl)cyclopropanesulfonamide 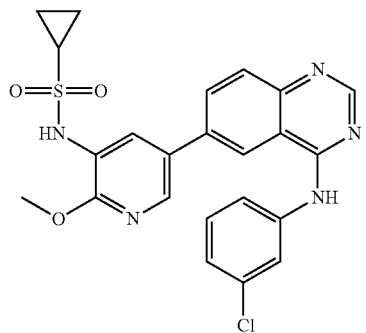 | MOL-204 |

| IUPAC Name and Chemical Structure | Compound ID |
|---|---|
| N-(5-(4-((3-chlorophenyl)amino)quinazolin-6-yl)-2-methoxypyridin-3-yl)-2-morpholinoethane-1-sulfonamide 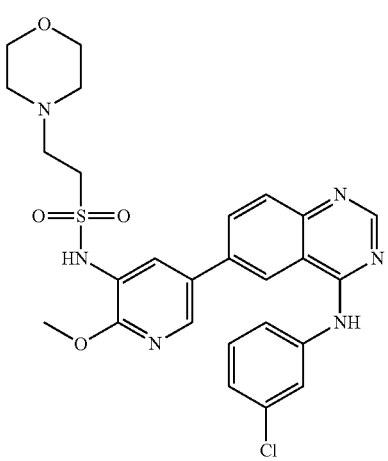 | MOL-205 |
| N-(5-(4-((3-chlorophenyl)amino)quinazolin-6-yl)-2-methoxypyridin-3-yl)-4-methylpiperazine-1-sulfonamide 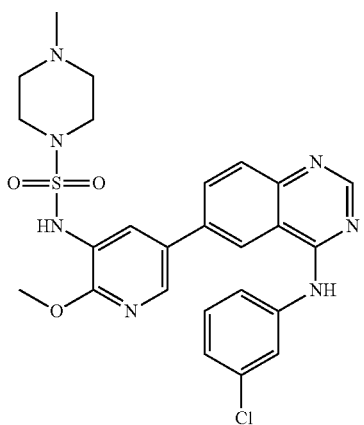 | MOL-207 |
| 6-bromo-4-((4-(pyridin-4-yloxy)phenyl)amino)quinoline-3-carbonitrile 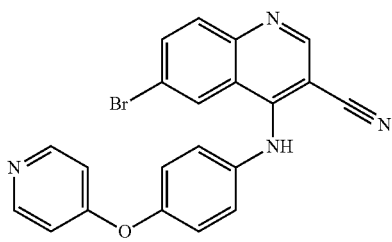 | MOL-400 |
| N-(5-(3-cyano-4-((4-(pyridin-4-yloxy)phenyl)amino)quinolin-6-yl)pyridin-3-yl)methanesulfonamide 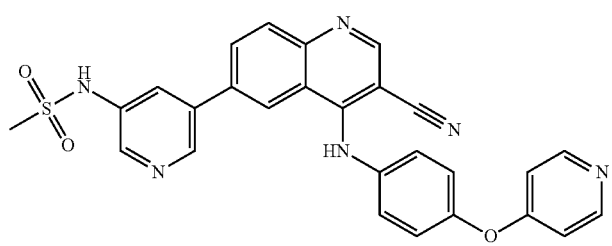 | MOL-401 |

| IUPAC Name and Chemical Structure | Compound ID |
|---|---|
| 6-(3-(hydroxymethyl)phenyl)-4-((4-(pyridin-4-yloxy)phenyl)amino)quinoline-3-carbonitrile 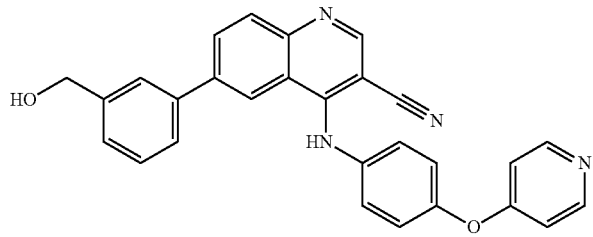 | MOL-402 |
| 6-(3-hydroxyphenyl)-4-((4-(pyridin-4-yloxy)phenyl)amino)quinoline-3-carbonitrile 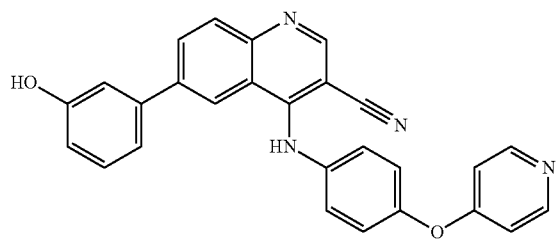 | MOL-403 |
| 6-(pyridin-3-ylethynyl)-4-((4-(pyridin-4-yloxy)phenyl)amino)quinoline-3-carbonitrile 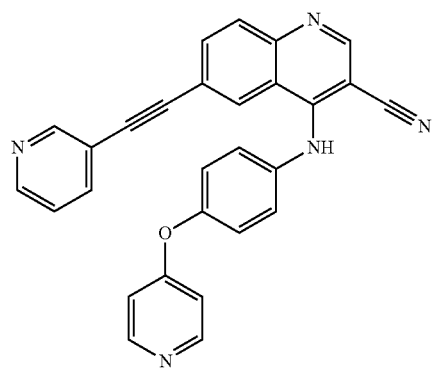 | MOL-404 |
| 6-(5-aminopyridin-3-yl)-N-(3-chlorophenyl)quinazolin-4-amine 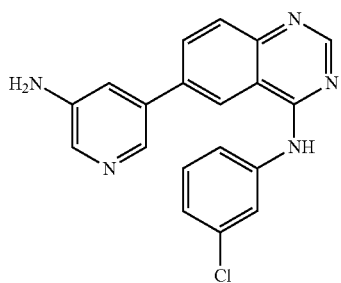 | MOL-310 |

| IUPAC Name and Chemical Structure | Compound ID |
|---|---|
| 6-(5-(1H-tetrazol-1-yl)pyridin-3-yl)-N-(3-chlorophenyl)quinazolin-4-amine 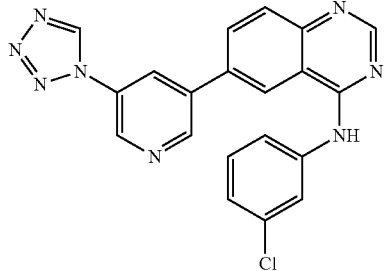 | MOL-311 |
| 5-(4-((3-chlorophenyl)amino)quinazolin-6-yl)nicotinonitrile 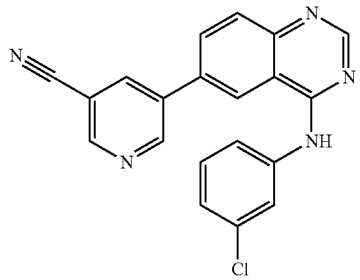 | MOL-312 |
| 6-(5-(1H-tetrazol-5-yl)pyridin-3-yl)-N-(3-chlorophenyl)quinazolin-4-amine 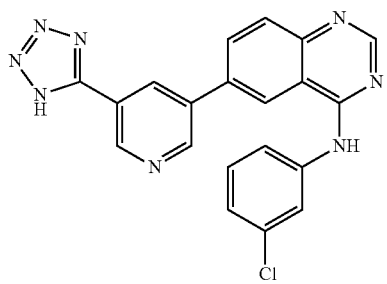 | MOL-313 |
| methyl 5-(4-((3-chlorophenyl)amino)quinazolin-6-yl)nicotinate 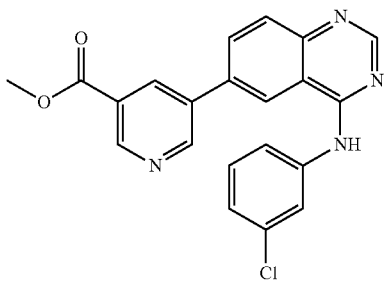 | MOL-318 |

| IUPAC Name and Chemical Structure | Compound ID |
|---|---|
| 5-(4-((3-chlorophenyl)amino)quinazolin-6-yl)nicotinic acid 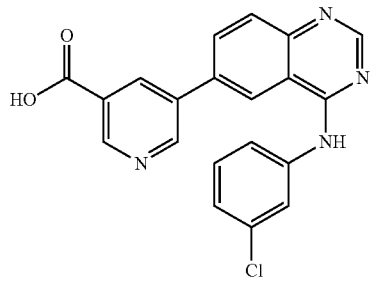 | MOL-314 |
| 5-(5-(4-((3-chlorophenyl)amino)quinazolin-6-yl)pyridin-3-yl)-1,3,4-oxadiazol-2(3H)-one 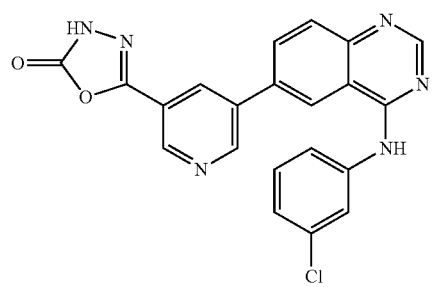 | MOL-315 |
| 2-(5-(4-((3-chlorophenyl)amino)quinazolin-6-yl)nicotinoyl)-N-(2-morpholinoethyl)hydrazine-1-carboxamide 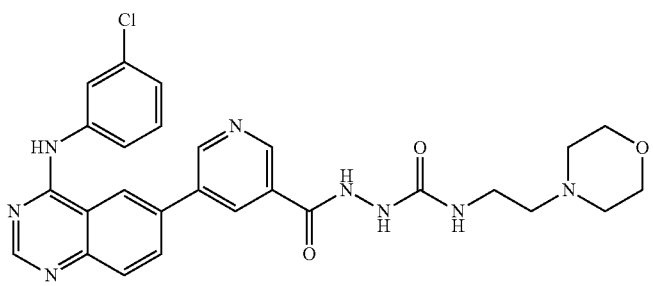 | MOL-316 |
| 5-(5-(4-((3-chlorophenyl)amino)quinazolin-6-yl)pyridin-3-yl)-N-(2-morpholinoethyl)-1,3,4-oxadiazol-2-amine 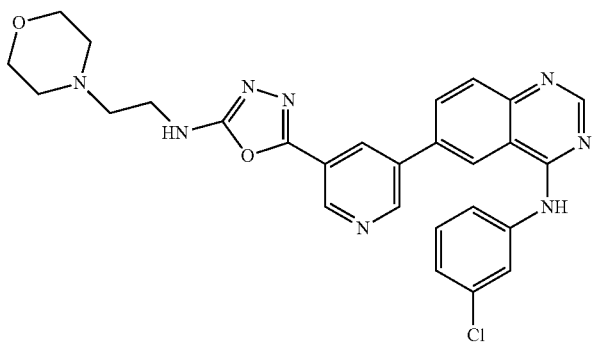 | MOL-317 |

| IUPAC Name and Chemical Structure | Compound ID |
|---|---|
| 6-(5-amino-6-chloropyridin-3-yl)-N-(3-chloro-4-fluorophenyl)quinazolin-4-amine 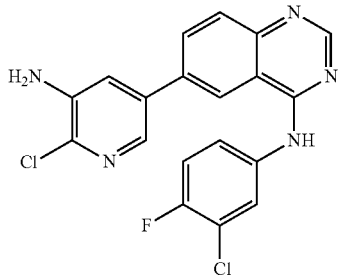 | MOL-210 |
| N-(2-chloro-5-(4-((3-chloro-4-fluorophenyl)amino)quinazolin-6-yl)pyridin-3-yl)methanesulfonamide 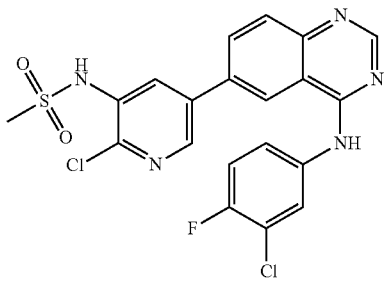 | MOL-211 |
|  | MOL-212 |
| 6-(3-amino-4-chlorophenyl)-N-(3-chloro-4-fluorophenyl)quinazoline-4-amine 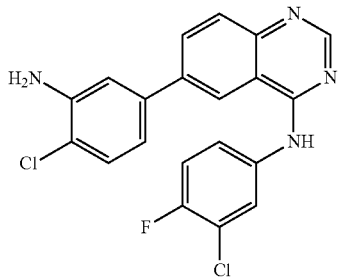 |  |
| N-(2-chloro-5-(4-((3-chloro-4-fluorophenyl)amino)quinazolin-6-yl)phenyl)methanesulfonamide 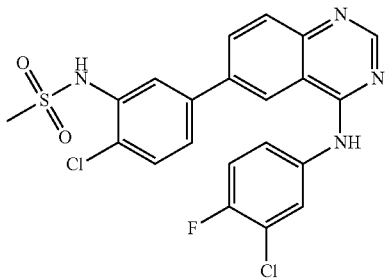 | MOL-213 |

| IUPAC Name and Chemical Structure | Compound ID |
|---|---|
| 3-(4-((3-chloro-4-fluorophenyl)amino)quinazolin-6-yl)-N-cyclopropylbenzenesulfonamide 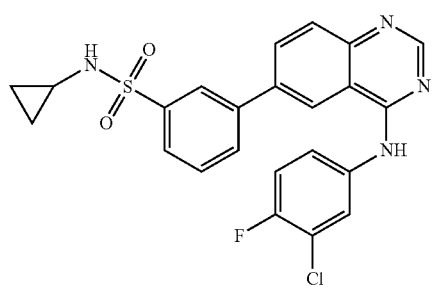 | MOL-214 |
| N-(2-chloro-5-(4-((3-chloro-4-(pyridin-2-ylmethoxy)phenyl)amino)quinazolin-5-yl)pyridin-3-yl)methanesulfonamide 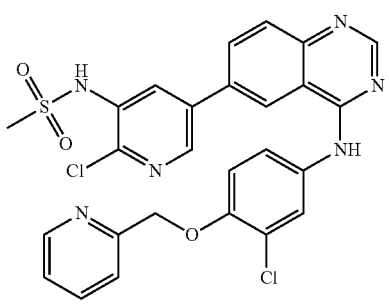 | MOL-215 |
| N-(2-chloro-5-(4-((3-chloro-4-fluorophenyl)amino)-3-cyanoquinolin-6-yl)pyridin-3-yl)methanesulfonamide 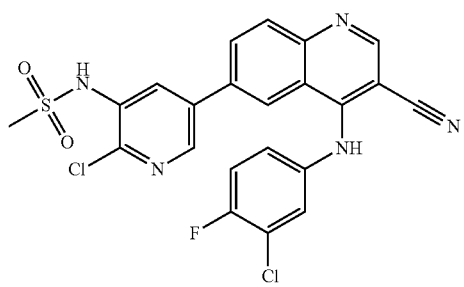 | MOL-216 |
| N-(2-chloro-5-(4-((3-chloro-4-fluorophenyl)amino)quinazolin-6-yl)pyridin-3-yl)-2-(4-methylpiperazin-1-yl)ethane-1-sulfonamide 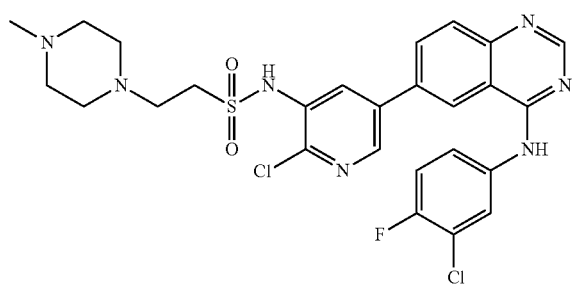 | MOL-220 |

| IUPAC Name and Chemical Structure | Compound ID |
|---|---|
| N-(2-chloro-5-(4-((3-chloro-4-fluorophenyl)amino)quinazolin-6-yl)pyridin-3-yl)-2-(dimethylamino)ethane-1-sulfonamide 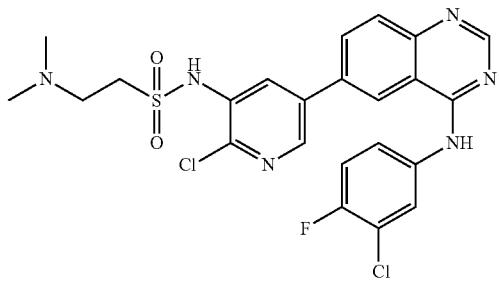 | MOL-221 |
| | MOL-222 |
| N-(2-chloro-5-(4-((3-chloro-4-fluorophenyl)amino)quinazolin-6-yl)pyridin-3-yl)-2-morpholinoethane-1-sulfonamide 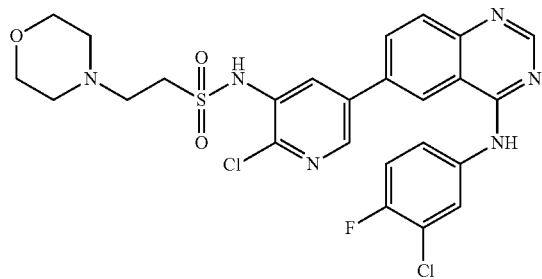 | |
| N-(5-(4-((3-chloro-4-fluorophenyl)amino)quinazolin-6-yl)pyridin-3-yl)-2-(4-methylpiperazin-1-yl)ethane-1-sulfonamide 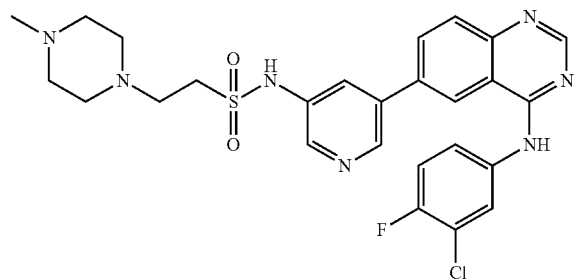 | MOL-230 |
| N-(5-(4-((3-chloro-4-fluorophenyl)amino)quinazolin-6-yl)pyridin-3-yl)-2-(dimethylamino)ethane-1-sulfonamide 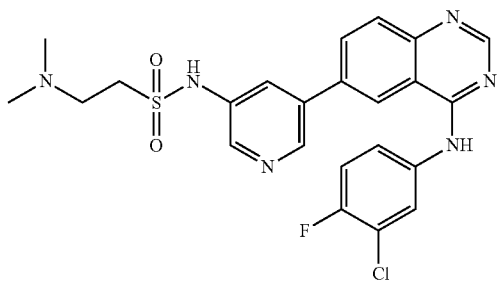 | MOL-231 |

| IUPAC Name and Chemical Structure | Compound ID |
|---|---|
| N-(5-(4-((3-chloro-4-fluorophenyl)amino)quinazolin-6-yl)pyridin-3-yl)-2-morpholinoethane-1-sulfonamide 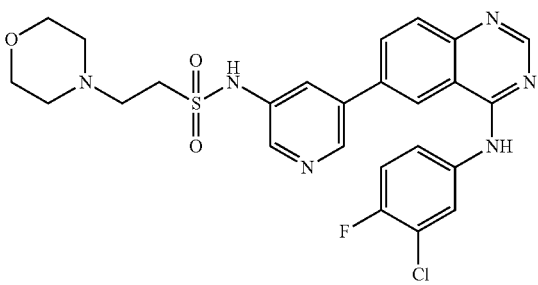 | MOL-232 |

The invention further provides processes for preparing any of the compounds of the present invention.

The invention also provides the use of compounds to induce cell cycle arrest and/or apoptosis in cells characterized with aberrant EGFR protein activity (e.g., ERBB1) and PI3K protein activity (e.g., PI3Kα). The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer characterized with cells aberrant EGFR protein activity (e.g., ERBB1) and PI3K protein activity (e.g., PI3Kα) (e.g., colorectal cancer). In certain embodiments, the compounds can be used to treat, ameliorate, or prevent such types of cancer (e.g., colorectal cancer) that is characterized by resistance to cancer therapies (e.g., those cancer cells which are chemoresistant, radiation resistant, hormone resistant, and the like). In certain embodiments, the cancer is colorectal cancer, head & neck cancer, glioblastoma multiform, and/or non-small cell lung cancer (NSCLC). In other embodiments, the compounds can be used to treat other characterized by aberrant expression of EGFR and PI3K proteins (e.g., autoimmune disorders, inflammatory diseases, cardiovascular diseases, neurodegenerative diseases, allergy, asthma, pancreatitis, multiorgan failure, kidney diseases, platelet aggregation, sperm motility, transplantation rejection, graft rejection, lung injuries, etc).

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents.

Moreover, the present invention provides methods for simultaneously inhibiting both EGFR protein activity and PI3K protein activity in cells through exposing such cells to one or more of the quinazoline or quinoline compounds of the present invention.

BRIEF DESCRIPTION OF DRAWINGS

FIG. 3 shows the X-ray Crystal quinolone binding mode in EGFR (ATP competitive site of protein kinases) for Lapatinib (PDB Code: 1XKK) and HKI-272 (PDB Code: 3W2Q).
FIG. 5A shows that phosphorylation of EGFR was found to be completely suppressed in HCT-116 tumors (100 mg/kg) at two hours post-dosing of a single oral dose of MOL-162.
FIG. 5B shows a measurement of cell proliferation for MOL-160, MOL-161, MOL-162, and MOL-163.
FIG. 5C shows HCT-116 cell viability for various compounds.
FIG. 6 shows IC50s of various compounds against EGFR and PIK3CA.

DEFINITIONS

Figure 1A:
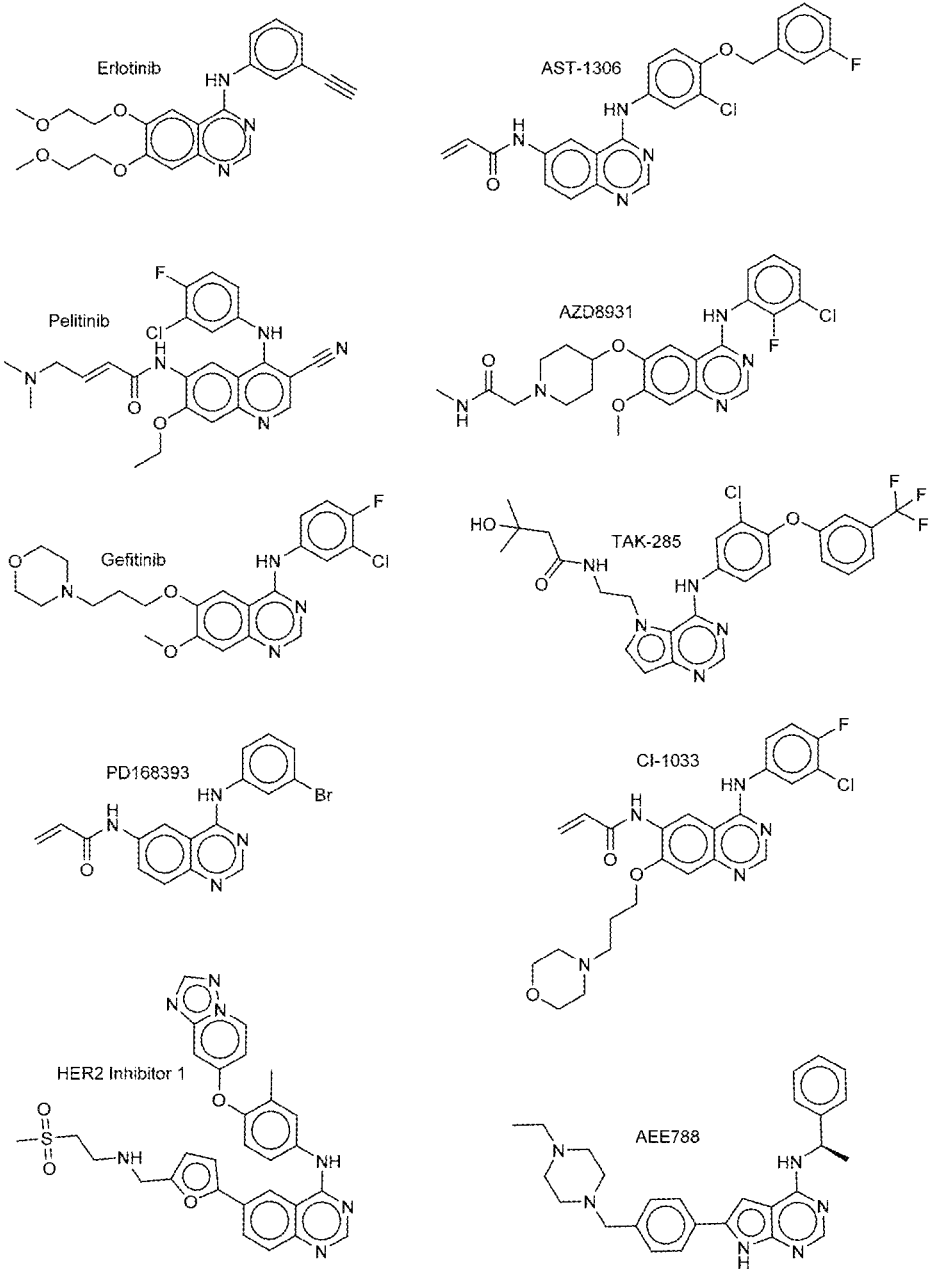
FIG. 1A-C shows EGFR inhibiting agents.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a quinazoline compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

In spite of compelling evidence for PI3K/AKT pathway activation leading to resistance to EGFR targeting agents, only recently have researchers sought to combine EGFR targeting agents with PI3K/AKT/MTOR pathway inhibitors both pre-clinically and clinically. For example, Buck et al demonstrated that the mTOR inhibitor rapamycin synergizes with the EGFR inhibitor erlotinib in several cell lines that were resistant to erlotinib treatment alone (e.g., Ratushny V, et al., Cell Signal. 2009; 21: 1255-1268). However, the full potential of this synergistic combination was not achieved because rapamycin induces phosphorylation of AKT resulting in pathway reactivation (e.g., Ratushny V, et al., Cell Signal. 2009; 21: 1255-1268). Others have explored dual inhibition of EGFR and PI3K/AKT pathways in several cell lines and cancer histotypes, providing further support for this combination treatment strategy (see, e.g., Eichhorn P J, et al., Cancer Res. 2008; 68: 9221-9230). The compounds of the present invention overcame such limitations and represent dual potency inhibitors of both EGFR protein activity (e.g., ERBB1) and PI3K protein activity (e.g., PI3Kα). Specifically, utilizing x-ray crystal structure and structure-activity relationships gleaned from known PI3K and EGFR inhibiting agents, such experiments resulted in the identification of "active cores" for PI3K inhibiting agents facilitating high inhibitory activity against PI3K, and the identification of "active cores" for EGFR inhibiting agents facilitating high inhibitory activity against EGFR, respectively (see, Example I). The quinazoline and quinoline compounds of the present invention were accordingly synthesized to target the "active cores" for PI3K and the "active cores" for EGFR, thereby rendering such compounds as having "dual potency" against EGFR protein activity (e.g., ERBB1) and PI3K protein activity (e.g., PI3Kα).

Accordingly, the present invention relates to compounds which function as inhibitors of EGFR protein activity (e.g., ERBB1) and PI3K protein activity (e.g., PI3Kα). By inhibiting the activity of EGFR protein activity (e.g., ERBB1) and PI3K protein activity (e.g., PI3Kα), these compounds sensitize cells to inducers of apoptosis and/or cell cycle arrest and, in some instances, themselves induce apoptosis and/or cell cycle arrest. Therefore, the invention relates to methods of sensitizing cells to inducers of apoptosis and/or cell cycle arrest and to methods of inducing apoptosis and/or cell cycle arrest in cells, comprising contacting the cells with a compound of the invention alone or in combination with additional agent(s), e.g., an inducer of apoptosis or a cell cycle disrupter.

The invention further relates to methods of treating, ameliorating, or preventing conditions in a patient characterized with cells having aberrant EGFR protein activity (e.g., ERBB1) and PI3K protein activity (e.g., PI3Kα), such as those conditions that are responsive to induction of apoptosis, comprising administering to the patient a compound of the invention and additional agent(s), e.g., an inducer of apoptosis. Such disorders include those characterized by a dysregulation of apoptosis and those characterized by the proliferation of cells having aberrant EGFR protein activity (e.g., ERBB1) and PI3K protein activity (e.g., PI3Kα) (e.g., colorectal cancer). Indeed, through targeting both EGFR and PI3K, the compounds of the present invention are useful in treating subjects with EGFR positive colorectal cancer that harbor an activating mutation in PI3Kα or are PTEN null.

In a particular embodiment, quinazoline compounds having Formula I

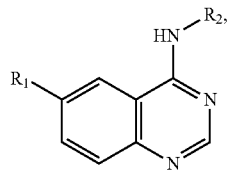

(Formula I)

including pharmaceutically acceptable salts, solvates, and/or prodrugs thereof, are provided.

In a particular embodiment, quinoline compounds having Formula II

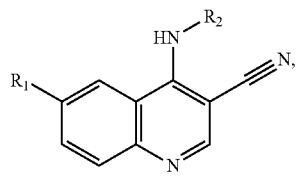

(Formula II)

including pharmaceutically acceptable salts, solvates, and/or prodrugs thereof, are provided.

Formulas I and II are not limited to a particular chemical moiety for R1 and R2. In some embodiments, the particular chemical moiety for R1 and R2 independently include any chemical moiety that permits the resulting compound to inhibit an EGFR protein (e.g., ERBB1) and inhibit a PI3K protein (e.g., PI3Kα).

In some embodiments, R1 is a substituted or non-substituted aryl moiety. In some embodiments, R1 is selected from

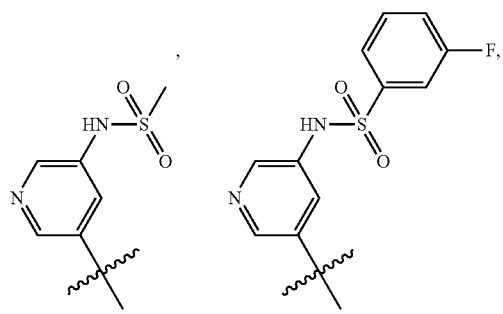

-continued

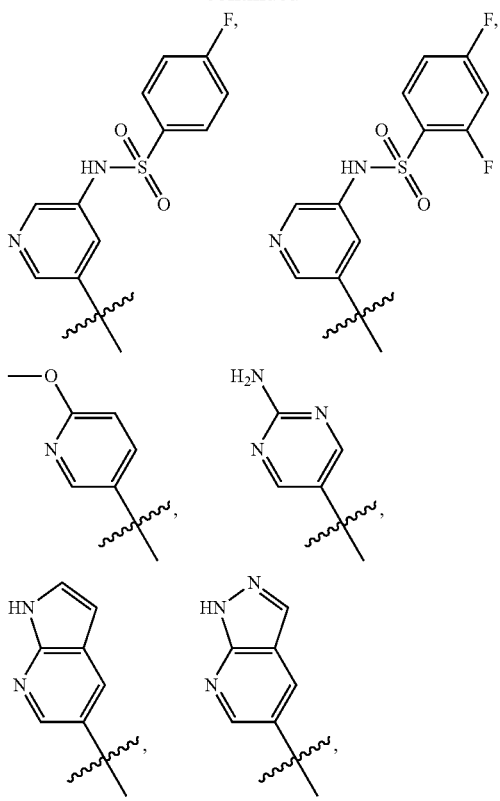

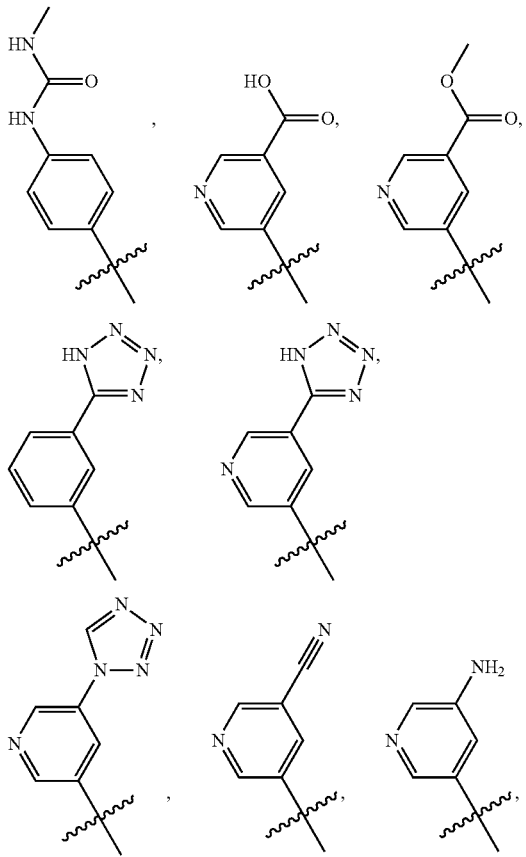

51
-continued
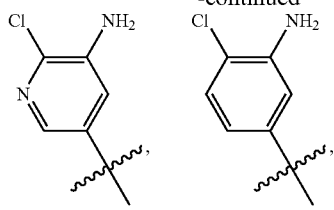
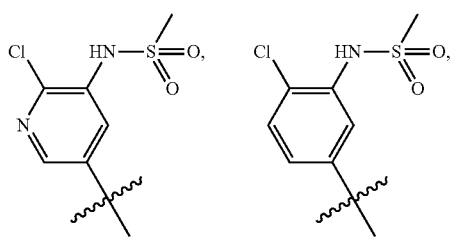
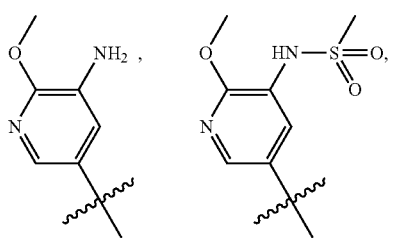
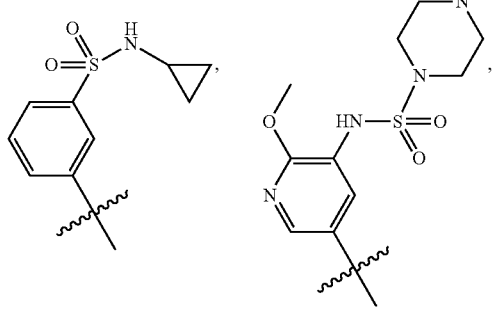
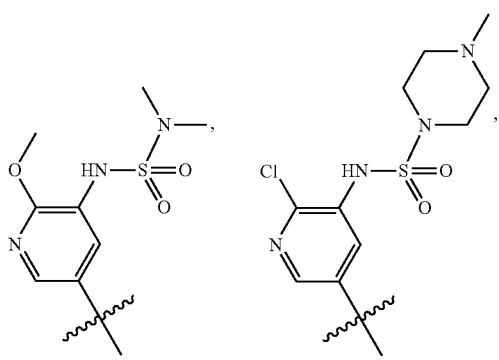
52
-continued
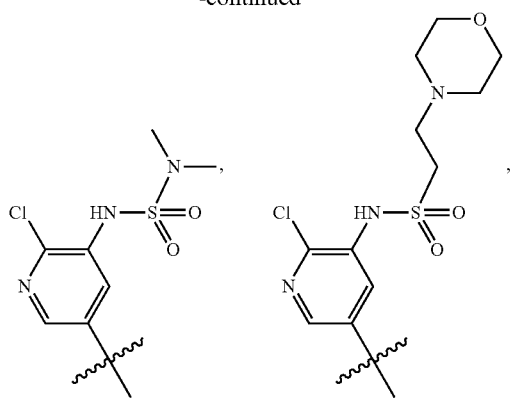
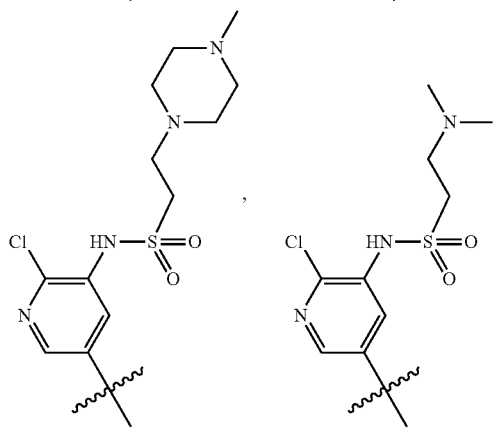
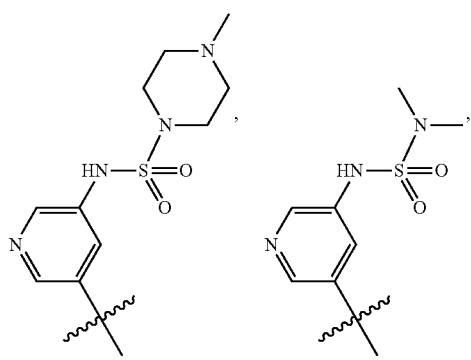
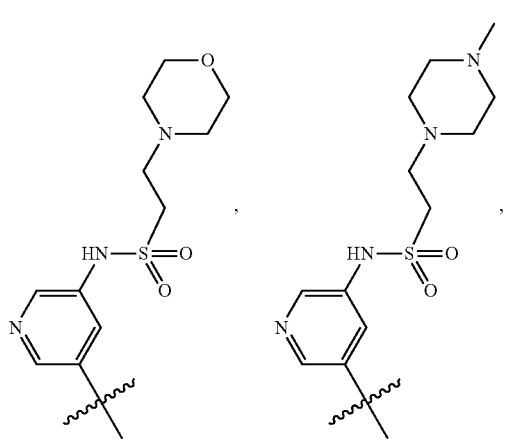

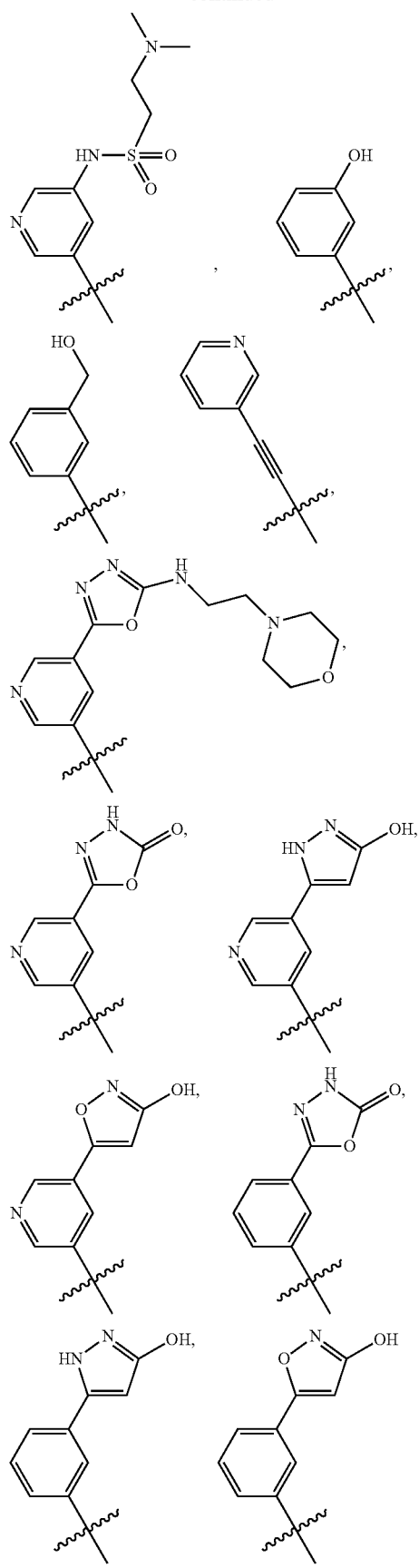
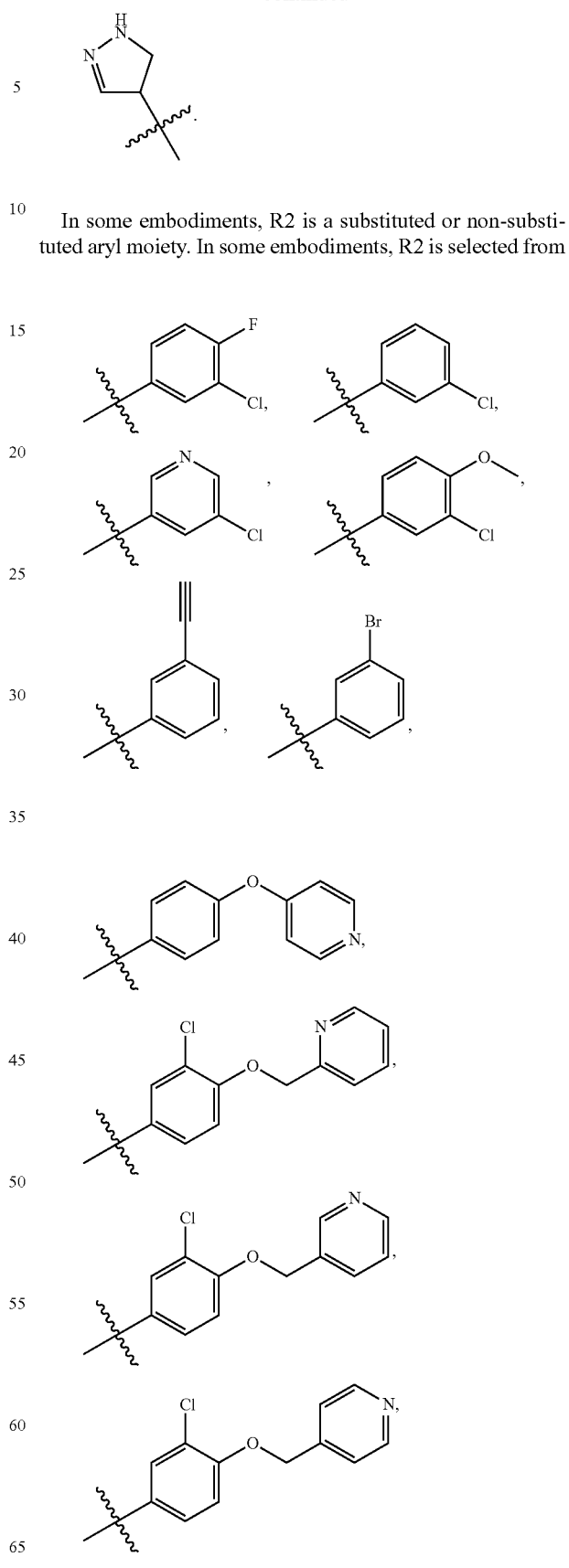
In some embodiments, R2 is a substituted or non-substituted aryl moiety. In some embodiments, R2 is selected from -continued

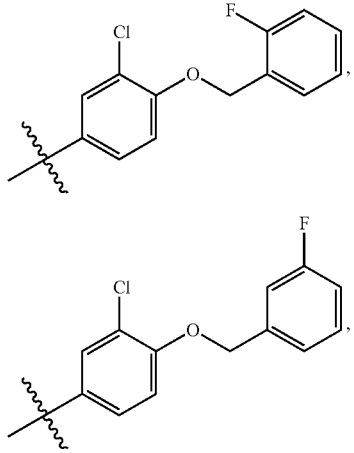

-continued

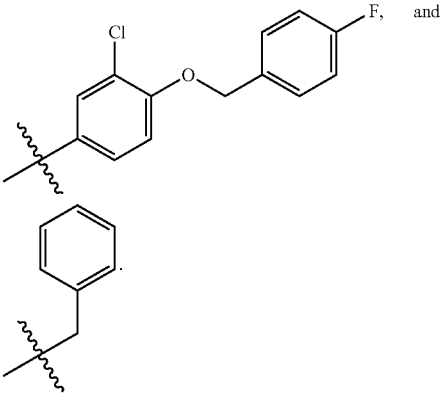

In some embodiments, the following compounds are contemplated for Formulas I and II:

| IUPAC Name | Compound ID |
|---|---|
| 4-((3-chloro-4-fluorophenyl)amino)-6-(6-methoxypyridin-3-yl)quinoline-3-carbonitrile | MOL-150 |
| N-(3-chloro-4-fluorophenyl)-6-(6-methoxypyridin-3-yl)quinazolin-4-amine | MOL-151 |
| N-(5-(4-((3-chloro-4-methoxyphenyl)amino)quinazolin-6-yl)pyridin-3-yl)methanesulfonamide | MOL-153 |
| N-(5-(4-((3-chloro-4-methoxyphenyl)amino)quinazolin-6-yl)pyridin-3-yl)-3-fluorobenzenesulfonamide | MOL-154 |
| N-(5-(4-((3-chloro-4-fluorophenyl)amino)quinazolin-6-yl)pyridin-3-yl)methanesulfonamide | MOL-160 |
| N-(5-(4-((3-ethynylphenyl)amino)quinazolin-6-yl)pyridin-3-yl)methanesulfonamide | MOL-161 |
| N-(5-(4-((3-chlorophenyl)amino)quinazolin-6-yl)pyridin-3-yl)methanesulfonamide | MOL-162 |
| N-(5-(4-((5-chloropyridin-3-yl)amino)quinazolin-6-yl)pyridin-3-yl)methanesulfonamide | MOL-163 |
| N-(5-(4-((3-bromophenyl)amino)quinazolin-6-yl)pyridin-3-yl)methanesulfonamide | MOL-165 |
| N-(5-(4-((4-(pyridin-4-yloxy)phenyl)amino)quinazolin-6-yl)pyridin-3-yl)methanesulfonamide | MOL-166 |
| N-(5-(4-(benzylamino)quinazolin-6-yl)pyridin-3-yl)methanesulfonamide | MOL-167 |
| 6-(2-aminopyrimidin-5-yl)-N-(3-chlorophenyl)quinazolin-4-amine | MOL-171 |
| N-(3-chlorophenyl)-6-(1H-pyrrolo[2,3-b]pyridin-5-yl)quinazolin-4-amine | MOL-172 |
| 1-(4-(4-((3-chlorophenyl)amino)quinazolin-6-yl)phenyl)-3-methylurea | MOL-173 |
| N-(3-(4-((3-chlorophenyl)amino)quinazolin-6-yl)phenyl)methanesulfonamide | MOL-174 |
| 6-(3-(1H-tetrazol-5-yl)phenyl)-N-(3-chlorophenyl)quinazolin-4-amine | MOL-175 |
| N-(3-chlorophenyl)-6-(1H-pyrazol-4-yl)quinazolin-4-amine | MOL-176 |
| 6-(2-aminopyrimidin-5-yl)-N-(3-chloro-4-fluorophenyl)quinazolin-4-amine | MOL-181 |
| N-(3-chloro-4-fluorophenyl)-6-(1H-pyrrolo[2,3-b]pyridin-5-yl)quinazolin-4-amine | MOL-182 |
| 1-(4-(4-((3-chloro-4-fluorophenyl)amino)quinazolin-6-yl)phenyl)-3-methylurea | MOL-183 |
| N-(3-(4-((3-chloro-4-fluorophenyl)amino)quinazolin-6-yl)phenyl)methanesulfonamide | MOL-184 |
| 6-(3-(1H-tetrazol-5-yl)phenyl)-N-(3-chloro-4-fluorophenyl)quinazolin-4-amine | MOL-185 |
| N-(3-chloro-4-fluorophenyl)-6-(1H-pyrazol-4-yl)quinazolin-4-amine | MOL-186 |
| 6-(2-aminopyrimidin-5-yl)-N-(5-chloropyridin-3-yl)quinazolin-4-amine | MOL-191 |
| N-(5-chloropyridin-3-yl)-6-(1H-pyrrolo[2,3-b]pyridin-5-yl)quinazolin-4-amine | MOL-192 |
| 1-(4-(4-((5-chloropyridin-3-yl)amino)quinazolin-6-yl)phenyl)-3-methylurea | MOL-193 |
| N-(3-(4-((5-chloropyridin-3-yl)amino)quinazolin-6-yl)phenyl)methanesulfonamide | MOL-194 |
| 6-(3-(1H-tetrazol-5-yl)phenyl)-N-(5-chloropyridin-3-yl)quinazolin-4-amine | MOL-195 |
| N-(5-chloropyridin-3-yl)-6-(1H-pyrazol-4-yl)quinazolin-4-amine | MOL-196 |
| N-(3-chlorophenyl)-6-(1H-pyrazolo[3,4-b]pyridin-5-yl)quinazolin-4-amine | MOL-177 |
| 6-(5-amino-6-chloropyridin-3-yl)-N-(3-chlorophenyl)quinazolin-4-amine | MOL-200 |
| N-(2-chloro-5-(4-((3-chlorophenyl)amino)quinazolin-6-yl)pyridin-3-yl)methanesulfonamide | MOL-201 |
| N-(2-chloro-5-(4-((3-chlorophenyl)amino)quinazolin-6-yl)pyridin-3-yl)-N-(methylsulfonyl)methanesulfonamide | MOL-201B |
| N-(5-(4-((3-chlorophenyl)amino)quinazolin-6-yl)-2-methoxypyridin-3-yl)methanesulfonamide | MOL-202 |
| N-(5-(4-((3-chlorophenyl)amino)quinazolin-6-yl)-2-methoxypyridin-3-yl)-N-(methylsulfonyl)methanesulfonamide | MOL-202B |

-continued

| IUPAC Name | Compound ID |
| --- | --- |
| N-(5-(4-((3-chlorophenyl)amino)quinazolin-6-yl)-2-methoxypyridin-3-yl)ethenesulfonamide | MOL-203 |
| N-(5-(4-((3-chlorophenyl)amino)quinazolin-6-yl)-2-methoxypyridin-3-yl)cyclopropanesulfonamide | MOL-204 |
| N-(5-(4-((3-chlorophenyl)amino)quinazolin-6-yl)-2-methoxypyridin-3-yl)-2-morpholinoethane-1-sulfonamide | MOL-205 |
| N-(5-(4-((3-chlorophenyl)amino)quinazolin-6-yl)-2-methoxypyridin-3-yl)-4-methylpiperazine-1-sulfonamide | MOL-207 |
| 6-bromo-4-((4-(pyridin-4-yloxy)phenyl)amino)quinoline-3-carbonitrile | MOL-400 |
| N-(5-(3-cyano-4-((4-(pyridin-4-yloxy)phenyl)amino)quinolin-6-yl)pyridin-3-yl)methanesulfonamide | MOL-401 |
| 6-(3-(hydroxymethyl)phenyl)-4-((4-(pyridin-4-yloxy)phenyl)amino)quinoline-3-carbonitrile | MOL-402 |
| 6-(3-hydroxyphenyl)-4-((4-(pyridin-4-yloxy)phenyl)amino)quinoline-3-carbonitrile | MOL-403 |
| 6-(pyridin-3-ylethynyl)-4-((4-(pyridin-4-yloxy)phenyl)amino)quinoline-3-carbonitrile | MOL-404 |
| 6-(5-aminopyridin-3-yl)-N-(3-chlorophenyl)quinazolin-4-amine | MOL-310 |
| 6-(5-(1H-tetrazol-1-yl)pyridin-3-yl)-N-(3-chlorophenyl)quinazolin-4-amine | MOL-311 |
| 5-(4-((3-chlorophenyl)amino)quinazolin-6-yl)nicotinonitrile | MOL-312 |
| 6-(5-(1H-tetrazol-5-yl)pyridin-3-yl)-N-(3-chlorophenyl)quinazolin-4-amine | MOL-313 |
| methyl 5-(4-((3-chlorophenyl)amino)quinazolin-6-yl)nicotinate | MOL-318 |
| 5-(4-((3-chlorophenyl)amino)quinazolin-6-yl)nicotinic acid | MOL-314 |
| 5-(5-(4-((3-chlorophenyl)amino)quinazolin-6-yl)pyridin-3-yl)-1,3,4-oxadiazol-2(3H)-one | MOL-315 |
| 2-(5-(4-((3-chlorophenyl)amino)quinazolin-6-yl)nicotinoyl)-N-(2-morpholinoethyl)hydrazine-1-carboxamide | MOL-316 |
| 5-(5-(4-((3-chlorophenyl)amino)quinazolin-6-yl)pyridin-3-yl)-N-(2-morpholinoethyl)-1,3,4-oxadiazol-2-amine | MOL-317 |
| 6-(5-amino-6-chloropyridin-3-yl)-N-(3-chloro-4-fluorophenyl)quinazolin-4-amine | MOL-210 |
| N-(2-chloro-5-(4-((3-chloro-4-fluorophenyl)amino)quinazolin-6-yl)pyridin-3-yl)methanesulfonamide | MOL-211 |
| 6-(3-amino-4-chlorophenyl)-N-(3-chloro-4-fluorophenyl)quinazolin-4-amine | MOL-212 |
| N-(2-chloro-5-(4-((3-chloro-4-fluorophenyl)amino)quinazolin-6-yl)phenyl)methanesulfonamide | MOL-213 |
| 3-(4-((3-chloro-4-fluorophenyl)amino)quinazolin-6-yl)-N-cyclopropylbenzenesulfonamide | MOL-214 |
| N-(2-chloro-5-(4-((3-chloro-4-(pyridin-2-ylmethoxy)phenyl)amino)quinazolin-6-yl)pyridin-3-yl)methanesulfonamide | MOL-215 |
| N-(2-chloro-5-(4-((3-chloro-4-fluorophenyl)amino)-3-cyanoquinolin-6-yl)pyridin-3-yl)methanesulfonamide | MOL-216 |
| N-(2-chloro-5-(4-((3-chloro-4-fluorophenyl)amino)quinazolin-6-yl)pyridin-3-yl)-2-(4-methylpiperazin-1-yl)ethane-1-sulfonamide | MOL-220 |
| N-(2-chloro-5-(4-((3-chloro-4-fluorophenyl)amino)quinazolin-6-yl)pyridin-3-yl)-2-(dimethylamino)ethane-1-sulfonamide | MOL-221 |
| N-(2-chloro-5-(4-((3-chloro-4-fluorophenyl)amino)quinazolin-6-yl)pyridin-3-yl)-2-morpholinoethane-1-sulfonamide | MOL-222 |
| N-(5-(4-((3-chloro-4-fluorophenyl)amino)quinazolin-6-yl)pyridin-3-yl)-2-(4-methylpiperazin-1-yl)ethane-1-sulfonamide | MOL-230 |
| N-(5-(4-((3-chloro-4-fluorophenyl)amino)quinazolin-6-yl)pyridin-3-yl)-2-(dimethylamino)ethane-1-sulfonamide | MOL-231 |
| N-(5-(4-((3-chloro-4-fluorophenyl)amino)quinazolin-6-yl)pyridin-3-yl)-2-morpholinoethane-1-sulfonamide | MOL-232 |

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The EGFR and PI3K inhibitors of the present invention (e.g., quinazoline compounds) (e.g., quinoline compounds) can be used to induce apoptosis in any disorder that can be treated, ameliorated, or prevented by the induction of apoptosis.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, colorectal cancer, non-small cell lung carcinoma, head or neck carcinoma, glioblastoma multiform cancer, pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents.

In other embodiments, the disorder is any disorder having cells having aberrant EGFR protein activity (e.g., ERBB1) and PI3K protein activity (e.g., PI3Kα) (e.g., autoimmune disorders, inflammatory diseases, cardiovascular diseases, neurodegenerative diseases, allergy, asthma, pancreatitis, multiorgan failure, kidney diseases, platelet aggregation, sperm motility, transplantation rejection, graft rejection, lung injuries, etc)).

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] | Cytoxan, Neosar | Bristol-Myers Squibb |

TABLE 1-continued

| | | |
|---|---|---|
| tetrahydro-2H-13,2-oxazaphosphorine 2-oxide monohydrate) | | |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin in PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |

TABLE 1-continued

| Drug | Brand | Company |
|---|---|---|
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tituxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \bullet HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |

TABLE 1-continued

| | | |
|---|---|---|
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5ß,20-Epoxy-1,2a,4,7ß,10ß,13a-hexahydroxytax-11-en-9-one 4,10-diacetate 2-benzoate 13-ester with (2R, 3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-µ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |

TABLE 1-continued

| | | |
|---|---|---|
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}$ $(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxy]]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)]-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

Figure 1B:
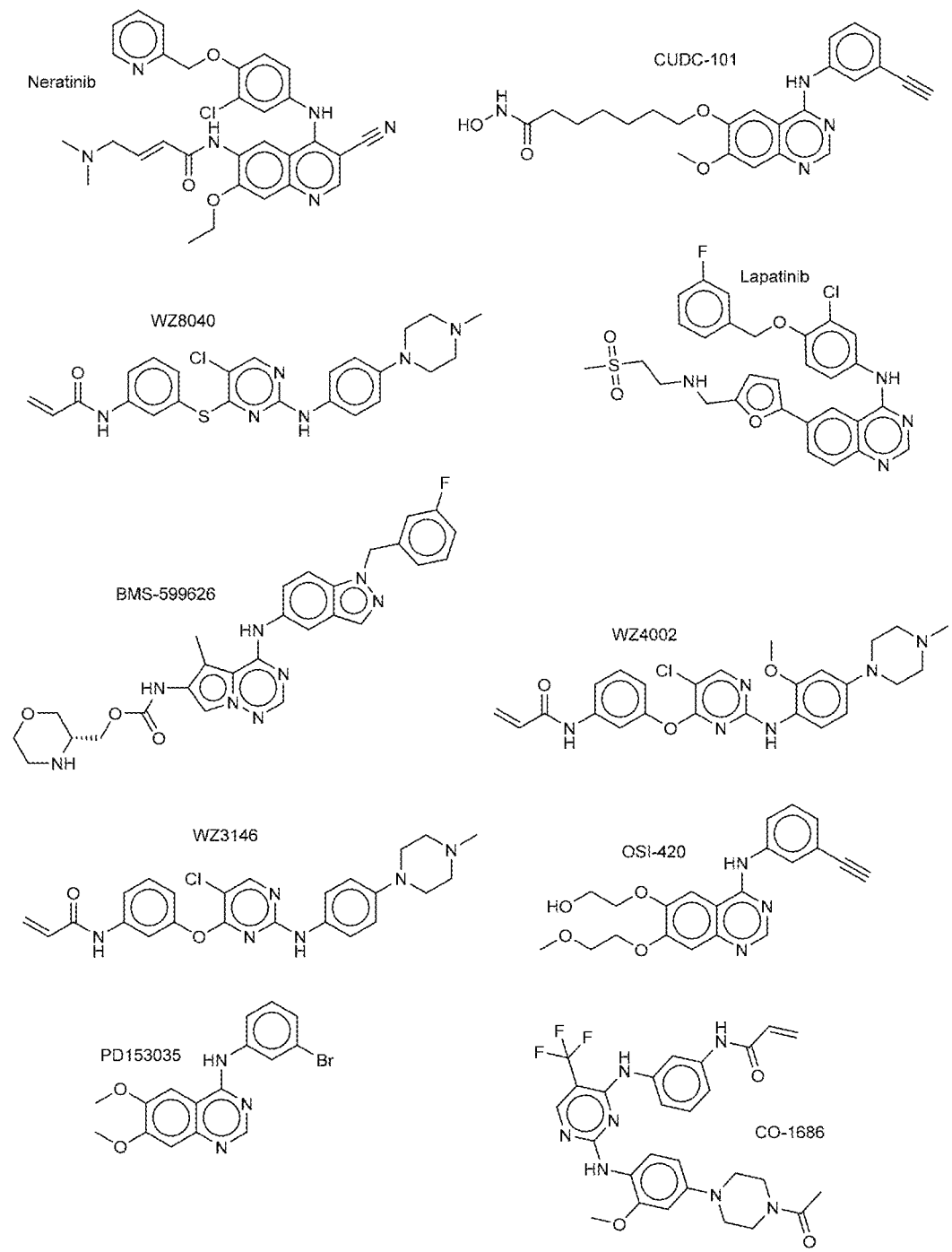
Figure 1C:
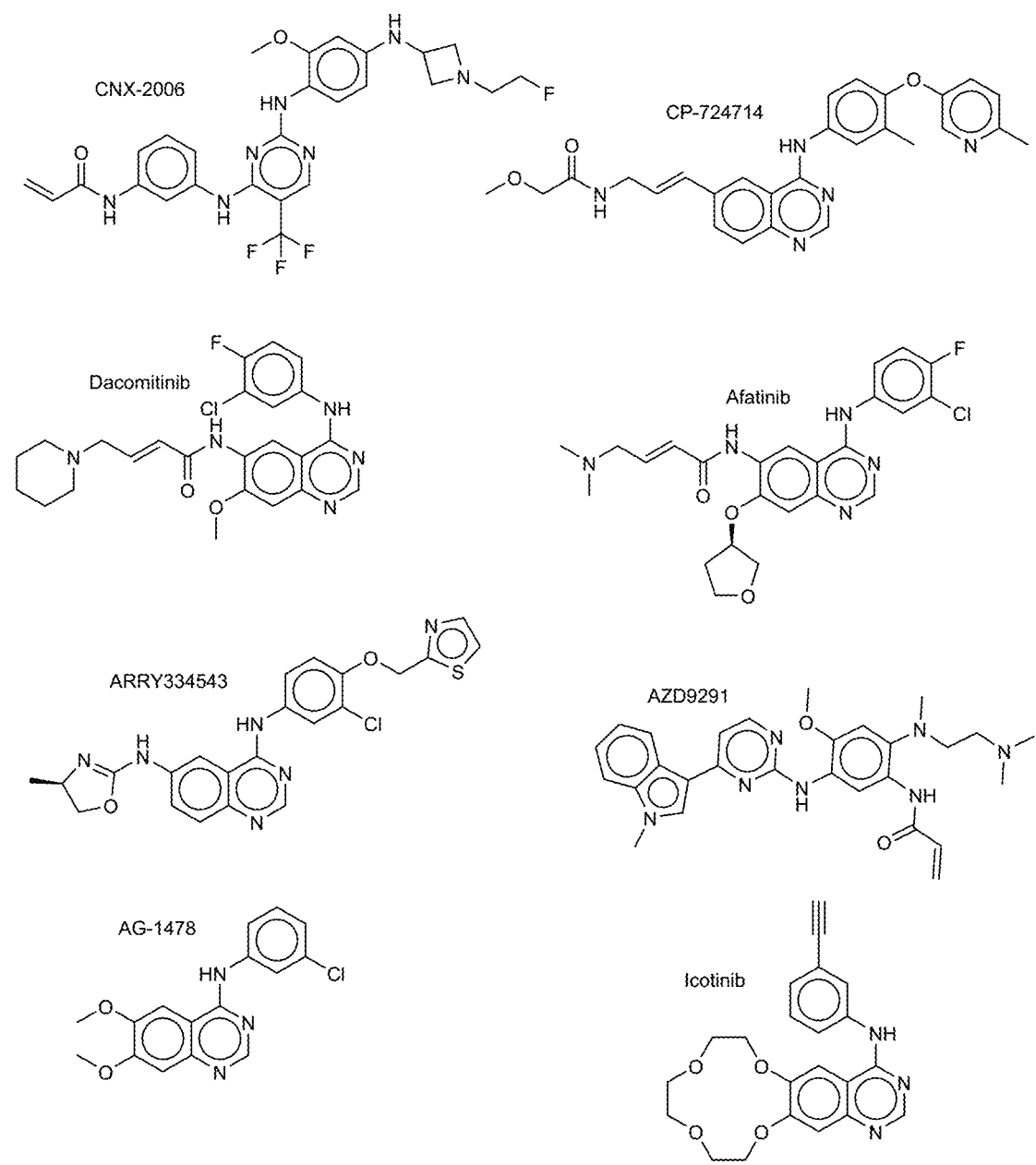
Figure 2A:
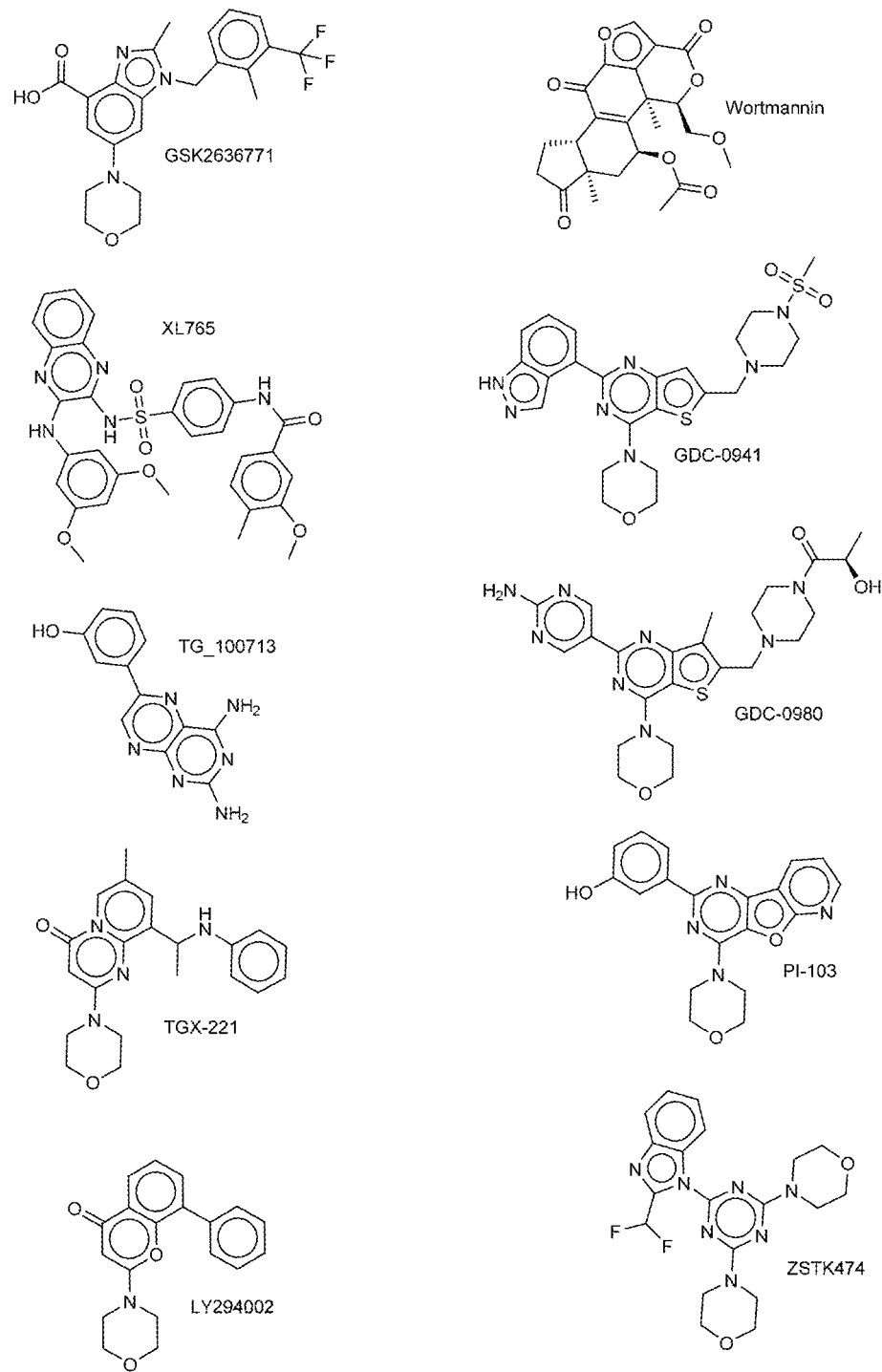
FIG. 2A-E shows PI3K inhibiting agents.
Figure 2B:
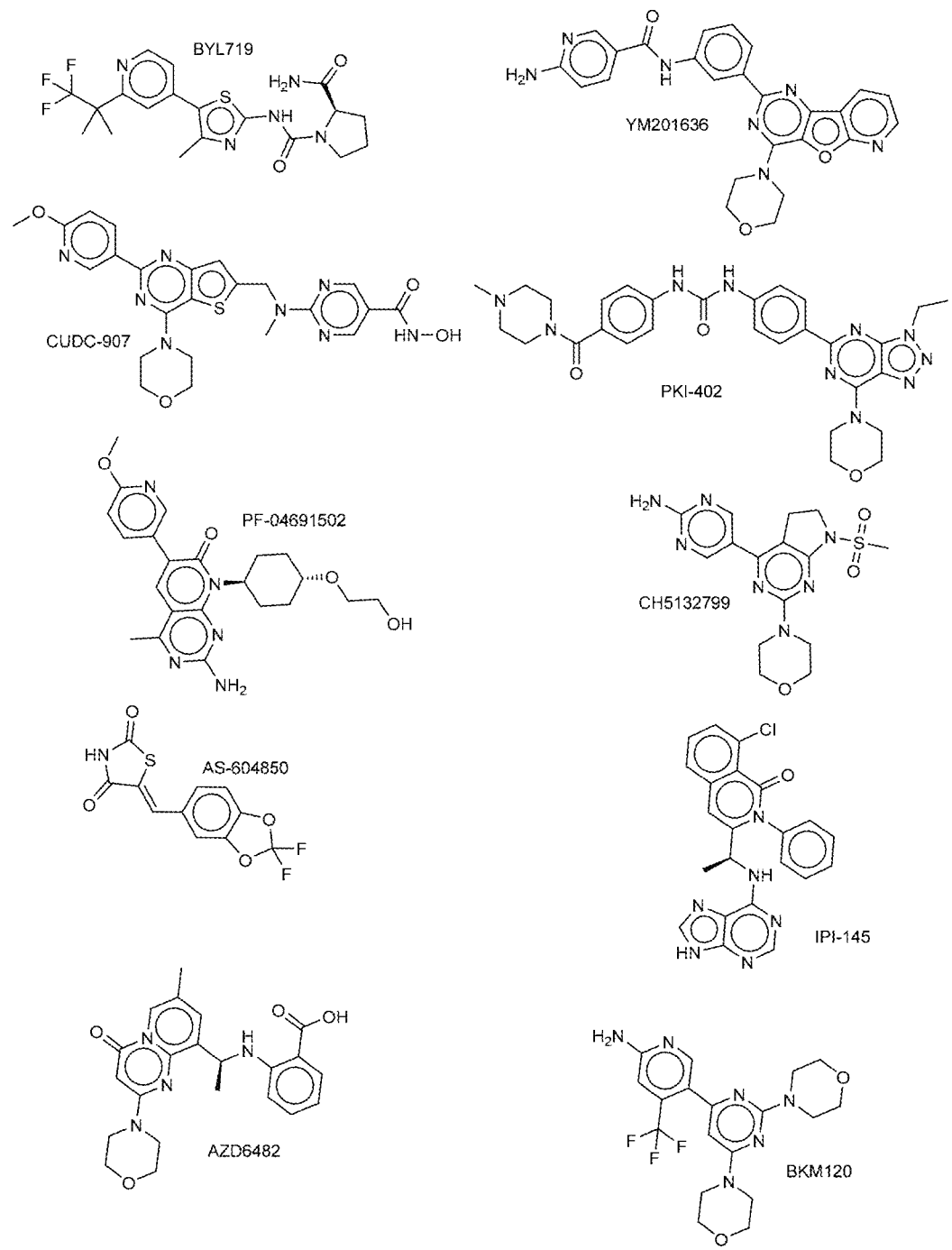
Figure 2C:
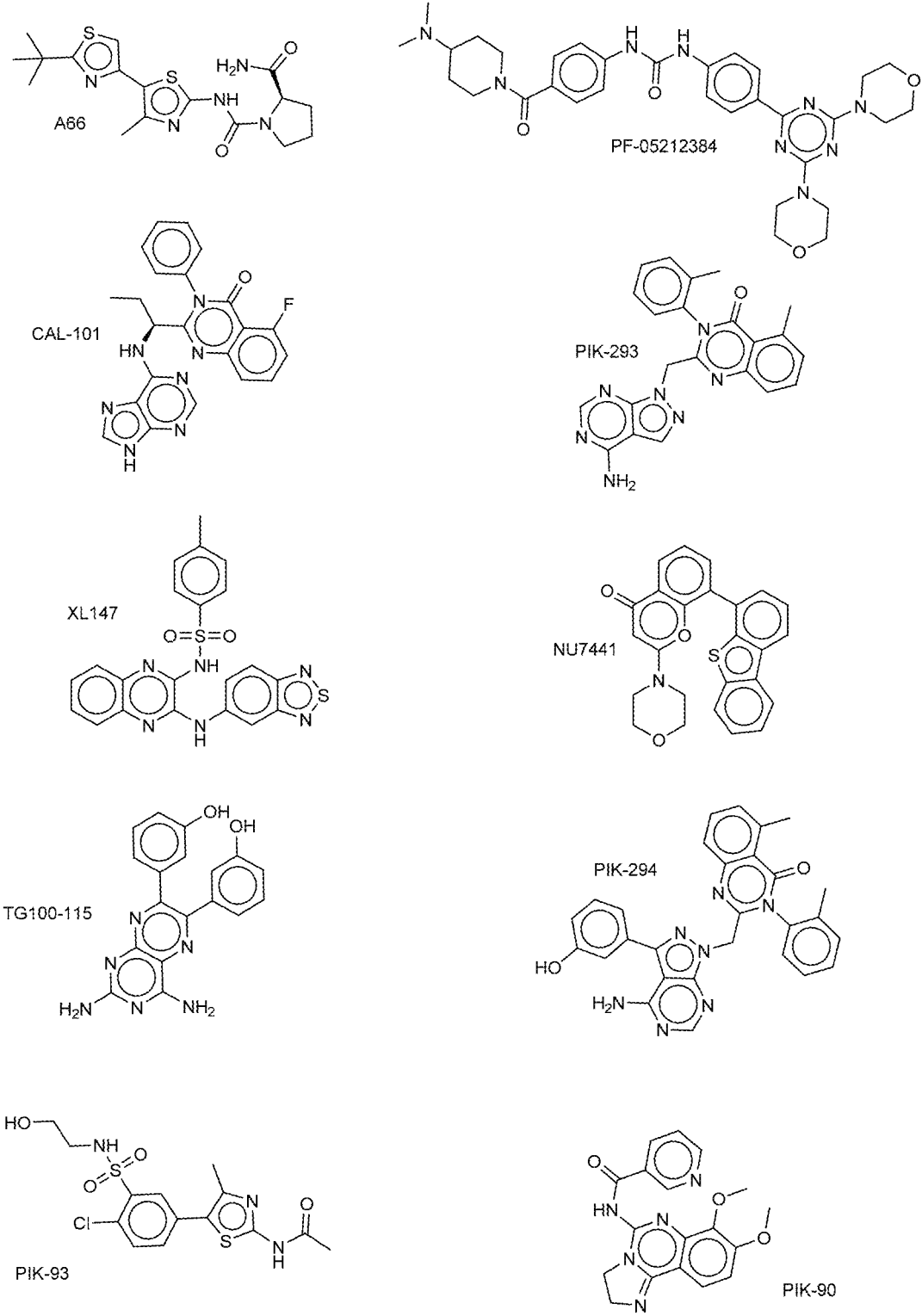
Figure 2D:
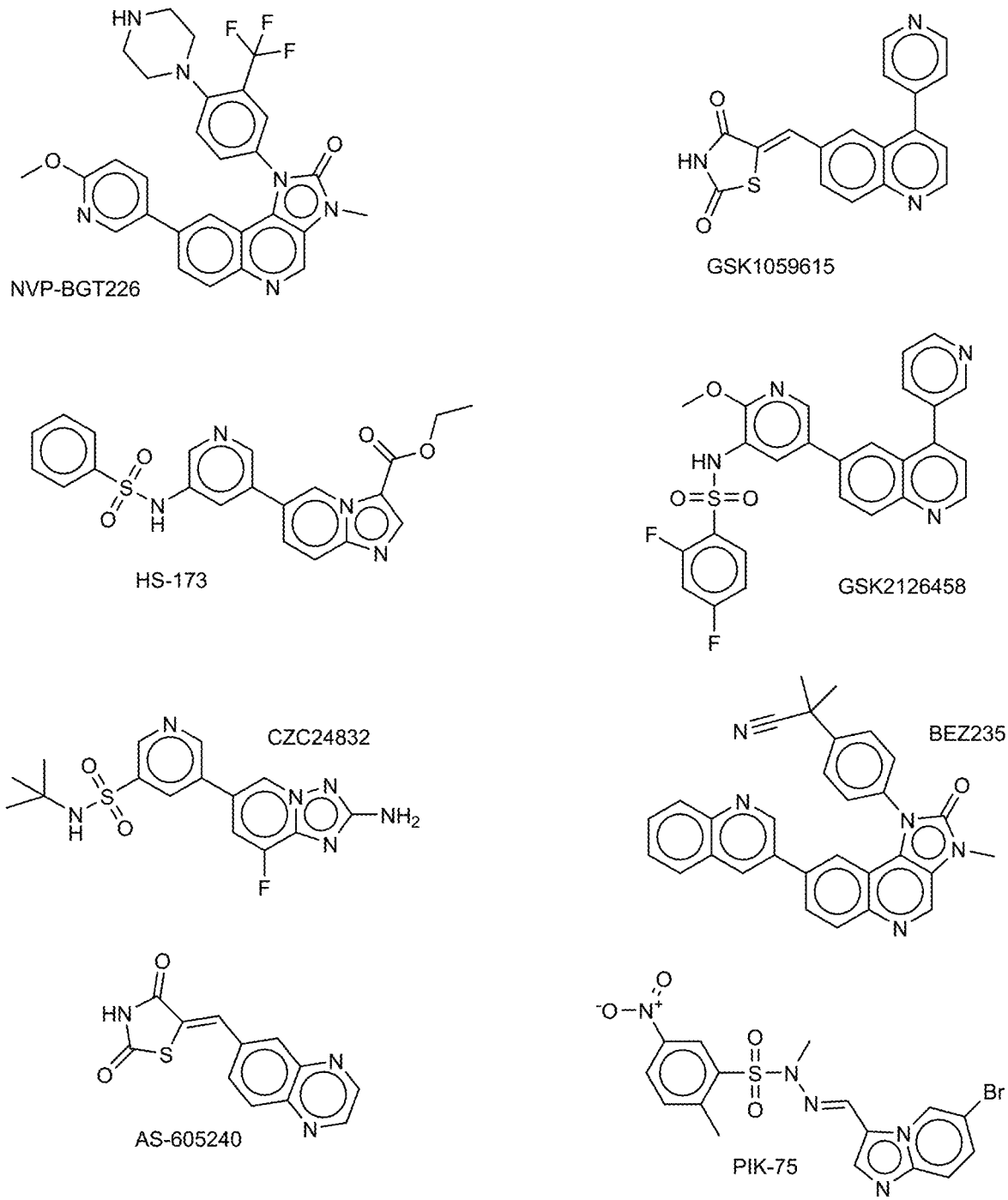
Figure 2E:
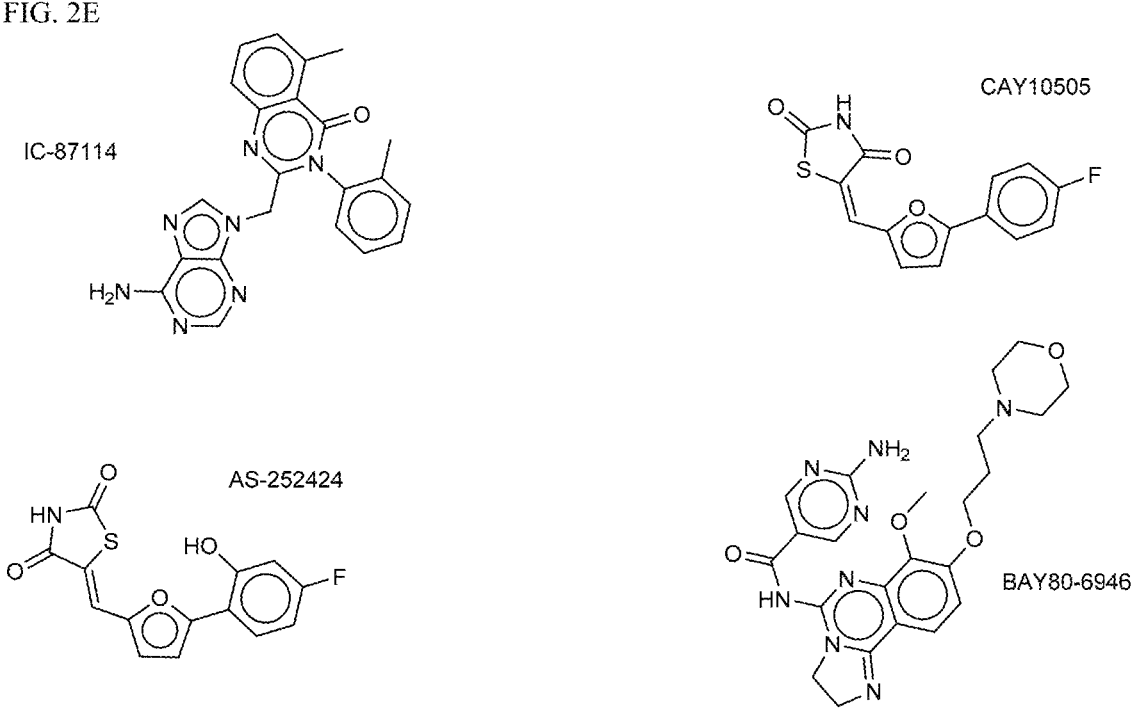

Utilizing x-ray crystal structure and structure-activity relationships gleaned from compound databases, a compiled database of all curated literature EGFR inhibiting agents (FIG. 1A-C) and PI3K inhibiting agents (FIG. 2A-E) was generated.

Next, "active cores" for each target were separately generated and such cores compared with high activity against both kinases. Such cores were cross-checked for selectivity. Three 'selective' cores were identified. X-ray crystal structures of the active and selective cores were analyzed for binding modes.

FIG. 3 shows the X-ray Crystal quinolone binding mode in EGFR (ATP competitive site of protein kinases) for Lapatinib (PDB Code: 1XKK) and HKI-272 (PDB Code: 3W2Q). For Lapatinib, the quinoline nitrogen forms hydrogen bond with hinge backbone MET793. The 6 position of quinazoline ring system is out towards solvent which is flipped relative to the PI3K binding mode of quinoline. For HKI-272 (quinoline with 3-nitrile) a similar binding mode as the quinazoline core is maintained, but flipped when compared to PI3K binding mode. SAR between the two series is anticipated to be convergent.

Figure 4A:
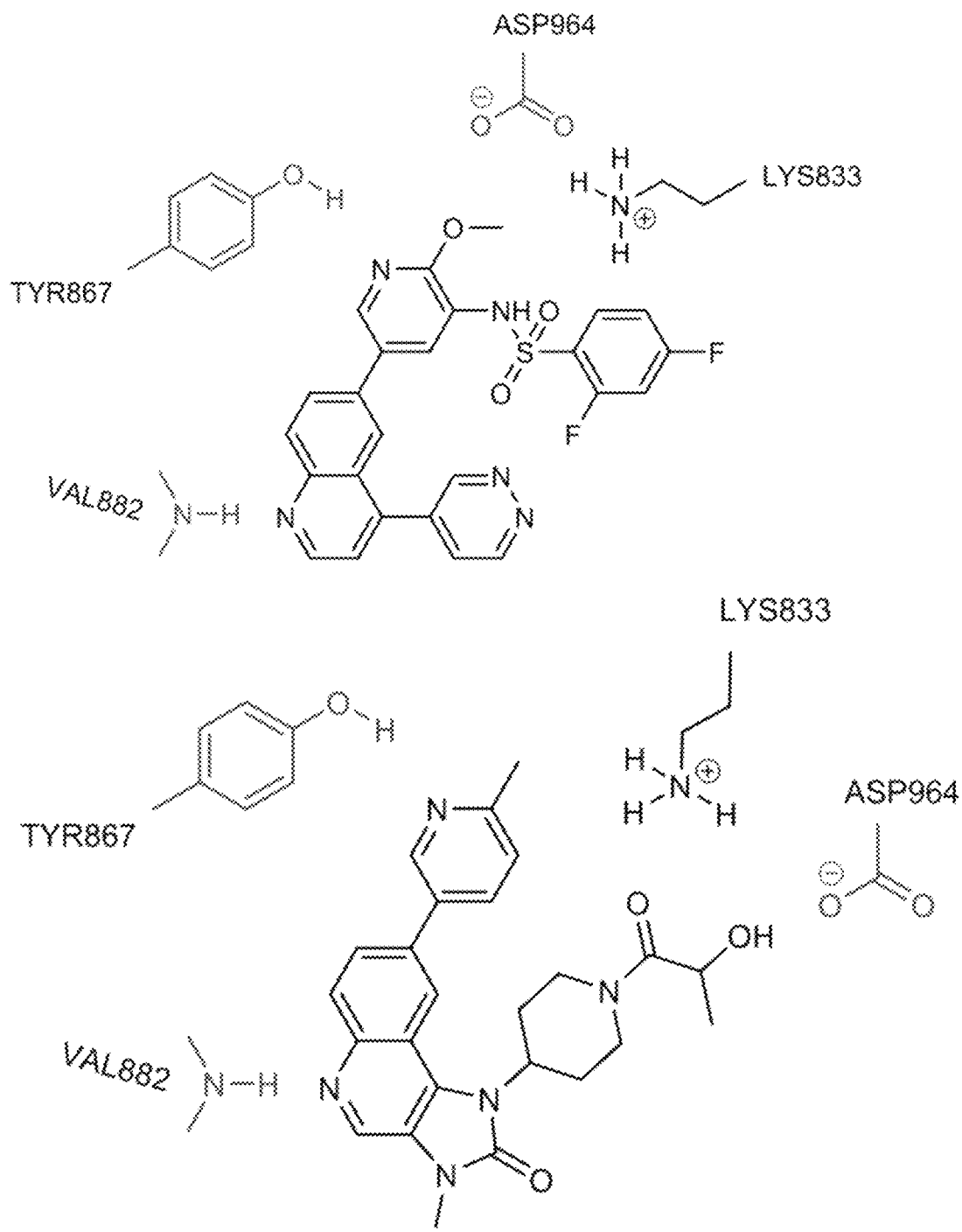
FIG. 4A shows the X-ray crystal binding mode of GSK2126458 (PDB Code: 3L08) with EGFR and PI3K, the X-ray crystal binding mode of PF-04979064 (PDB Code: 4HVB) with PI3K, and the X-ray crystal binding mode of Lapatinib with EGFR.
Figure 4A:
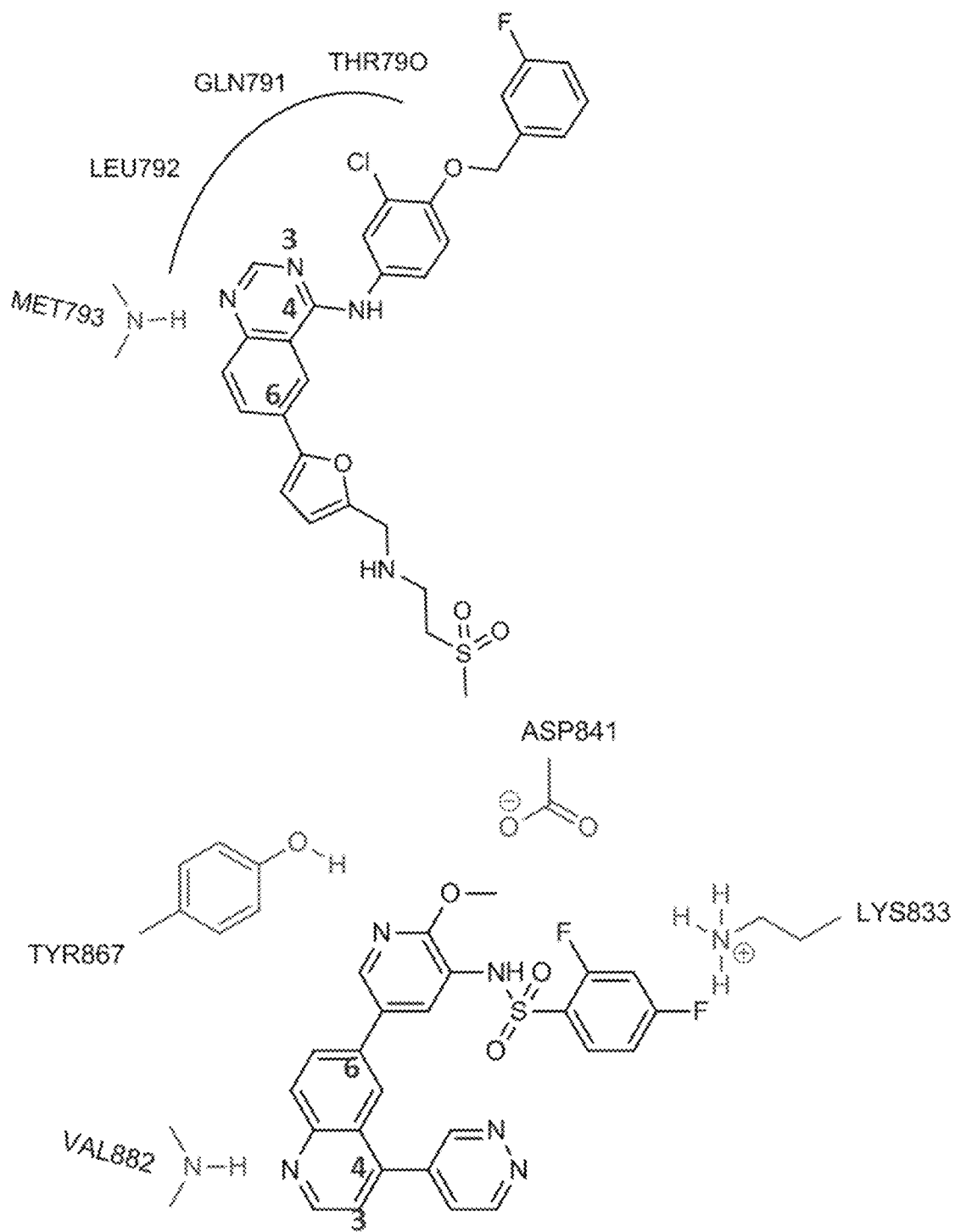

FIG. 4A shows the X-ray crystal binding mode of GSK2126458 (PDB Code: 3L08) with EGFR and PI3K, the X-ray crystal binding mode of PF-04979064 (PDB Code: 4HVB) with PI3K, and the X-ray crystal binding mode of Lapatinib with EGFR. As shown, the X-ray Crystal Structure of GSK2126458 (3L08) binding to PI3K quinoline nitrogen forms hydrogen bond with hinge backbone valine. The pyridyl off the 6 position sits within the PI3K specificity pocket. The sulfonamide interacts with LYS833 and aromatic groups sits within the phosphate binding pocket.

Figure 4B:
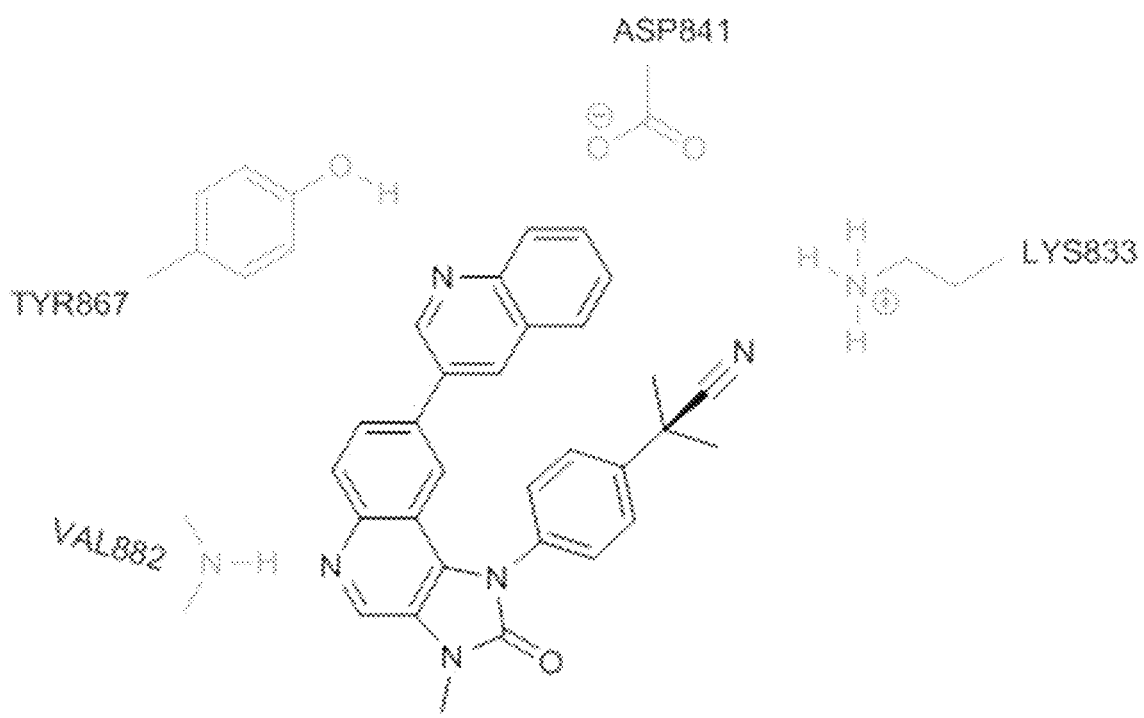
FIG. 4B shows the binding mode of BEZ235 in PI3K.

FIG. 4B shows the binding mode of BEZ235 in PI3K. The model of BEZ235 binding in PI3K quinoline nitrogen forms hydrogen bond with hinge backbone valine. The second quinoline off the 6 position sits within the PI3K specificity pocket. The nitrile interacts with LYS833 and aromatic groups is bridge between ribose binding pocket and phosophate binging pocket.

Figure 4C:
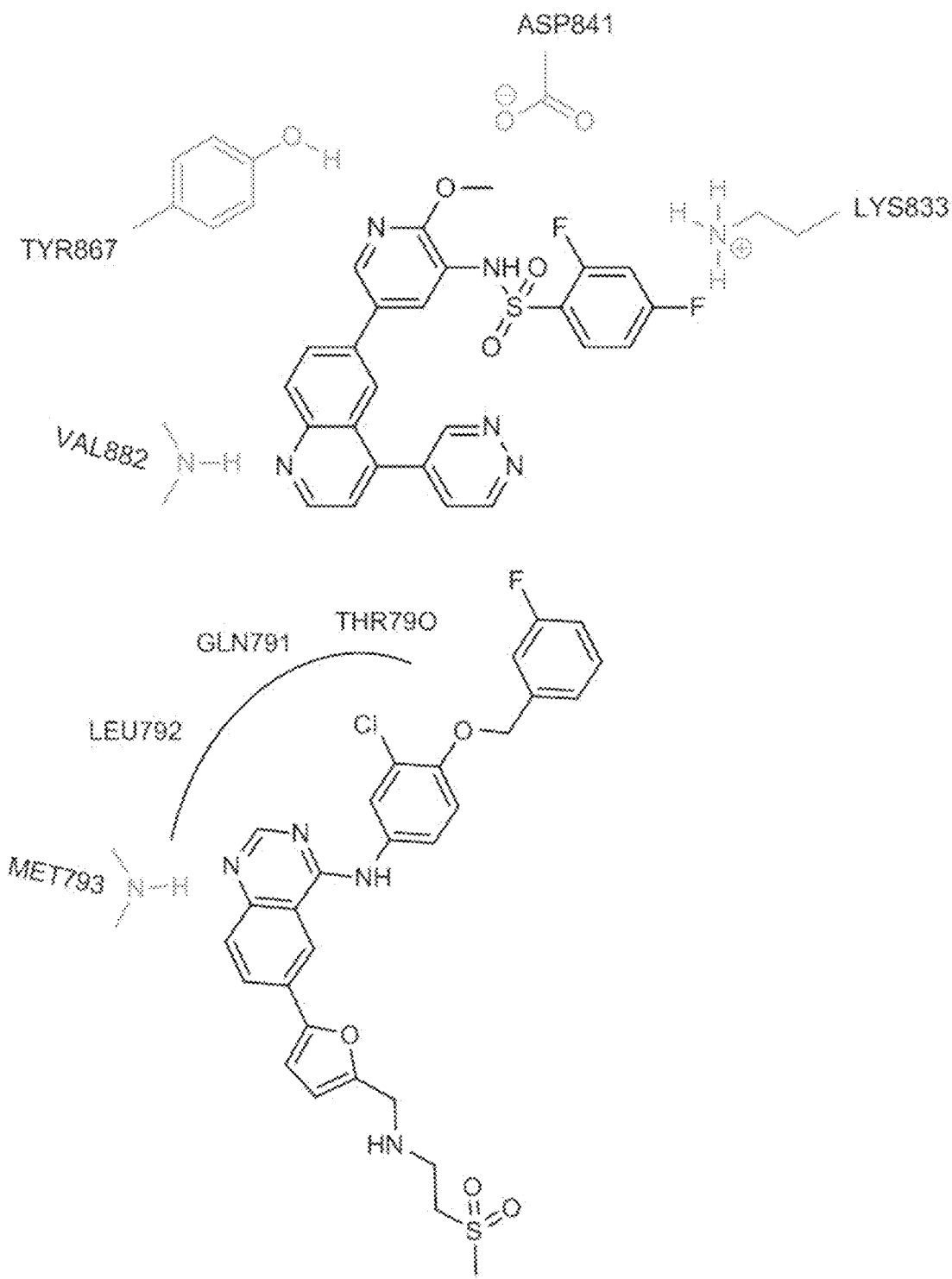
FIG. 4C shows a comparison of lipid versus protein kinase binding mode of quinoline for Lapatinib and GSK2126458 (PDB Code: 3L08).

FIG. 4C shows a comparison of lipid versus protein kinase binding mode of quinoline for Lapatinib and GSK2126458 (PDB Code: 3L08). As shown, the binding mode of quinoline (quinazoline) core is flipped in PI3K versus EGFR.

Based upon such binding information, new compounds were synthesized for dual potency against PI3K and EGFR. Common core

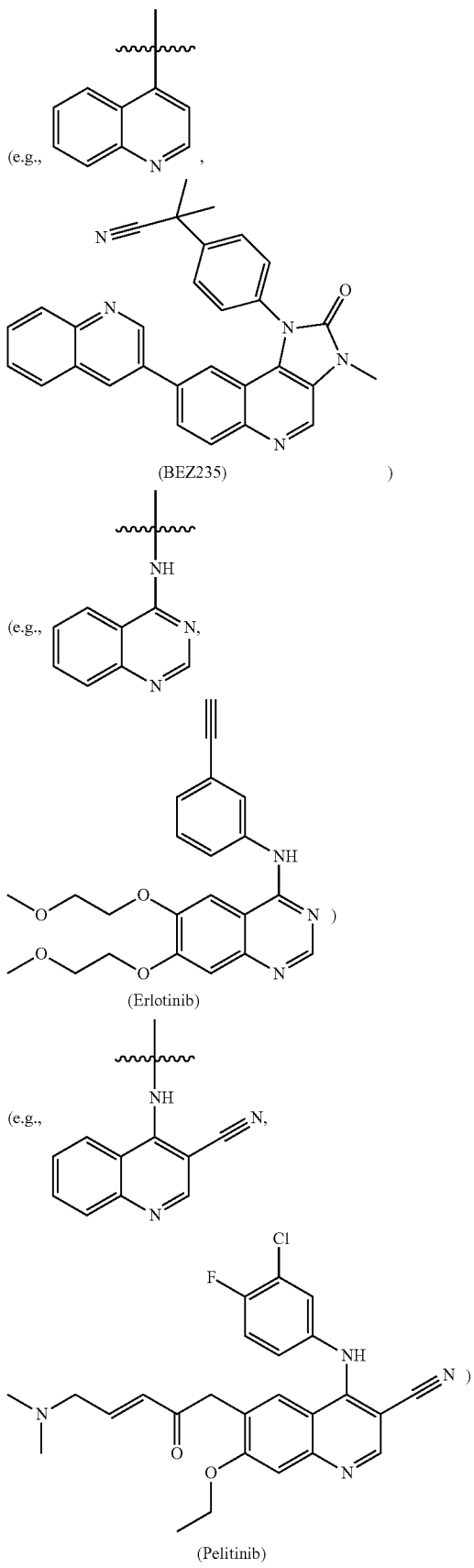

were selected and ligands were designed for potency against EGFR and PIK3CA. The respective core portions of the molecules display structural motifs of common core structures that have activity against PIK3CA or EGFR. These common cores served as the basis for designing new molecules with potential activity against both EGFR and PI3K. Such cores were utilized with known binding modes of molecules in their respective active sites of EGFR and PI3K resulting in the designing of novel ligands with activity against both (see, FIG. 4C).

Numerous hits were designed with nanaomolar potency against EGFR and PIK3CA.

Unexpectedly, when the molecules were profiled against a broad panel of 39 kinases, encompassing a diverse array of tyrosine, serine/threonine and lipid kinases, only the ERBB (ERBB1, ERBB2 and ERBB4) and PI3K (PIK3alpha, P110 gamma, P110 delta, MTOR and DNA-PK) families were uniformly inhibited by >50% at 10 µM. Representative data for MOL-162 demonstrated potent dual inhibition of purified EGFR and PIK3CA accompanied by cellular modulation of both pathways and cytotoxicity against KRAS mutant HCT-116 cells. A structure-activity relationship was shown for these agents against both of the biochemical targets. Furthermore, selectivity was demonstrated against other HER family members as well as MTOR. Based on such results against PI3K family members, it is anticipated that such compounds will be equally potent against other isoforms of PI3K beyond PIK3CA, therefore expanding therapeutic utility beyond colorectal cancer.

The clean kinase profile of MOL-153 led to evaluation of this compound for in vivo pharmacodynamic activity against subcutaneous HCT-116 tumors. While intraperitoneal administration of 100 mg/kg of this compound resulted in inhibition of pAKT, inhibition of pEGFR was not detected, presumably due to insufficient potency against EGFR (349 nM). Closely related analogs were next synthesized that would possess improved dual potency against both primary targets and also exhibit oral activity. MOL-162, which is significantly more soluble than MOL-153, emerged from these efforts. As shown in FIG. 5A, phosphorylation of EGFR was found to be completely suppressed in HCT-116 tumors (100 mg/kg) at two hours post-dosing of a single oral dose of MOL-162. Phosphorylation of AKT was not as strongly inhibited. However, additional synthesis of MOL-162 is needed to allow a full pharmacodynamic time course study to be carried out to determine the maximal degree of target inhibition of both targets after single and repeated daily dosing.

FIG. 5B shows a measurement of cell proliferation for MOL-160, MOL-161, MOL-162, and MOL-163. Cell proliferation was determined using the Cell Titer Glo assay (Promega, Madison, Wis.). Cell lines were seeded at a density between 2,000 and 5,000 cells per well in a 96-well plate. Twenty four hours after plating, cells were dosed with varying concentrations of drug, either as a single agent or in combination. The signal for Cell Titer Glo was determined 72 or 96 hours after dosing.

FIG. 5C shows HCT-116 cell viability for various compounds.

Figure 5D:
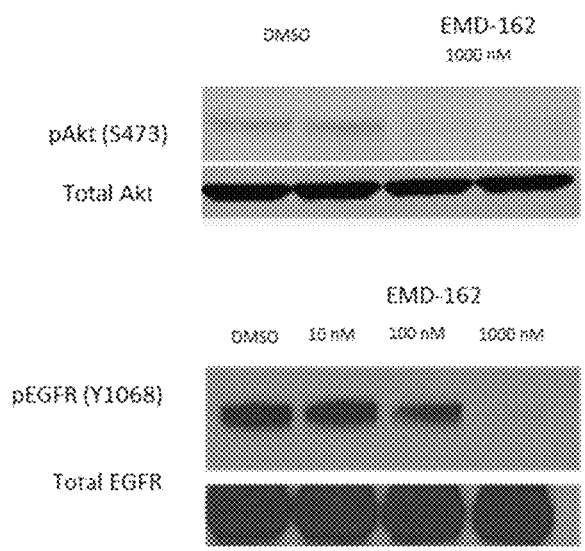
FIG. 5D shows the effect of MOL-162 on pAKT and pEGFR in HCT-116 cells treated for two hours.

FIG. 5D shows the effect of MOL-162 on pAKT and pEGFR in HCT-116 cells treated for two hours.

FIG. 6 shows IC50s of various compounds against EGFR and PIK3CA. Various compounds were tested for their ability to inhibit EGFR and PIK3CA. The assays determining inhibitions are given in Example 2 Assays—Z'-LYTE® and ADAPTA.

Figure 7:
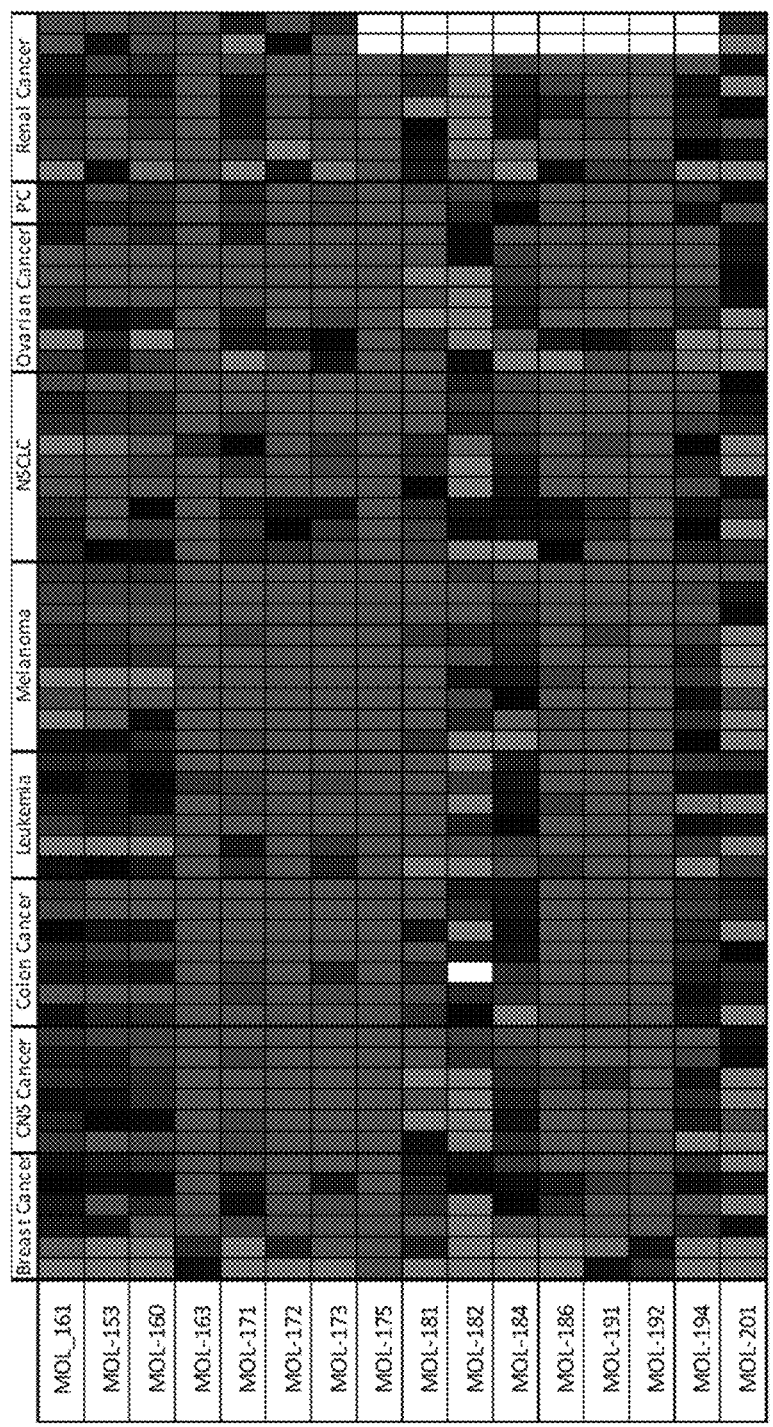
FIG. 7 shows % Growth of select compounds against NCI-60 Compare panel for compounds at 10 μM.
Figure 8A:
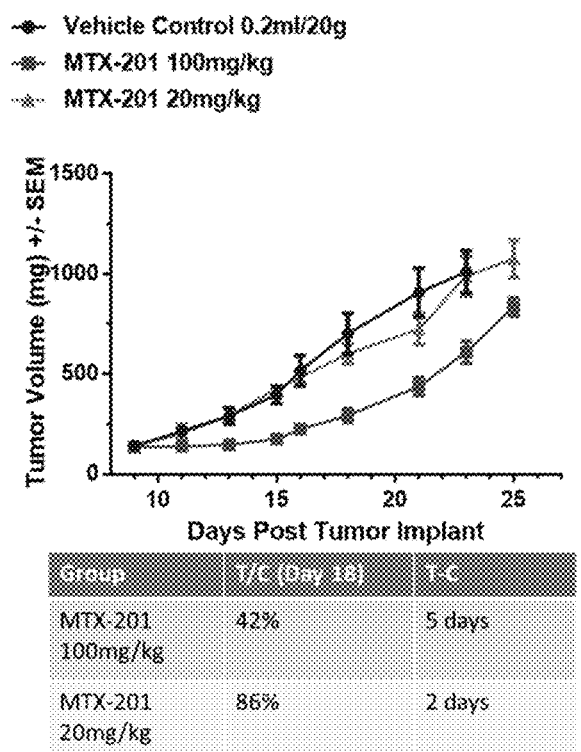
FIGS. 8A, 8B, 8C, 8D, and 8E shows in vivo efficacy of MOL-201 against, HCT-116, A431, COL-205, SK-MELS and MDA-MB-468 xenografts.
Figure 8B:
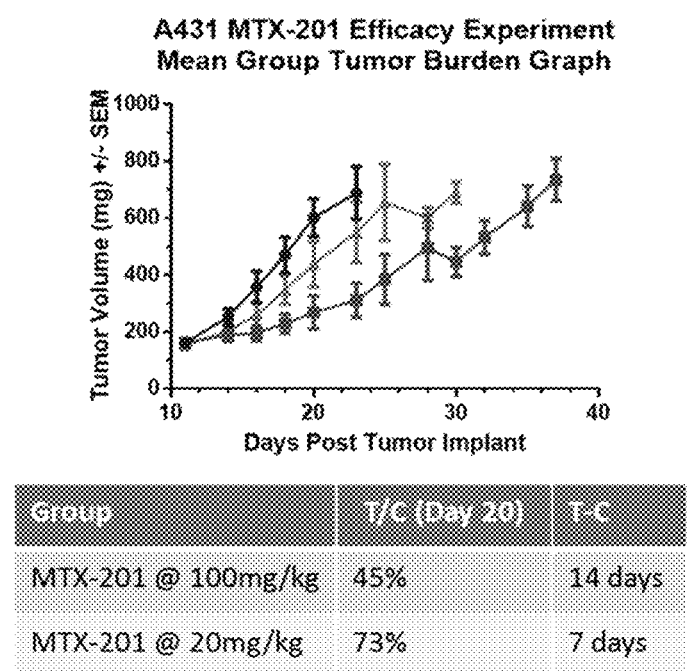
Figure 8C:
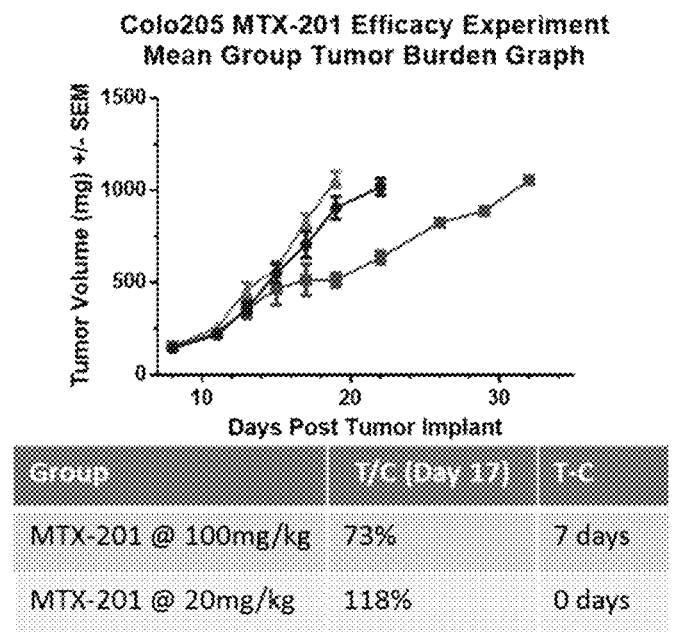
Figure 8D:
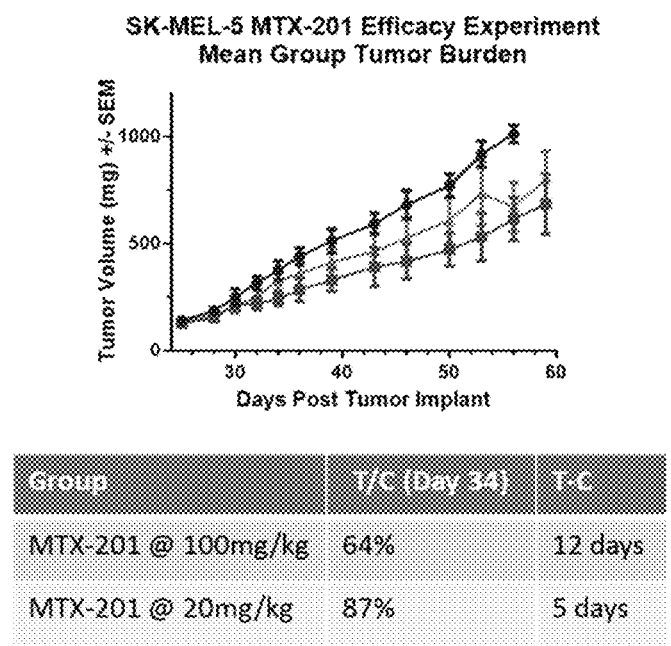
Figure 8E:
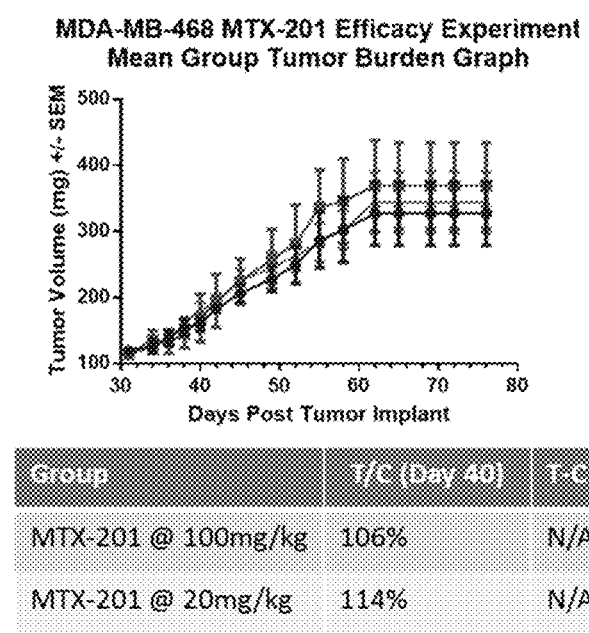

FIG. 7 shows % Growth of select compounds against NCI-60 Compare panel for compounds at 10 μM. Dual EGFR and PIK3CA inhibitors suppressed tumor growth of NCI-60 cell panel in vitro. MOL-201 demonstrated broad cell kill (negative growth at 10 uM) within the panel. The method is outlined in Example 2—NCI COMPARE Panel.

FIGS. 8A, 8B, 8C, 8D, and 8E show in vivo efficacy of MOL-201 against, HCT-116, A431, COL-205, SK-MELS and MDA-MB-468 xenografts. MOL-201 was well tolerated by mice with no clinical observations of toxicity treated daily for 10 days at 20 and 100 mg/kg.

Anti-tumor activity observed at higher dose in HCT-116, A431, SK-MELS and COL-205 xenografts as indicated by T/C and T-C values. MOL-201 elicited anti-tumor activity at lower dose of 20 mg/kg. The method is outlined in Example 2—Xenograft Studies.

Example 2

The materials and methods for Example 1 are described.

Assays: The Z'-LYTE® biochemical assay employs a fluorescence-based, coupled-enzyme format and is based on the differential sensitivity of phosphorylated and non-phosphorylated peptides to proteolytic cleavage (FIG. 6). The peptide substrate is labeled with two fluorophores—one at each end—that make up a FRET pair. In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress.

A significant benefit of this ratiometric method for quantitating reaction progress is the elimination of well-to-well variations in FRET-peptide concentration and signal intensities. As a result, the assay yields very high Z'-factor values (>0.7) at a low percent phosphorylation.

Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

Enzyme: The ADAPTA universal kinase assay is a homogenous, fluorescent based immunoassay for the detection of ADP. In contrast to ATP depletion assays, the ADAPTA assay is extremely sensitive to ADP formation such that a majority of the signal change occurs in the first 10-20% conversion of ATP to ADP. This makes the ADAPTA universal kinase assay ideally suited for use with low activity kinases.

The principle of the ADAPTA universal kinase assay is outlined below. The assay itself can be divided into two phases: a kinase reaction phase, and an ADP detection phase. In the kinase reaction phase, all components required for the kinase reaction are added to the well, and the reaction is allowed to incubate for 60 minutes. After the reaction, a detection solution consisting of a europium labeled anti-ADP antibody, an Alexa Fluor® 647 labeled ADP tracer, and EDTA (to stop the kinase reaction) is added to the assay well. ADP formed by the kinase reaction (in the absence of an inhibitor) will displace the Alexa Fluor® 647 labeled ADP tracer from the antibody, resulting in a decrease in the TR-FRET signal. In the presence of an inhibitor, the amount of ADP formed by the kinase reaction is reduced, and the resulting intact antibody-tracer interaction results in a high TR-FRET signal.

Z'-LYTE® Assay Conditions:
Test Compounds The Test Compounds are screened in 1% DMSO (final) in the well. For 10 point titrations, 3-fold serial dilutions are conducted from the starting concentration of the customer's choosing.
Peptide/Kinase Mixtures All Peptide/Kinase Mixtures are diluted to a 2× working concentration in the appropriate Kinase Buffer.
ATP Solution All ATP Solutions are diluted to a 4× working concentration in Kinase Buffer (50 mM HEPES pH 7.5, 0.01% BRIJ-35, 10 mM MgCl2, 1 mM EGTA). ATP Km apparent is previously determined using a Z'-LYTE® assay.
Development Reagent Solution The Development Reagent is diluted in Development Buffer.
10× Novel PKC Lipid Mix: 2 mg/ml Phosphatidyl Serine, 0.2 mg/ml DAG in 20 mM HEPES, pH 7.4, 0.3% CHAPS. For 5 mL 10× Novel PKC Lipid Mix: 1. Add 10 mgs Phosphatidyl Serine (Avanti Polar Lipids Part #8400032C or 840039C) and 1 mg DAG (Avanti Polar Lipids Part #800811C) to a glass tube. 2. Remove the chloroform from lipid mixture by evaporating to a clear, thin film under a stream of nitrogen. Continuous rotation of the tube, at an angle to ensure maximum surface area of the lipid solution, will promote the thinnest film. 3. Add 5 mLs resuspension buffer, 20 mM HEPES, 0.3% CHAPS, pH 7.4, to the dried lipid mix 4. Heat gently to 50-60° C. for 1-2 minutes and vortex in short intervals until the lipids are dissolved to a clear or slightly hazy solution. The lipids are typically in solution after 2-3 heat/vortex cycles. 5. Cool to room temperature, aliquot into single use volumes and store at −20° C.
Assay Protocol: Bar-coded Corning, low volume NBS, black 384-well plate (Corning Cat. #4514) 1. 2.5 μL-4× Test Compound or 100 nL 100× plus 2.4 μL kinase buffer. 2. 5 μL-2× Peptide/Kinase Mixture. 3. 2.5 μL-4×ATP Solution. 4. 30-second plate shake. 5. 60-minute Kinase Reaction incubation at room temperature. 6. 5 μL-Development Reagent Solution. 7. 30-second plate shake. 8. 60-minute Development Reaction incubation at room temperature. 9. Read on fluorescence plate reader and analyze the data.

ADP formation is determined by calculating the emission ratio from the assay well. The emission ratio is calculated by dividing the intensity of the tracer (acceptor) emission by the intensity of the Eu (donor) emission at 615 nm as shown in the equation below.

Since the ADAPTA technology measures ADP formation (i.e. conversion of ATP to ADP) it can be used to measure any type of ATP hydrolysis, including intrinsic ATPase activity of kinases. In this case, the substrate is water, not a lipid or peptide. The SelectScreen® service screens CHUK in this way, so a substrate is not included in the kinase reaction. A reference for using intrinsic ATPase activity to screen for kinase inhibitors is provided below.
Adapta® Assay Conditions'
Test Compounds: The Test Compounds are screened in 1% DMSO (final) in the well. For 10 point titrations, 3-fold serial dilutions are conducted from the starting concentration of the customer's choosing.

Substrate/Kinase Mixtures: All Substrate/Kinase Mixtures are diluted to a 2× working concentration in the appropriate Kinase Buffer (see section Kinase Specific Assay Conditions for a complete description).

ATP Solution: All ATP Solutions are diluted to a 4× working concentration in water. ATP Km apparent is previously determined using a radiometric assay except when no substrate is available in which case an Adapta® assay is conducted.

Detection Mix: The Detection Mix is prepared in TR-FRET Dilution Buffer. The Detection mix consists of EDTA (30 mM), Eu-anti-ADP antibody (6 nM) and ADP tracer. The detection mix contains the EC60 concentration of tracer for 5-150 μM ATP.

Assay Protocol: Bar-coded Corning, low volume, white 384-well plate (Corning Cat. #4512)1. 2.5 μL-4× Test Compound in 30 mM HEPES or 100 nL 100× in 100% DMSO plus 2.4 μL 30 mM HEPES. 2. 2.5 μL-4×ATP Solution. 3. 5 μL-2× Substrate/Kinase Mixture. 4. 30-second plate shake. 5. 1-minute centrifuge at 1000× g. 6. 60-minute Kinase Reaction incubation at room temperature. 7. 5 μL—Detection Mix. 8. 30-second plate shake. 9. 1-minute centrifuge at 1000×g. 10. 60-minute Detection Mix equilibration at room temperature. 11. Read on fluorescence plate reader and analyze the data.

Preparation of Protein Lysates and Western Blotting

[50 mmol/L Tris-HCl (pH 8.0), 150 mmol/L NaCl, 1% NP40, 0.5% Na-deoxycholate, 0.1% SDS, containing protease (P8340, Sigma, St. Louis, Mo.) and phosphatase (P5726, Sigma) inhibitor cocktails]. The soluble protein concentration was determined by micro-bovine serum albumin assay (Pierce, Rockford, Ill.). Protein immunodetection was done by electrophoretic transfer of SDS-PAGE separated proteins to nitrocellulose, incubation with antibody, and chemiluminescent second step detection (PicoWest, Pierce). The antibodies included EGFR, phospho-EGFR (Y1068), phospho-p42/p44, phospho-Akt (473), phospho-Akt (308), total Akt, phosho-S6 (235/236), and total S6. All antibodies were obtained from Cell Signaling Technologies (Danvers, Mass.).

Treatment Studies

For analysis of the effects of molecules disclosed herein on the phosphorylation of downstream signaling proteins, cell lines were grown to 70% confluence, at which time MOL-162 and/or similar compounds were added at the indicated concentration, and cells were incubated at 37 C for 1 or 2 hours. Where indicated, 10 ng/mL EGF ligand was added for 5 minutes. The medium was removed, cells were washed twice with PBS, and cells were lysed as previously described.

Western Blotting

Cell extracts were prepared by detergent lysis [25 mmol/L Tris-HCl (pH 7.6), 150 mmol/L NaCl, 1% Nonidet P-40, 10% glycerol, 1 mM EDTA, 1 mmol/L dithiothreitol (DTT), and protease and phosphatase inhibitors, rocked for 30 minutes at 4° C., and centrifuged at 14,000 rpm for 20 min at 4° C. Protein concentration was determined by BioRad Protein Assays and lysates were subsequently subjected to SDS gel electrophoresis. Proteins were transferred to polyvinylidene fluoride (PVDF) membranes and probed with primary antibodies recognizing EGFR, phospho-EGFR (Y1068), phospho-p42/p44, phospho-Akt (473), phospho-Akt (308), total Akt and GAPDH (Abcam). After incubation with either anti-rabbit HRP or anti-mouse HRP linked secondary antibody (Jackson ImmunoResearch Laboratories, Inc.), proteins were detected using chemiluminescence (GE Healthcare).

NCI COMPARE Panel.

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs. After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$$[(Ti-Tz)/(C-Tz)] \times 100 \text{ for concentrations for which } Ti >/= Tz$$

$$[(Ti-Tz)/Tz] \times 100 \text{ for concentrations for which } Ti < Tz.$$

The number reported for the One-dose assay is growth relative to the no-drug control, and relative to the time zero number of cells. This allows detection of both growth inhibition (values between 0 and 100) and lethality (values less than 0). For example, a value of 100 means no growth inhibition. A value of 40 would mean 60% growth inhibition. A value of 0 means no net growth over the course of the experiment. A value of −40 would mean 40% lethality. A value of −100 means all cells are dead. Information from the One-dose mean graph is available for COMPARE analysis. The heat map details green (% growth <0, % growth >0% but less than 50%, % growth >50%.

Xenograft Studies.

Female 6-7 week old NCR nude mice (CrTac:NCr-Foxn1nu from Taconic), 6-7 weeks old, were implanted subcutaneously with $1\times10^6$ to $1\times10^7$ cells in a 1:1 serum-free media/Matrigel® mixture into the region of the right axilla. Mice were randomized into treatment groups and treatments initiated when tumors reached 100 to 200 mg. MTX-201 was administered daily for 10 days by oral gavage as a clear yellow solution in 5% DMSO/95% PEG300, based upon individual animal body weight (0.2 ml/20 g). Subcutaneous tumor volume and body weights were measured two to three times a week. Tumor volumes were calculated by measuring two perpendicular diameters with calipers and using the formula: tumor volume=(length×width2)/2. Mice were held following cessation of treatment until tumor burdens reached ~1000 mg, to allow for calculation of tumor growth delay. Percent treated/control (% T/C) was calculated by dividing the median treated tumor weight by the median control tumor weight and multiplying by 100 on the last day of treatment. Tumor growth delay (T-C) was calculated by subtracting the median time to reach evaluation size (750 mg) of the treated group by the median time to evaluation size of the control group. A partial regression (PR) is defined as a tumor that regressed to <=50% of the baseline tumor volume. A complete response (CR) is defined as a tumor below the limits of palpation (<40 mg).

Example 3

This example shows the University of Michigan Quinazoline Library 3-Experimentals (Synthesis of MOL-160-163, and MOL-165).

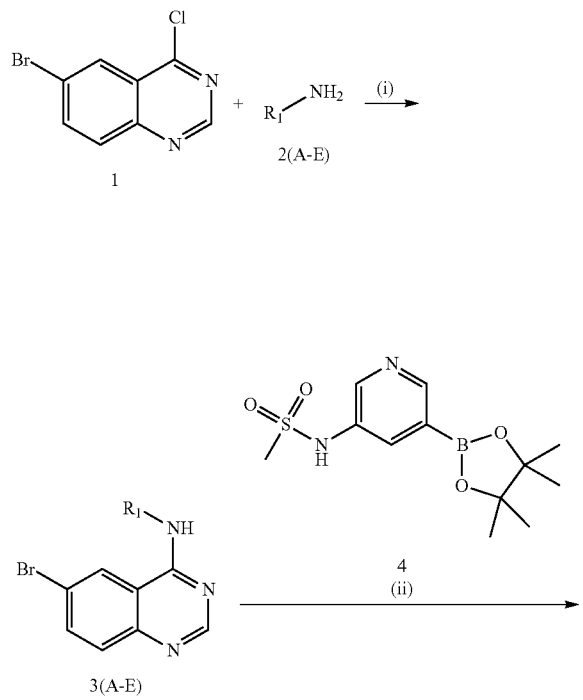

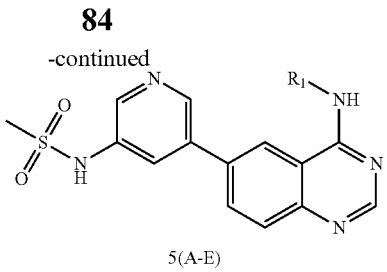

5(A-E)

Reaction conditions: (i) iPrOH, 80° C., overnight; (ii) SiliaCatDpp-Pd 5 mol %, 10% $K_2CO_3$, EtOH, 125° C., 5-60 min., µW
2A- 3-chloro-4-fluoroaniline
2B- 3-chloroaniline
2C- 3-amino-5-chloropyridine
2D- 3-bromoaniline
2E- 3-((trimethylsilyl)ethynyl)aniline N-(5-(4-((3-chloro-4-fluorophenyl)amino)quinazolin-6-yl)pyridin-3-yl)methanesulfonamide, MOL-160

To a solution consisting of 6-bromo-4-chloroquinazoline (0.3 g, 1.30 mmol) in 2-propanol (30 mL) was added 3-chloro-4-fluoroaniline (0.189 g, 1.30 mmol). The reaction mixture was heated (80° C.) and stirred overnight under a flow of $N_2$. The reaction mixture was cooled to room temperature and then the reaction mixture was filtered over a fritted funnel. The filtered solid was rinsed with excess 2-propanol and dried under high vacuum to afford 6-bromo-N-(3-chloro-4-fluorophenyl)quinazolin-4-amine (3A) as an off-white solid (350 mg, 85% yield). MS: (ESI+ m/z 353.9, ESI− m/z 351.9) A solution consisting of 6-bromo-N-(3-chloro-4-fluorophenyl)quinazolin-4-amine (0.185 g, 0.526 mmol) in anhydrous ethanol (3 mL) was placed in a 5 mL microwave reaction vial containing a stir bar. Next, 5-(methylsulfonamido)pyridine-3-yl boronic acid pinacol ester (4, 0.164 g, 0.553 mmol) was added followed by SiliCat DPP-Pd (5 mol %, 0.26 mmol/g loading, 0.101 g) and 10% aqueous potassium carbonate solution (2 equivalents, 0.76 mL, 1.05 mmol). The reaction mixture was placed under N2 atmosphere, capped, and then heated at 125° C. for one hour in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded N-(5-(4-((3-chloro-4-fluorophenyl)amino)quinazolin-6-yl)pyridin-3-yl)methanesulfonamide (5A, MOL-160, 96 mg, 41% yield, 96% purity) as a white solid; $^1$H NMR (400 MHz, DMSO-$d_6$) δ 10.17 (br. s, 1H), 10.03 (s, 1H), 8.83-8.87 (m, 2H), 8.66 (s, 1H), 8.49 (d, J=2.38 Hz, 1H), 8.13-8.20 (m, 2H), 7.90-7.98 (m, 2H), 7.83 (ddd, J=2.65, 4.25, 9.01 Hz, 1H), 7.47 (t, J=9.15 Hz, 1H), 3.14 (s, 3H); MS: (ESI+ m/z 444.1, ESI− m/z 442.0); TLC: (90:10:0.5, DCM:MeOH:NH4OH) $R_f$=0.32.

N-(5-(4-((3-chlorophenyl)amino)quinazolin-6-yl)pyridin-3-yl)methanesulfonamide, MOL-162

To a solution consisting of 6-bromo-4-chloroquinazoline (0.448 g, 1.84 mmol) in 2-propanol (10 mL) was added 3-chloroaniline (0.246 g, 1.93 mmol). The reaction mixture was heated (80° C.) and stirred overnight under a flow of $N_2$. The reaction mixture was cooled to room temperature and then the reaction mixture was filtered over a fritted funnel. The filtered solid was rinsed with excess 2-propanol and dried under high vacuum to afford 6-bromo-N-(3-chlorophenyl)quinazolin-4-amine (3B) as an off-white solid (490 mg, 79% yield, 98% purity). MS (ESI$^+$ m/z 335.9, ESI$^-$ m/z 333.9.) A solution consisting of 6-bromo-N-(3-chlorophenyl)quinazolin-4-amine (0.200 g, 0.597 mmol) in anhydrous ethanol (3 mL) was placed in a 5 mL microwave reaction vial containing a stir bar. Next, 5-(methylsulfonamido)pyridine-3-yl boronic acid pinacol ester (4, 0.187 g, 0.627 mmol) was added followed by SiliCat DPP-Pd (5 mol %, 0.26 mmol/g loading, 0.115 g) and 10% aqueous potassium carbonate solution (2 equivalents, 0.87 mL, 1.20 mmol). The reaction mixture was placed under N2 atmosphere, capped, and then heated at 100° C. for 30 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded N-(5-(4-((3-chlorophenyl)amino)quinazolin-6-yl)pyridin-3-yl)methanesulfonamide (5B, MOL-162, 78 mg, 31% yield, 97% purity) as a white solid; $^1$H NMR (400 MHz, DMSO-d$_6$) δ 10.20 (br.s., 1H), 10.04 (s, 1H), 8.89 (dd, J=1.74, 13.45 Hz, 1H), 8.70 (s, 1H), 8.50 (d, J=2.38 Hz, 1H), 8.19 (dd, J=1.65, 8.60 Hz, 1H), 8.11 (t, J=2.01 Hz, 1H), 7.91-8.04 (m, 1H), 7.67-7.91 (m, 1H), 7.45 (t, J=8.14 Hz, 1H), 7.22 (m, 1H), 3.16 (s, 3H); MS: (ESI$^+$ m/z 426.1, ESI$^-$ m/z 424.0); TLC: (90:10:0.5, DCM:MeOH:NH$_4$OH) R$_f$=0.49.

N-(5-(4-((5-chloropyridin-3-yl)amino)quinazolin-6-yl)pyridin-3-yl)methanesulfonamide, MOL-163

To a solution consisting of 6-bromo-4-chloroquinazoline (0.448 g, 1.84 mmol) in 2-propanol (10 mL) was added 3-amino-5-chloropyridine (0.248 g, 1.93 mmol). The reaction mixture was heated (80° C.) and stirred overnight under a flow of N$_2$. The reaction mixture was cooled to room temperature and then the reaction mixture was filtered over a fritted funnel. The filtered solid was rinsed with excess 2-propanol and dried under high vacuum to afford 6-bromo-N-(5-chloropyridin-3-yl)quinazolin-4-amine (3C) as an off-white solid (575 mg, 93% yield, 93% purity). MS (ESI$^+$ m/z 336.9, ESI$^-$ m/z 334.9). A solution consisting of 6-bromo-N-(5-chloropyridin-3-yl)quinazolin-4-amine (0.136 g, 0.405 mmol) in anhydrous ethanol (3 mL) was placed in a 5 mL microwave reaction vial containing a stir bar. Next, 5-(methylsulfonamido)pyridine-3-yl boronic acid pinacol ester (4, 0.127 g, 0.425 mmol) was added followed by SiliCat DPP-Pd (5 mol %, 0.26 mmol/g loading, 0.082 g) and 10% aqueous potassium carbonate solution (2 equivalents, 0.59 mL, 0.81 mmol). The reaction mixture was placed under N$_2$ atmosphere, capped, and then heated at 100° C. for 30 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded N-(5-(4-((5-chloropyridin-3-yl)amino)quinazolin-6-yl)pyridin-3-yl)methanesulfonamide (5C, MOL-163, 70 mg, 40% yield, 98% purity) as a white solid; $^1$H NMR (400 MHz, DMSO-d$_6$) δ 10.21 (br. s., 2H), 8.94-9.03 (m, 1H), 8.86-8.88 (d, J=4.65 Hz, 2H), 8.73 (s, 1H), 8.59 (s, 1H), 8.50 (d, J=2.01 Hz, 1H), 8.32-8.44 (m, 1H), 8.20 (d, J=8.97 Hz, 1H), 7.90-8.04 (m, 2H), 3.15 (s, 3H); MS: (ESI$^+$ m/z 427.0, ESI$^-$ m/z 425.0); TLC: (90:10:0.5, DCM:MeOH:NH$_4$OH) R$_f$=0.47.

N-(5-(4-((5-bromopyridin-3-yl)amino)quinazolin-6-yl)pyridin-3-yl)methanesulfonamide, MOL-165

To a solution consisting of 6-bromo-4-chloroquinazoline (0.448 g, 1.84 mmol) in 2-propanol (10 mL) was added 3-bromoaniline (0.332 g, 1.93 mmol). The reaction mixture was heated (80° C.) and stirred overnight under a flow of N$_2$. The reaction mixture was cooled to room temperature and then the reaction mixture was filtered over a fritted funnel. The filtered solid was rinsed with excess 2-propanol and dried under high vacuum to afford 6-bromo-N-(5-bromopyridin-3-yl)quinazolin-4-amine (3D) as an off-white solid (605 mg, 87% yield, 98% purity). MS (ESI$^+$ m/z 379.9, ESI$^-$ m/z 377.8). A solution consisting of 6-bromo-N-(5-bromopyridin-3-yl)quinazolin-4-amine (0.150 g, 0.395 mmol) in anhydrous ethanol (4 mL) was placed in a 5 mL microwave reaction vial containing a stir bar. Next, 5-(methylsulfonamido)pyridine-3-yl boronic acid pinacol ester (4, 0.120 g, 0.400 mmol) was added followed by SiliCat DPP-Pd (5 mol %, 0.26 mmol/g loading, 0.080 g) and 10% aqueous potassium carbonate solution (2 equivalents, 0.60 mL, 0.79 mmol). The reaction mixture was placed under N$_2$ atmosphere, capped, and then heated at 100° C. for 30 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded N-(5-(4-((5-bromopyridin-3-yl)amino)quinazolin-6-yl)pyridin-3-yl)methanesulfonamide (5D, MOL-165, 39 mg, 21% yield, 85% purity) as a white solid; This product is 85:15 mixture of 5D:5D-B N-(5'-((6-bromoquinazolin-4-yl)amino)-[3,3'-bipyridin]-5-yl)methanesulfonamide which occurs as by product from the Suzuki coupling reaction. $^1$H NMR (400 MHz, DMSO-d$_6$) δ 10.17 (br.s., 1H), 10.00 (s, 1H), 8.84-8.94 (m, 2H), 8.70 (s, 1H), 8.51 (d, J=2.38 Hz, 1H), 8.15-8.25 (m, 2H), 7.89-8.03 (m, 2H), 7.33-7.41 (m, 2H), 3.16 (s, 3H); MS: (ESI$^+$ m/z 470, 472); TLC: (90:10:0.5, DCM:MeOH:NH$_4$OH) R$_f$=0.62.

N-(5-(4-((3-ethynylphenyl)amino)quinazolin-6-yl)pyridin-3-yl)methanesulfonamide, MOL-161

To a solution consisting of 6-bromo-4-chloroquinazoline (1.2 g, 4.9 mmol) and 3-((trimethylsilyl)ethynyl)aniline (1.1 g, 5.9 mmol, prepared as describe by Ute F. Rohrig, J M C, 2012, 55(11), 5270-5290) in 30 mL of 1,4-dioxane was heated at 90° C. for 3 hour. The reaction mixture was cooled to room temperature, diluted with diethyl ether and filtered through fritted glass. The solid was triturated under 20 mL of isopropyl alcohol, filtered and dried to give 6-bromo-N-(3-((trimethylsilyl)ethynyl)phenyl)quinazolin-4-amine (3E) as a solid (940 mg, 48%); $^1$H NMR (400 MHz, DMSO-d$_6$) δ 11.8 (br s, 1H), 9.29 (d, J=1.7 Hz, 1H), 9.00 (s, 1H), 8.26 (dd, J=1.7, 8.8 Hz, 1H), 7.95 (d, J=8.9 Hz, 1H), 7.89 (s, 1H), 7.81 (d, J=8.1 Hz, 1H), 7.51 (t, J=7.9 Hz, 1H), 7.41 (d, J=7.7 Hz, 1H), 0.25 (s, 9H). A solution consisting of 6-bromo-N-(3-((trimethylsilyl)ethynyl)phenyl)quinazolin-4-amine (0.250 g, 0.631 mmol) in anhydrous ethanol (4 mL) was placed in a 5 mL microwave reaction vial containing a stir bar. Next, 5-(methylsulfonamido)pyridine-3-yl boronic acid pinacol ester (4, 0.200 g, 0.662 mmol) was added followed by SiliCat DPP-Pd (5 mol %, 0.26 mmol/g loading, 0.126 g) and 10% aqueous potassium carbonate solution (2 equivalents, 0.91 mL, 1.26 mmol). The reaction mixture was placed under N₂ atmosphere, capped, and then heated at 100° C. for 5 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 5-65% ethyl acetate in heptane, followed by 0-10% methanol in dichloromethane afforded a mixture of 5E with TMS-protected 5E. This mixture was dissolved in methanol and then treated with excess 10% potassium carbonate (1 mL). The solution was heated to 35° C. and the TMS removal was followed by TLC (90:10:0.5, DCM:MeOH:NH₄OH). After the reaction was complete, the solution was acidified (1N HCl) to pH~5 and then extracted three times with DCM:MeOH (90:10 mixture, 75 mL). The organic layer was concentrated under reduced pressure to afford the crude product. Purification of the deprotected crude product by Biotage Isolera flash chromatography using a gradient of 1-13% methanol in dichloromethane afforded N-(5-(4-((3-ethynylphenyl)amino)quinazolin-6-yl)pyridin-3-yl)methanesulfonamide (5E, MOL-161, 68 mg, 26% yield, 97.5% purity) as a yellow solid. $^1$H NMR (400 MHz, DMSO-d₆) δ 10.16 (br. s., 1H), 9.97 (s, 1H), 8.75-8.94 (m, 2H), 8.66 (s, 1H), 8.48 (d, J=2.38 Hz, 1H), 8.16 (dd, J=1.65, 8.60 Hz, 1H), 8.04 (s, 1H), 7.85-7.98 (m, 4H), 7.42 (t, J=7.87 Hz, 1H), 7.42 (d, J=7.69 Hz, 1H), 4.21 (s, 1H), 3.13 (s, 3H); MS: (ESI⁺ m/z 416.1, ESI⁻ m/z 414.0); TLC: (90:10:0.5, DCM:MeOH:NH₄OH) $R_f$=0.6.

Example 4

This example shows University of Michigan Quinazoline Experimentals (Synthesis of MOL-166-167, and MOL-153).

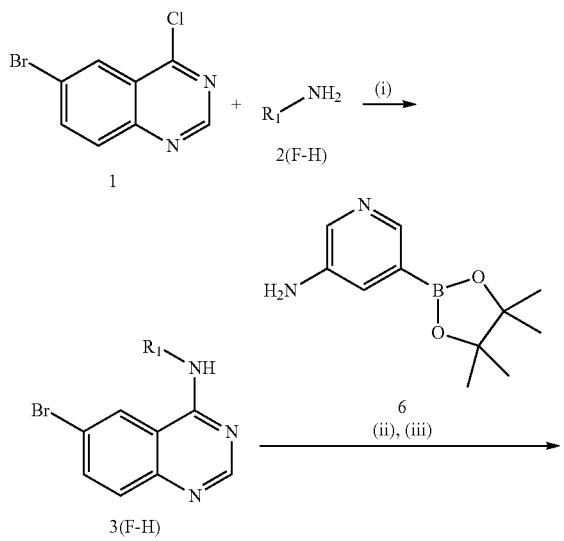

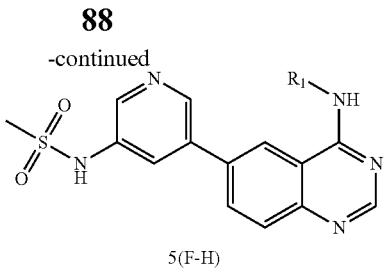

5(F-H)

Reaction conditions: (i) iPrOH, 80° C., overnight; (ii) SiliaCatDpp-Pd 5 mol %, 10% K₂CO₃, EtOH, 125° C., 5-60 min., μW; (iii) (7F-H),pyridine, methanesulfonyl chloride, rt, 15 minutes
2F- 4-(pyridin-4-yloxy)aniline
2G- benzylamine
2H- 3-chloro-4-methoxyaniline N-(5-(4-((4-(pyridin-4-yloxy)phenyl)amino)quinazolin-6-yl)pyridin-3-yl)methanesulfonamide, MOL-166

To a solution consisting of 6-bromo-4-chloroquinazoline (0.448 g, 1.84 mmol) in 2-propanol (10 mL) was added 4-(pyridine-4-yloxy)aniline (0.360 g, 1.93 mmol). The reaction mixture was heated (80° C.) and stirred overnight under a flow of N₂. The reaction mixture was cooled to room temperature and then the reaction mixture was filtered over a fritted funnel. The filtered solid was rinsed with excess 2-propanol and dried under high vacuum to afford 6-bromo-N-(4-(pyridin-4-yloxy)phenyl)quinazolin-4-amine (3F) as an off-white solid (313 mg, 43% yield, 97% purity). MS (ESI⁺ m/z 394.0, ESI⁻ m/z 392.0). Next a solution consisting of 6-bromo-N-(4-(pyridin-4-yloxy)phenyl)quinazolin-4-amine (0.306 g, 0.77 mmol) in anhydrous ethanol (10 mL) was placed in a 20 mL microwave reaction vial containing a stir bar. Next, 3-aminopyridine-5-boronic acid pinacol ester (6, 0.176 g, 0.80 mmol) was added followed by SiliCat DPP-Pd (5 mol %, 0.26 mmol/g loading, 0.150 g) and 10% aqueous potassium carbonate solution (2 equivalents, 1.15 mL, 1.6 mmol). The reaction mixture was placed under N₂ atmosphere, capped, and then heated at 125° C. for one hour in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded 7F 6-(5-aminopyridin-3-yl)-N-(4-(pyridin-4-yloxy)phenyl)quinazohn-4-amine (50 mg, 15% yield, 92% purity) as an off-white solid. MS (ESI⁺ m/z 407.1, ESI⁻ m/z 405.1). To a room temperature solution of 6-(5-aminopyridin-3-yl)-N-(4-(pyridin-4-yloxy)phenyl)quinazolin-4-amine (50 mg, 0.12 mmol) in pyridine (3 mL) was added methanesulfonyl chloride (56 mg, 0.5 mmol). The reaction mixture turned dark red which persisted and was stirred for 15 minutes. The reaction mixture was poured into a saturated solution of sodium bicarbonate and the organic material was extracted with ethyl acetate. The organic phase was washed with water and brine, dried over magnesium sulfate, filtered and concentrated under vacuum. The crude solid was dissolved in methanol and "dry loaded" on to a silica column eluted with a gradient of 1/9 to 3/7 methanol/ethyl acetate to give N-(5-(4-((4-(pyridin-4-yloxy)phenyl)amino)quinazolin-6-yl)pyridin-3-yl)methanesulfonamide (5F, MOL-166, 20 mg, 33% yield, 96% purity) as a solid. $^1$H NMR (400

MHz, DMSO-d$_6$) δ 10.07 (s, 1H), 8.91 (s, 1H), 8.79 (d, J=1.9 Hz, 1H), 8.62 (s, 1H), 8.4-8.5 (m, 3H), 8.15 (dd, J=1.7, 8.6 Hz, 1H), 7.85-8.0 (m, 4H), 7.24 (d, J=8.9 Hz, 2H), 6.94 (d, J=4.7 Hz, 2H), 3.08 (s, 3H); MS: (ESI$^+$ m/z 485.1, ESI$^-$ m/z 483.0).

5G, N-(5-(4-(benzylamino)quinazolin-6-yl)pyridin-3-yl)methanesulfonamide, MOL-167

A mixture of 6-bromo-4-chloroquinazoline (1.2 g, 4.9 mmol) and benzylamine (633 mg, 5.9 mmol) in 30 mL of 1,4-dioxane was heated at 45° C. for 2 hours then at 90° C. for 1 hour. An additional amount of benzylamine (500 mg, 4.7 mmol) was added and the reaction mixture was heated at 90° C. for an additional 2 hours. The reaction mixture was cooled to room temperature, diluted with diethyl ether and filtered through fritted glass. The filtrate was concentrated under vacuum and the crude solid was triturated under isopropyl alcohol, filtered and dried to give N-benzyl-6-bromoquinazolin-4-amine (3G) as a solid (950 mg, 62% yield). $^1$H NMR (400 MHz, DMSO-d$_6$) δ 8.91 (t, J=5.9 Hz, 1H), 8.60 (d, J=2.2 Hz, 1H), 8.46 (s, 1H), 7.88 (dd, J=2.2, 8.9 Hz, 1H), 7.62 (d, J=8.9 Hz, 1H), 7.25-7.40 (m, 4H), 7.23 (t, J=9 Hz, 1H), 4.75 (d, J=5.8 Hz, 2H). Next a solution consisting of N-benzyl-6-bromoquinazolin-4-amine (0.314 g, 1.0 mmol) in anhydrous ethanol (10 mL) was placed in a 20 mL microwave reaction vial containing a stir bar. Next, 3-aminopyridine-5-boronic acid pinacol ester (6, 0.231 g, 1.05 mmol) was added followed by SiliCat DPP-Pd (5 mol %, 0.26 mmol/g loading, 0.200 g) and 10% aqueous potassium carbonate solution (2 equivalents, 1.5 mL, 1.26 mmol). The reaction mixture was placed under N$_2$ atmosphere, capped, and then heated at 100° C. for 5 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded 6-(5-aminopyridin-3-yl)-N-benzylquinazolin-4-amine (7G) as a white solid (59 mg, 18% yield, 85% purity); MS: (ESI$^+$ m/z 328.1, ESI$^-$ m/z 326.1). To a room temperature solution of 6-(5-aminopyridin-3-yl)-N-benzylquinazolin-4-amine (59 mg, 0.18 mmol) in pyridine (4 mL) was added methanesulfonyl chloride (83 mg, 0.72 mmol). The reaction mixture turned dark red which persisted and was stirred for 1 hour. The reaction mixture was poured into a saturated solution of sodium bicarbonate and the organic material was extracted with ethyl acetate. The organic phase was washed with water and brine, dried over magnesium sulfate, filtered and concentrated under vacuum. The crude solid was dissolved in methanol and "dry loaded" on to a silica column eluted with a gradient of 1/9 to 3/7 methanol/ethyl acetate resulting in a partially purified pale yellow solid. This crude solid was triturated under a solution of 2-propanol/dichloromethane/ethyl acetate, filtered, and dried to give N-(5-(4-(benzylamino)quinazolin-6-yl)pyridin-3-yl)methanesulfonamide (5G, MOL-167, 6 mg, 8% yield, 96% purity) as a white powder; MS: (ESI$^+$ m/z 406.1, ESI$^-$ m/z 404.1).

5H, N-(5-(4-((3-chloro-4-methoxyphenyl)amino)quinazolin-6-yl)pyridin-3-yl)methanesulfonamide, MOL-153

A mixture of 6-bromo-4-chloroquinazoline (1.65 g, 6.5 mmol) and 3-chloro-4-methoxyaniline (1.2 g, 7.8 mmol) in 40 mL of 1,4-dioxane was heated at 90° C. for 3 hour. The reaction mixture was cooled to room temperature, diluted with diethyl ether and filtered through fritted glass. The solid was washed with diethyl ether and dried to give 6-bromo-N-(3-chloro-4-methoxyphenyl)quinazolin-4-amine (3H) as a yellow-gold solid (2.1 g, 89%); $^1$H NMR (400 MHz, DMSO-d$_6$) δ 11.5 (br s, 1H), 9.15 (s, 1H), 8.92 (s, 1H), 8.21 (d, J=9 Hz, 1H), 7.8-8.0 (m, 2H), 7.66 (dd, J=8.9, 2.3 Hz, 1H), 7.25 (d, J=8.9 Hz, 1H), 3.95 (s, 3H); MS: (ESI$^+$ m/z 364.0, 366.0 (Br isotope), ESI$^-$ m/z 362.0, 364.0 (Br isotope)). A solution of 6-bromo-N-(3-chloro-4-methoxyphenyl)quinazolin-4-amine (1.85 g, 5.08 mmol) and 3-aminopyridine-5-boronic acid pinacol ester (6, 932 mg, 4.23 mmol) in 1,4-dioxane (90 mL) and water (7.6 mL) was degassed. To the solution was added cesium carbonate (6.9 g, 21.1 mmol) and [1,1'-bis(diphenylphosphino)ferrocene] dichloropalladium(II) (366 mg). The reaction mixture was heated at 90° C.-95° C. under N$_2$ for 4 hours. The reaction mixture was diluted with ethyl acetate, dichloromethane and methanol, washed with saturated sodium bicarbonate, water and brine, dried over magnesium sulfate, filtered and concentrated under vacuum. The crude material was purified by silica gel column chromatography eluting with a gradient of 2/98 to 25/75 methanol/ethyl acetate to afford 6-(5-aminopyridin-3-yl)-N-(3-chloro-4-methoxyphenyl)quinazolin-4-amine (7H) as an off white solid (524 mg, 33% yield). To a room temperature solution of 6-(5-aminopyridin-3-yl)-N-(3-chloro-4-methoxyphenyl)quinazolin-4-amine (250 mg, 0.66 mmol) in pyridine (15 mL) was added methanesulfonyl chloride (303 mg, 2.65 mmol). The reaction mixture turned dark red which persisted and was stirred for 1 hour. The reaction mixture was poured into a saturated solution of sodium bicarbonate and the organic material was extracted with ethyl acetate. The organic phase was washed with water and brine, dried over magnesium sulfate, filtered and concentrated under vacuum. The crude yellow solid was dissolved in methanol. Ethyl acetate and diethyl ether were added until cloudiness was observed. The mixture was stirred for 1 hour and the resulting solid was filtered, washed with ethyl acetate and dried to give N-(5-(4-((3-chloro-4-methoxyphenyl)amino)quinazolin-6-yl)pyridin-3-yl)methanesulfonamide (5H, MOL-153, 120 mg, 40% yield, 94% purity) as a bright yellow powder; $^1$H NMR (400 MHz, DMSO-d$_6$) δ 11.6 (br s, 1H), 10.3 (br s, 1H), 9.17 (s, 1H), 8.95 (s, 1H), 8.88 (br s, 1H), 8.52 (br s, 1H), 8.40 (dd, J=1.3, 8.6 Hz, 1H), 8.0-8.1 (m, 1H), 7.89 (d, J=2.6 Hz, 1H), 7.66 (dd, J=2.6, 8.9 Hz, 1H), 7.28 (d, J=9.0 Hz, 1H), 3.90 (s, 3H), 3.16 (s, 3H); MS: (ESI$^+$ m/z 456).

Example 5

This example shows University of Michigan Quinazoline Experimentals (Synthesis of MOL-154).

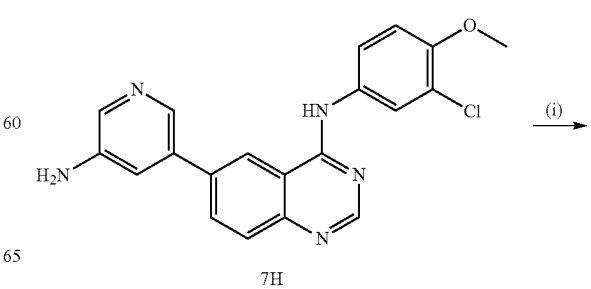

7H

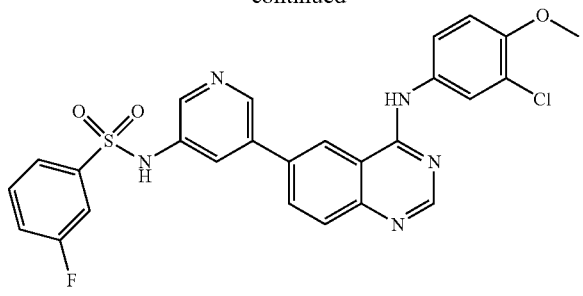

8

Reaction conditions: (i) pyridine, 3-fluorobenzensulfonyl chloride, rt, 1 hour

8, (N-(5-(4-((3-chloro-4-methoxyphenyl)amino) quinazolin-6-yl)pyridin-3-yl)-3-fluorobenzenesulfonamide, MOL-154)

To a room temperature solution of 6-(5-aminopyridin-3-yl)-N-(3-chloro-4-methoxyphenyl)quinazolin-4-amine (7H, 250 mg, 0.66 mmol) in pyridine (15 mL) was added 3-fluorobenzenesulfonyl chloride (516 mg, 2.65 mmol). The reaction mixture turned dark red which persisted and was stirred for 1 hour. The reaction mixture was poured into a saturated solution of sodium bicarbonate and the organic material was extracted with ethyl acetate. The organic phase was washed with water and brine, dried over magnesium sulfate, filtered and concentrated under vacuum. Roto-evaporation with heptane provided a crude yellow solid which was triturated under a mixture of methanol and ethyl acetate and diethyl ether for 1 hour and the resulting solid was filtered and dried to give N-(5-(4-((3-chloro-4-methoxyphenyl)amino)quinazolin-6-yl)pyridin-3-yl)-3-fluorobenzenesulfonamide (8, MOL-154, 120 mg, 34% yield, 100% purity) as a yellow powder; $^1$H NMR (400 MHz, DMSO-$d_6$) δ 10.8 (br s, 1H), 10.0 (br s, 1H), 8.82 (s, 2H), 8.62 (s, 1H), 8.29 (d, J=2.2 Hz, 1H), 8.07 (d, J=7.5 Hz, 1H), 7.96 (d, J=2.3 Hz, 1H), 7.93 (d, J=1.9 Hz, 1H), 7.87 (d, J=8.9 Hz, 1H), 7.72 (dd, J=2.4, 8.9 Hz, 1H), 7.6-7.7 (m, 2H), 7.45-7.55 (m, 1H), 7.28 (d, J=9.0 Hz, 1H), 3.88 (s, 3H); MS: (ESI$^+$ m/z 536).

Example 6

This example shows University of Michigan Quinazoline Library 4-Experimentals (Synthesis of MOL-171-177, MOL-181-186, and MOL-191-196)

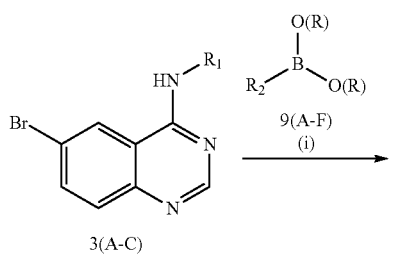

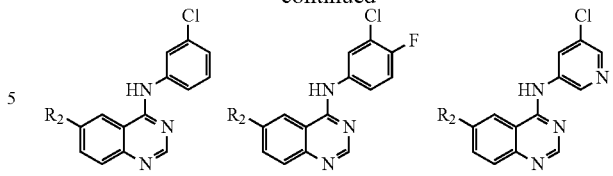

Reaction conditions: (i) SiliaCatDpp-Pd 5 mol %, 10% K$_2$CO$_3$, EtOH, 100° C., 12-30 minutes, μW 3A- 6-bromo-N-(3-chloro-4-fluorophenyl)quinazolin-4-amine
3B- 6-bromo-N-(3-chlorophenyl)quinazolin-4-amine
3C- 6-bromo-N-(5-chloropyridin-3-yl)quinazolin-4-amine
9A - (2-aminopyrimidin-5-yl)boronic acid
9B - 5-(4,4,5,5-tetramethyl-1,3,2-dioxaborolan-2-yl)-1H-pyrrolo[2,3-b]pyridine
9C - 1-methyl-3-(4-(4,4,5,5-tetramethyl-1,3,2-dioxaborolan-2-yl)phenyl)urea
9D - N-(3-(4,4,5,5-tetramethyl-1,3,2-dioxaborolan-2-yl)phenyl)methanesulfonamide
9E - (3-(2H-tetrazol-5-yl)phenyl)boronic acid
9F - (1H-pyrazol-4-yl)boronic acid

10A, 6-(2-aminopyrimidin-5-yl)-N-(3-chlorophenyl) quinazolin-4-amine, MOL-171

To a solution consisting of 6-bromo-N-(3-chlorophenyl)quinazolin-4-amine (3B, 0.115 g, 0.343 mmol) in anhydrous ethanol (4 mL) was placed in a 5 mL microwave reaction vial containing a stir bar. Next, (2-aminopyrimidin-5-yl)boronic acid (9A, 0.50 g, 0.361 mmol) was added followed by SiliCat DPP-Pd (5 mol %, 0.26 mmol/g loading, 0.068 g) and 10% aqueous potassium carbonate solution (2 equivalents, 0.50 mL, 0.68 mmol). The reaction mixture was placed under N$_2$ atmosphere, capped, and then heated at 100° C. for 15 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded 6-(2-aminopyrimidin-5-yl)-N-(3-chlorophenyl)quinazolin-4-amine (10A, MOL-171, 26.4 mg, 22% yield, 95% purity) as a white solid; $^1$H NMR (400 MHz, DMSO-$d_6$) δ 9.88 (s, 1H), 8.83 (s, 1H), 8.76 (m, 1H), 8.65 (s, 1H), 8.20 (dd, J=1.65, 8.60 Hz, 1H), 8.10 (t, J=1.92 Hz, 1H), 7.73-7.99 (m, 2H), 7.45 (t, J=8.14 Hz, 1H), 7.07-7.31 (m, 1H), 6.95 (s, 2H); MS: (ESI$^+$ m/z 348.8, ESI$^-$ m/z 346.8); TLC: (90:10:0.5, DCM:MeOH:NH$_4$OH) R$_f$=0.52. Each of the following (10B-10F) was prepared in the manner described for 10A unless otherwise noted:

10B, N-(3-chlorophenyl)-6-(1H-pyrrolo[2,3-b]pyridin-5-yl)quinazolin-4-amine, MOL-172

5-(4,4,5,5-tetramethyl-1,3,2-dioxaborolan-2-yl)-1H-pyrrolo[2,3-b]pyridine 9B was used instead of 9A to afford the title compound as an off-white solid (0.022 g, 20% yield, 97% purity); $^1$H NMR (400 MHz, DMSO-$d_6$) δ 11.81 (br. s., 1H), 10.06 (br. s., 1H), 8.86 (s, 1H), 8.75 (d, J=1.83 Hz, 1H), 8.56 (br. s., 1H), 8.42 (d, J=2.01 Hz, 1H), 8.22 (d, J=8.05 Hz, 1H), 8.05 (br. s., 1H), 7.68-7.93 (m, 2H), 7.56 (d, J=3.29 Hz, 1H), 7.40 (t, J=8.14 Hz, 1H), 7.12 (d, J=7.14 Hz, 1H), 6.56 (d, J=5.51 Hz, 1H); MS: (ESI$^+$ m/z 371.8, ESI$^-$ m/z 369.8); TLC: (90:10:0.5, DCM:MeOH:NH$_4$OH) R$_f$=0.54.

10C, 1-(4-(4-((3-chlorophenyl)amino)quinazolin-6-yl)phenyl)-3-methylurea, MOL-173

1-methyl-3-(4-(4,4,5,5-tetramethyl-1,3,2-dioxaborolan-2-yl)phenyl)urea 9C was used instead of 9A to afford the title compound as an off-white solid (0.037 g, 28% yield, 96% purity); $^1$H NMR (400 MHz, DMSO-d$_6$) δ 9.96 (s, 1H), 8.77 (d, J=1.83 Hz, 1H), 8.71 (s, 1H), 8.64 (s, 1H), 8.14-8.41 (m, 1H), 8.01-8.14 (m, 1H), 7.69-7.96 (m, 2H), 7.59 (d, J=8.60 Hz, 1H), 7.45 (t, J=8.14 Hz, 1H), 7.06-7.31 (m, 1H), 6.07 (d, J=4.57 Hz, 1H), 3.33 (s, 3H); MS: (ESI$^+$ m/z 403.8, ESI$^-$ m/z 401.8); TLC: (90:10:0.5, DCM:MeOH:NH$_4$OH) R$_f$=0.54.

10D, N-(3-(4-((3-chlorophenyl)amino)quinazolin-6-yl)phenyl)methanesulfonamide, MOL-174

N-(3-(4,4,5,5-tetramethyl-1,3,2-dioxaborolan-2-yl)phenyl)methanesulfonamideurea 9D was used instead of 9A to afford the title compound as an off-white solid (0.049 g, 39% yield, 96% purity); $^1$H NMR (400 MHz, DMSO-d$_6$) δ 10.04 (s, 1H), 9.91 (s, 1H), 8.81 (d, J=1.83 Hz, 1H), 8.68 (s, 1H), 8.02-8.22 (m, 2H), 7.75-8.01 (m, 2H), 7.59-7.67 (m, 1H), 7.50-7.59 (m, 1H), 7.45 (t, J=8.14 Hz, 1H), 7.31 (d, J=8.60 Hz, 1H), 7.20 (dd, J=1.74, 7.78 Hz, 1H) 3.07 (s, 3H); MS: (ESI$^+$ m/z 425.8, ESI$^-$ m/z 423.7); TLC: (90:10:0.5, DCM:MeOH:NH$_4$OH) R$_f$=0.62.

10E, 6-(3-(1H-tetrazol-5-yl)phenyl)-N-(3-chlorophenyl)quinazolin-4-amine, MOL-175

(3-(2H-tetrazol-5-yl)phenyl)boronic acid 9E was used instead of 9A to afford the title compound as an off-white solid (0.049 g, 21% yield, 98% purity); $^1$H NMR (400 MHz, DMSO-d$_6$) δ 10.10 (br. s., 1H), 8.94 (s, 1H), 8.54 (s, 1H), 8.29 (d, J=8.78 Hz, 1H), 8.03-8.19 (m, 2H), 7.96 (d, J=8.60 Hz, 1H), 7.64-7.92 (m, 2H), 7.46 (t, J=8.05 Hz, 1H), 7.22 (dd, J=1.30, 7.90 Hz, 1H); MS: (ESI$^+$ m/z 400.0, ESI$^-$ m/z 398.1); TLC: (90:10:0.5, DCM:MeOH:NH$_4$OH) R$_f$=0.56.

10F, N-(3-chlorophenyl)-6-(1H-pyrazol-4-yl)quinazolin-4-amine, MOL-176

(1H-pyrazol-4-yl)boronic acid 9F was used instead of 9A to afford the title compound as a white solid (0.010 g, 9% yield, 98% purity); $^1$H NMR (400 MHz, DMSO-d$_6$) δ 13.11 (br. s., 1H), 9.80 (s, 1H), 8.72 (s, 1H), 8.62 (s, 1H), 8.35 (br. s., 1H) 8.09-8.21 (m, 2H), 7.88 (dd, 1.80, 8.00 Hz, 1H), 7.80 (d, J=8.78 Hz, 1H), 7.46 (t, J=8.14 Hz, 1H), 7.20 (dd, J=1.80, 8.34 Hz, 1H); MS: (ESI$^+$ m/z 322.0, ESI$^-$ m/z 320.0); TLC: (90:10:0.5, DCM:MeOH:NH$_4$OH) R$_f$=0.54.

N-(3-chlorophenyl)-6-(1H-pyrazolo[3,4-b]pyridin-5-yl)quinazolin-4-amine, MOL-177

To a solution consisting of 6-bromo-N-(3-chlorophenyl)quinazolin-4-amine (0.133 g, 0.36 mmol) and 1H-pyrazolo[3,4-b]pyridine-5-boronic acid pinacol ester (0.133 g, 0.54 mmol) in 1,4-dioxane (2 mL) in a 2 mL microwave reaction vial containing a stir bar was added 2M K$_2$CO$_3$ (0.72 mL, 1.44 mmol). The mixture was degassed (vacuum/nitrogen, 3 times) before the addition of SiliCat DPP-Pd (0.10 g, 0.26 mmol/g loading) and then heated three times at 140° C. for 20 minutes in a Biotage Emrys Optimizer microwave. The reaction mixture was allowed to cool to room temperature, the aqueous layer was removed with a disposable pipette, and the remaining organic phase was filtered through a fritted funnel to collect SiliCat DPP-Pd. The filtered solid was rinsed with room temperature methanol and the filtrate was set aside. The filtered solids were then washed well with hot methanol and the filtrate was concentrated under reduced pressure to afford the title compound as a pale yellow solid (43 mg, 32%, 94.9% purity); TLC R$_f$0.10 (solvent system: 7:3 v/v ethyl acetate-heptane); MS (ES-API+) m/z 373.0 (M+1), 375.0 (Cl isotope), (ES-API−) m/z 371.0 (M-1), 373.0 (Cl isotope); $^1$H NMR (400 MHz, DMSO-d$_6$) δ 9.01 (d, J=1.28 Hz, 1H), 8.86 (s, 1H), 8.62 (s, 1H), 8.53 (s, 1H), 8.18-8.25 (m, 2H), 8.01 (s, 1H), 7.80 (d, J=8.69 Hz, 1H), 7.75 (br d, J=8.23 Hz, 1H), 7.37 (t, J=7.96 Hz, 1H), 7.09 (br d, J=7.87 Hz, 1H).

11A, 6-(2-aminopyrimidin-5-yl)-N-(3-chloro-4-fluorophenyl)quinazolin-4-amine, MOL-181

To a solution consisting of 6-bromo-N-(3-chloro-4-fluorophenyl)quinazolin-4-amine (3A, 0.150 g, 0.425 mmol) in anhydrous ethanol (4 mL) was placed in a 5 mL microwave reaction vial containing a stir bar. Next, (2-aminopyrimidin-5-yl)boronic acid (9A, 0.62 g, 0.447 mmol) was added followed by SiliCat DPP-Pd (5 mol %, 0.26 mmol/g loading, 0.085 g) and 10% aqueous potassium carbonate solution (2 equivalents, 0.62 mL, 0.85 mmol). The reaction mixture was placed under N2 atmosphere, capped, and then heated at 100° C. for 15 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded 6-(2-aminopyrimidin-5-yl)-N-(3-chloro-4-fluorophenyl)quinazolin-4-amine (11A, MOL-181, 75 mg, 48% yield, 95% purity) as a white solid; $^1$H NMR (400 MHz, DMSO-d$_6$) δ 9.91 (s, 1H), 8.82 (s, 1H), 8.69-8.78 (m, 1H), 8.63 (s, 1H), 8.04-8.29 (m, 1H), 7.78-7.92 (m, 1H), 7.49 (t, J=9.06 Hz, 1H), 6.96 (s, 2H); MS: (ESI$^+$ m/z 367.0, ESI$^-$ m/z 365.0); TLC: (90:10:0.5, DCM:MeOH:NH$_4$OH) R$_f$=0.58.

Each of the following (11B-11F) was prepared in the manner described for 11A unless otherwise noted:

11B, N-(3-chloro-4-fluorophenyl)-6-(1H-pyrrolo[2,3-b]pyridin-5-yl)quinazolin-4-amine, MOL-182

5-(4,4,5,5-tetramethyl-1,3,2-dioxaborolan-2-yl)-1H-pyrrolo[2,3-b]pyridine 9B was used instead of 9A to afford the title compound as an off-white solid (0.067 g, 41% yield, 98% purity); $^1$H NMR (400 MHz, DMSO-d$_6$) δ 11.84 (br. s., 1H), 10.01 (s, 1H), 8.83-8.99 (m, 1H), 8.78 (d, J=2.01 Hz, 1H), 8.65 (s, 1H), 8.44 (d, J=2.01 Hz, 1H), 8.17-8.37 (m, 2H), 7.83-7.95 (m, 1H), 7.57 (t, J=2.93 Hz, 1H), 7.49 (t, J=9.15 Hz, 1H), 6.41-6.67 (m, 1H); MS: (ESI$^+$ m/z 390.1, ESI$^-$ m/z 388.1); TLC: (90:10:0.5, DCM:MeOH:NH$_4$OH) R$_f$=0.63

11C, 1-(4-(4-((3-chloro-4-fluorophenyflamino)quinazolin-6-yl)phenyl)-3-methylurea, MOL-183

1-methyl-3-(4-(4,4,5,5-tetramethyl-1,3,2-dioxaborolan-2-yl)phenyl)urea 9C was used instead of 9A to afford the title compound as an off-white solid (0.022 g, 13% yield, 100% purity); $^1$H NMR (400 MHz, DMSO-d$_6$) δ 9.98 (s, 1H), 8.75 (d, J=1.40 Hz, 1H), 8.71 (s, 1H), 8.63 (s, 1H), 8.06-8.27 (m, 1H), 7.70-7.91 (m, 2H), 7.59 (d, J=8.60 Hz, 1H), 7.49 (t, J=9.06 Hz, 1H), 6.08 (d, J=4.76 Hz, 1H), 3.33 (s, 3H), 2.67 (d, J=4.57 Hz, 2H); MS: (ESI$^+$ m/z 422.1, ESI$^-$ m/z 420.1); TLC: (90:10:0.5, DCM:MeOH:NH$_4$OH) R$_f$=0.58.

11D, N-(3-(4-((3-chloro-4-fluorophenyl)amino)quinazolin-6-yl)phenyl)methanesulfonamide, MOL-184

N-(3-(4,4,5,5-tetramethyl-1,3,2-dioxaborolan-2-yl)phenyl)methanesulfonamideurea 9D was used instead of 9A to afford the title compound as an off-white solid (0.056 g, 30% yield, 96% purity); $^1$H NMR (400 MHz, DMSO-d$_6$) δ 10.06 (s, 1H), 9.91 (s, 1H), 8.77 (s, 1H), 8.66 (s, 1H), 8.19 (dd, J=2.47, 6.86 Hz, 1H), 8.11 (dd, J=1.37, 8.69 Hz, 1H), 7.72-7.99 (m, 2H), 7.41-7.65 (m, 3H), 7.30 (d, J=7.87 Hz, 1H), 3.07 (s, 3H); MS: (ESI$^+$ m/z 443.1, ESI$^-$ m/z 441.1); TLC: (90:10:0.5, DCM:MeOH:NH$_4$OH) R$_f$=0.66.

11E, 6-(3-(1H-tetrazol-5-yl)phenyl)-N-(3-chloro-4-fluorophenyl)quinazolin-4-amine, MOL-185

(3-(2H-tetrazol-5-yl)phenyl)boronic acid 9E was used instead of 9A to afford the title compound as an off-white solid (0.007 g, 4% yield, 83% purity); $^1$H NMR (400 MHz, DMSO-d$_6$) δ 10.24 (br. s., 1H), 9.03 (s, 1H), 8.66 (m, 2H), 8.28 (m, 2H), 8.10 (d, J=7.32 Hz, 1H), 7.81-8.03 (m, 2H), 7.68 (t, J=7.32 Hz, 1H), 7.48 (t, J=9.00 Hz, 1H); MS: (ESI$^+$ m/z 418.0, ESI m/z 416.0); TLC: (90:10:0.5, DCM:MeOH:NH$_4$OH) R$_f$=0.22.

11F, N-(3-chloro-4-fluorophenyl)-6-(1H-pyrazol-4-yl)quinazolin-4-amine, MOL-186

(1H-pyrazol-4-yl)boronic acid 9F was used instead of 9A to afford the title compound as a white solid (0.022 g, 15% yield, 97% purity); $^1$H NMR (400 MHz, DMSO-d$_6$) δ 13.11 (br. s., 1H), 9.80 (s, 1H), 8.69 (s, 1H), 8.59 (s, 1H), 8.35 (br. s., 1H) 8.02-8.28 (m, 2H), 7.80-7.92 (m, 1H), 7.79 (d, J=8.78 Hz, 1H), 7.49 (t, J=9.14 Hz, 1H), 7.20 (dd, J=1.80, 8.34 Hz, 1H); MS: (ESI$^+$ m/z 340.0, ESI$^-$ m/z 338.0); TLC: (90:10:0.5, DCM:MeOH:NH$_4$OH) R$_f$=0.54.

3-(4-((3-chloro-4-fluorophenyl)amino)quinazolin-6-yl)-N-cyclopropylbenzenesulfonamide, MOL-214

A mixture consisting of 6-bromo-N-(3-chlorophenyl)quinazolin-4-amine—HCl (100 mg 0.26 mmol), (3-(N-cyclopropylsulfamoyl)phenyl)boronic acid (94 mg, 0.39 mmol) and 1.4M K$_2$CO$_3$ (1.1 mL) in 3 mL of 1,4-dioxane was degassed (vacuum/nitrogen, 3 times). To the reaction mixture was added SiliCat DPP-Pd (50 mg, 0.26 mmol/g loading). The reaction mixture was sealed and heated at 100° C. for 12 minutes in a Biotage Emrys Optimizer microwave. To the reaction mixture was added additional 2-chloro-5-(4,4,5,5-tetramethyl-1,3,2-dioxaborolan-2-yl)aniline (40 mg, 0.16 mmol) and SiliCat DPP-Pd (30 mg). The reaction mixture was heated again at 120° C. for 15 minutes and cooled. The aqueous phase was removed and the remaining organic phase was filtered through a glass frit. The solids were washed with methanol. The filtrate was concentrated under reduced pressure. The white solid residue was applied to a 40 g silica column using the dry loading method and eluted with a gradient of 4:6 ethyl acetate-heptane to 100% ethyl acetate to give 20 mg (16%, purity 96%) of the title compound as a pale yellow solid; MS (ES-API+) m/z 469.0 (M+1), 471.0 (Cl isotope); $^1$H NMR (400 MHz, DMSO-d6) δ 10.13 (s, 1H), 8.87 (s, 1H), 8.67 (s, 1H), 8.14-8.27 (m, 4H), 8.01 (d, J=2.65 Hz, 1H), 7.95 (d, J=8.69 Hz, 1H), 7.87-7.92 (m, 1H), 7.79-7.87 (m, 2H), 7.49 (t, J=9.06 Hz, 1H), 2.17 (dt, J=3.34, 6.75 Hz, 1H), 0.37-0.54 (m, 4H).

13 N-(3-chloro-4-fluorophenyl)-6-(6-methoxypyridin-3-yl)quinazolin-4-amine, MOL-151

A solution of 6-bromo-N-(3-chloro-4-fluorophenyl)quinazolin-4-amine (3A, 275 mg, 0.78 mmol) and (6-methoxypyridin-3-yl)boronic acid (9G, 119 mg, 0.78 mmol) in 1,4-dioxane (15 mL) and water (1.4 mL) was degassed. To the solution was added cesium carbonate (1.0 g, 3.1 mmol) and [1,1'-bis(diphenylphosphino)ferrocene]dichloropalladium(II) (44 mg). The reaction mixture was heated at 80° C. under N$_2$ for 2 hours. The reaction mixture was diluted with toluene and the volatiles were removed under vacuum and the crude material was purified by silica gel column chromatography eluting with a gradient of 3/7 to 6/4 ethyl acetate/heptane to give N-(3-chloro-4-fluorophenyl)-6-(6-methoxypyridin-3-yl)quinazolin-4-amine (13, MOL-151, 40 mg, 13%, 95% purity by HPLC) as a yellow solid; $^1$H NMR (400 MHz, DMSO-d$_6$) δ 9.93 (s, 1H), 8.77 (d, J=1.5 Hz, 1H), 8.69 (d, J=2.6 Hz, 1H), 8.63 (s, 1H), 8.1-8.24 (m, 3H), 7.78-7.92 (m, 2H), 7.46 (t, J=9.15 Hz, 1H), 7.00 (d, J=8.8 Hz, 1H), 3.92 (s, 3H); MS: (ESI$^+$ m/z 381.1, ESI$^-$ m/z 379.1).

12A, 6-(2-aminopyrimidin-5-yl)-N-(5-chloropyridin-3-yl)quinazolin-4-amine, MOL-191

To a solution consisting of 6-bromo-N-(5-chloropyridin-3-yl)quinazolin-4-amine (3C, 0.150 g, 0.447 mmol) in anhydrous ethanol (4 mL) was placed in a 5 mL microwave reaction vial containing a stir bar. Next, (2-aminopyrimidin-5-yl)boronic acid (9A, 0.65 g, 0.469 mmol) was added followed by SiliCat DPP-Pd (5 mol %, 0.26 mmol/g loading, 0.090 g) and 10% aqueous potassium carbonate solution (2 equivalents, 0.65 mL, 0.89 mmol). The reaction mixture was placed under N$_2$ atmosphere, capped, and then heated at 100° C. for 15 minutes in a Biotage Emrys Optimizer microwave. The reaction mixture was allowed to cool to room temperature and then filtered over a fritted funnel to collect SiliCat DPP-Pd. The filtered solid was rinsed with excess ethanol and the filtrate was concentrated under reduced pressure to afford the crude product. Purification of the crude product by Biotage Isolera flash chromatography using a gradient of 4-100% ethyl acetate in heptane, followed by 0-10% methanol in dichloromethane afforded 6-(2-aminopyrimidin-5-yl)-N-(5-chloropyridin-3-yl)quinazolin-4-amine (12A, MOL-191, 44 mg, 28% yield, 95% purity) as a white solid; $^1$H NMR (400 MHz, DMSO-d$_6$) δ 10.06 (s, 1H), 9.01 (s, 1H), 8.83 (s, 1H), 8.70 (s, 1H), 8.62 (br. s., 1H), 8.39 (d, J=1.50 Hz, 1H), 8.23 (d, J=8.23 Hz 1H), 7.89 (d, J=8.60 Hz, 1H), 6.97 (s, 2H); MS: (ESI$^+$ m/z 350.0, ESI$^-$ m/z 348.0); TLC: (90:10:0.5, DCM:MeOH:NH$_4$OH) R$_f$=0.40.

Each of the following (12B-12F) was prepared in the manner described for 12A unless otherwise noted:

12B, N-(5-chloropyridin-3-yl)-6-(1H-pyrrolo[2,3-b]pyridin-5-yl)quinazolin-4-amine, MOL-192

5-(4,4,5,5-tetramethyl-1,3,2-dioxaborolan-2-yl)-1H-pyrrolo[2,3-b]pyridine 9B was used instead of 9A to afford the title compound as an off-white solid (0.052 g, 31% yield, 98% purity); $^1$H NMR (400 MHz, DMSO-d$_6$) δ 11.84 (br. s., 1H), 10.16 (s, 1H), 9.03 (d, J=2.01 Hz, 1H), 8.89 (m, 1H), 8.78 (d, J=2.01 Hz, 1H), 8.71 (s, 1H), 8.63 (t, J=2.01 Hz, 1H), 8.44 (d, J=2.01 Hz, 1H), 8.14-8.41 (m, 2H), 7.93 (d, J=8.60 Hz, 1H), 7.57 (t, J=2.93 Hz, 1H), 6.57 (dd, J=1.83, 3.48 Hz, 1H); MS: (ESI$^+$ m/z 373.1, ESI$^-$ m/z 371.1); TLC: (90:10:0.5, DCM:MeOH:NH$_4$OH) R$_f$=0.50.

12C, 1-(4-(4-((5-chloropyridin-3-yl)amino)quinazolin-6-yl)phenyl)-3-methylurea, MOL-193

1-methyl-3-(4-(4,4,5,5-tetramethyl-1,3,2-dioxaborolan-2-yl)phenyl)urea 9C was used instead of 9A to afford the title compound as a white solid (0.016 g, 9% yield, 98% purity); $^1$H NMR (400 MHz, DMSO-d$_6$) δ 10.14 (br. s., 1H), 9.02 (br. s., 1H), 8.65-8.88 (m, 2H), 8.62 (br. s., 1H), 8.38 (br. s., 1H), 8.21 (d, J=8.78 Hz, 1H), 7.88 (d, J=8.42 Hz, 1H), 7.79 (d, J=8.42 Hz, 1H), 7.59 (d, J=8.42 Hz, 1H), 6.08 (d, J=4.76 Hz, 1H), 3.33 (s, 3H), 2.67 (d, J=4.21 Hz, 2H); MS: (ESI$^+$ m/z 405.1, ESI$^-$ m/z 403.1); TLC: (90:10:0.5, DCM:MeOH:NH$_4$OH) R$_f$=0.49.

12D, N-(3-(4-((5-chloropyridin-3-yl)amino)quinazolin-6-yl)phenyl)methanesulfonamide, MOL-194

N-(3-(4,4,5,5-tetramethyl-1,3,2-dioxaborolan-2-yl)phenyl)methanesulfonamideurea 9D was used instead of 9A to afford the title compound as a white solid (0.049 g, 26% yield, 97% purity); $^1$H NMR (400 MHz, DMSO-d$_6$) δ 10.23 (s, 1H), 9.93 (s, 1H), 9.00 (s, 1H), 8.80 (s, 1H), 8.73 (s, 1H), 8.61 (br. s., 1H), 8.39 (d, J=2.01 Hz, 1H), 8.14 (dd, J=1.37, 8.69 Hz, 1H), 7.95 (d, J=8.78 Hz, 1H), 7.43-7.65 (m, 2H), 7.32 (d, J=7.87 Hz, 1H), 3.08 (s, 3H); MS: (ESI$^+$ m/z 426.0, ESI$^-$ m/z 424.0); TLC: (90:10:0.5, DCM:MeOH:NH$_4$OH) R$_f$=0.51.

12E, 6-(3-(1H-tetrazol-5-yl)phenyl)-N-(5-chloropyridin-3-yl)quinazolin-4-amine, MOL-195

(3-(2H-tetrazol-5-yl)phenyl)boronic acid 9E was used instead of 9A to afford the title compound as an off-white solid (0.030 g, 17% yield, 95% purity); $^1$H NMR (400 MHz, DMSO-d$_6$) δ 10.28 (s, 1H), 9.01 (d, J=1.83 Hz, 1H), 8.93 (s, 1H), 8.74 (s, 1H), 8.61 (t, J=1.83 Hz, 2H), 8.54 (s, 1H), 8.40 (d, J=2.01 Hz, 1H), 8.32 (dd, J=1.46, 8.78 Hz, 1H), 8.10 (dd, J=8.05, 13.91 Hz, 2H), 7.99 (t, J=8.60 Hz, 1H), 7.81 (t, J=7.78 Hz, 1H); MS: (ESI$^+$ m/z 401.0, ESI$^-$ m/z 399.1); TLC: (90:10:0.5, DCM:MeOH:NH$_4$OH) R$_f$=0.08.

12F, N-(5-chloropyridin-3-yl)-6-(1H-pyrazol-4-yl)quinazolin-4-amine, MOL-196

(1H-pyrazol-4-yl)boronic acid 9F was used instead of 9A to afford the title compound as a white solid (0.010 g, 7% yield, 99% purity); $^1$H NMR (400 MHz, DMSO-d$_6$) δ 13.12 (br. s., 1H), 9.98 (s, 1H), 9.01 (br. s., 1H), 8.60-8.72 (m, 3H), 8.38 (d, J=2.01 Hz, 1H), 8.18 (d, J=8.42 Hz, 2H), 7.83 (d, J=8.23 Hz, 1H), 7.68 (s, 1H); MS: (ESI$^+$ m/z 323.0, ESI$^-$ m/z 321.0); TLC: (90:10:0.5, DCM:MeOH:NH$_4$OH) R$_f$=0.37.

Example 7

This example shows EMD Quinazoline Experimentals (Synthesis of EMD-151)

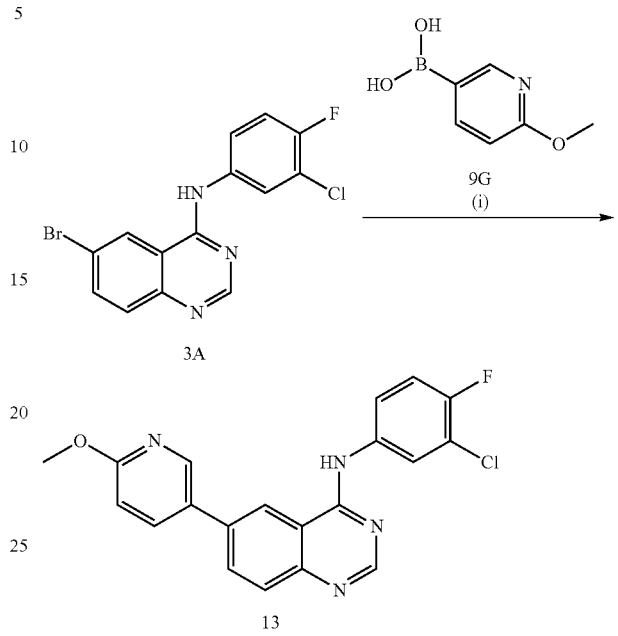

Reaction conditions: (i) dioxane, Cs$_2$CO$_3$, PdCl$_2$(dppf), 80° C., 2 hour

13 N-(3-chloro-4-fluorophenyl)-6-(6-methoxypyridin-3-yl)quinazolin-4-amine, EMD-151

A solution of 6-bromo-N-(3-chloro-4-fluorophenyl)quinazolin-4-amine (3A, 275 mg, 0.78 mmol) and (6-methoxypyridin-3-yl)boronic acid (9G, 119 mg, 0.78 mmol) in 1,4-dioxane (15 mL) and water (1.4 mL) was degassed. To the solution was added cesium carbonate (1.0 g, 3.1 mmol) and [1,1'-bis(diphenylphosphino)ferrocene]dichloropalladium(II) (44 mg). The reaction mixture was heated at 80° C. under N$_2$ for 2 hours. The reaction mixture was diluted with toluene and the volatiles were removed under vacuum and the crude material was purified by silica gel column chromatography eluting with a gradient of 3/7 to 6/4 ethyl acetate/heptane to give N-(3-chloro-4-fluorophenyl)-6-(6-methoxypyridin-3-yl)quinazolin-4-amine (13, EMD-151, 40 mg, 13%, 95% purity by HPLC) as a yellow solid; $^1$H NMR (400 MHz, DMSO-d$_6$) δ 9.93 (s, 1H), 8.77 (d, J=1.5 Hz, 1H), 8.69 (d, J=2.6 Hz, 1H), 8.63 (s, 1H), 8.1-8.24 (m, 3H), 7.78-7.92 (m, 2H), 7.46 (t, J=9.15 Hz, 1H), 7.00 (d, J=8.8 Hz, 1H), 3.92 (s, 3H); MS: (ESI$^+$ m/z 381.1, ESI m/z 379.1).

Example 8

This example describes the synthesis of additional quinazoline based compounds of the present invention.

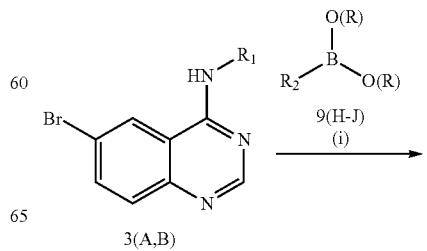

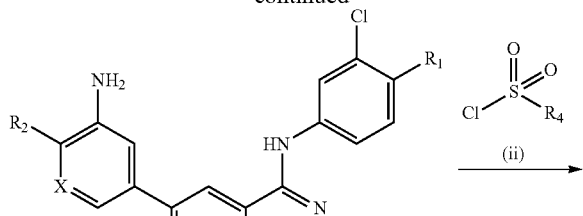

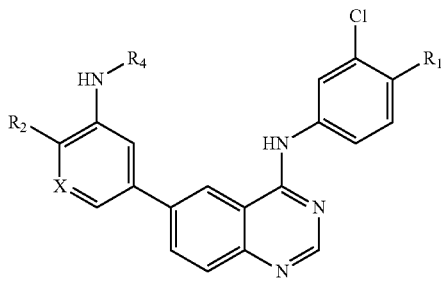

Reaction conditions: (i) SiliaCatDpp-Pd 5 mol %, 10% K₂CO₃, EtOH, 100° C., 12-30 minutes, µW, (ii) pyridine, RT, overnight
3A- 6-bromo-N-(3-chloro-4-fluorophenyl)quinazolin-4-amine
3B- 6-bromo-N-(3-chlorophenyl)quinazolin-4-amine
9H - 2-chloro-5-(4,4,5,5-tetramethyl-1,3,2-dioxaborolan-2-yl)pyridine-3-amine
9I - 2-methoxy-5-(4,4,5,5-tetramethyl-1,3,2-dioxaborolan-2-yl)pyridin-3-amine
9J - 2-chloro-5-(4,4,5,5-tetramethyl-1,3,2-dioxaborolan-2-yl)aniline
10H - 6-(5-amino-6-chloropyridin-3-yl)-N-(3-chlorophenyl)quinazolin-4-amine
10I - 6-(5-amino-6-methoxypyridin-3-yl)-N-(3-chloro-4-fluorophenyl)quinazolin-4-amine
11H - 6-(5-amino-6-chloropyridin-3-yl)-N-(3-chloro-4-fluorophenyl)quinazolin-4-amine
11J - 6-(3-amino-4-chlorophenyl)-N-(3-chloro-4-fluorophenyl)quinazolin-4-amine

6-(5-amino-6-chloropyridin-3-yl)-N-(3-chlorophenyl)quinazolin-4-amine (3B), MOL-200

To a solution consisting of 6-bromo-N-(3-chlorophenyl)quinazolin-4-amine (10.0 g, 26.9 mmol) and 2-chloro-5-(4,4,5,5-tetramethyl-1,3,2-dioxaborolan-2-yl)pyridine-3-amine (9H) (6.8 g, 26.9 mmol) in 1,4-dioxane (250 mL) was added 1.4M K₂CO₃ (58 mL, 81 mmol). The mixture was degassed (vacuum/nitrogen, 3 times) before the addition of SiliCat DPP-Pd (3.5 g, 0.26 mmol/g loading) and then heated at 95° C. overnight with stirring. The reaction mixture was allowed to cool to room temperature and was diluted with ethyl acetate, methanol and dichloromethane. The mixture was washed with water twice, then brine. The organic phase was dried over magnesium sulfate, filtered, and concentrated under reduce pressure. The residue was triturated under a mix of solvents, 50 mL ethyl acetate, 40 mL dichloromethane, 10 mL methanol, 0.25 mL ammonium hydroxide, for 1 hour and filtered. The solid was washed with ethyl acetate and dried in high vacuum to afford the title compound (5.92 g, 57%). The filtrate was applied to a silica column eluted with 2:35:63 methanol-ethyl acetate-dichloromethane to afford another lot of the title compound as a white solid (0.2 g, 100% purity). TLC $R_f$ 0.16 (solvent system: 65:35 v/v ethyl acetate-heptane); MS (ES-API+) m/z 382.1 (M+1), 384.1 (Cl isotope), (ES-API−) m/z 380.0 (M-1), 382.0 (Cl isotope); ¹H NMR (400 MHz, DMSO-d6) δ 10.00 (s, 1H), 8.82 (d, J=1.74 Hz, 1H), 8.67 (s, 1H), 8.05-8.15 (m, 3H), 7.89 (d, J=8.60 Hz, 1H), 7.82-7.87 (m, 1H), 7.51 (d, J=2.20 Hz, 1H), 7.43 (t, J=8.14 Hz, 1H), 7.15-7.22 (m, 1H), 5.74 (s, 2H).

N-(2-chloro-5-(4-((3-chlorophenyl)amino)quinazolin-6-yl)pyridin-3-yl)methanesulfonamide, MOL-201

To a mixture consisting of 6-(5-amino-6-chloropyridin-3-yl)-N-(3-chlorophenyl)quinazolin-4-amine (1.99 g, 5.2 mmol) in pyridine (25 mL) was added methanesulfonyl chloride (0.35 g, 3.0 mmol) followed by another addition of methanesulfonyl chloride (0.35 g, 3.0 mmol) after 3 hours and another (0.46 mg, 4.0 mmol) after 30 minutes. The reaction mixture was stirred at room temperature overnight. To the ice cold reaction mixture was added 2N NaOH (5 mL, 10 mmol), allowed to warm to room temperature, followed by another addition (5 mL, 10 mmol) at 0° C. after 3 hours. The mixture was allowed to stir for 1 hour while warming to room temperature and 1N HCl (3 mL, 3 mmol) and brine were added. Organic material was extracted twice with ethyl acetate-methanol (8:2). The combined organic phase was washed with brine, dried over magnesium sulfate, filtered, and concentrated under reduced pressure. The residue was suspended in toluene and concentrated, followed by ethyl acetate and concentrated, to give near white solid. The solid was triturated under 20 mL/30 mL of methanol/ethyl acetate overnight and filtered to afford the title compound as an off-white solid (1.55 g, 65%, 99.6% purity). MS (ES-API+) m/z 460.0 (M+1), 462.0 (Cl isotope), (ES-API−) m/z 457.9 (M-1), 459.9 (Cl isotope); ¹H NMR (400 MHz, DMSO-d6) δ 10.04 (s, 1H), 9.93 (br s, 1H), 8.88 (s, 1H), 8.67 (s, 1H), 8.60 (s, 1H), 8.14-8.23 (m, 2H), 8.09 (t, J=1.92 Hz, 1H), 7.91 (d, J=8.69 Hz, 1H), 7.83 (dd, J=1.01, 8.33 Hz, 1H), 7.43 (t, J=8.10 Hz, 1H), 7.19 (d, J=8.14 Hz, 1H), 3.07 (s, 3H).

N-(2-chloro-5-(4-((3-chlorophenyl)amino)quinazolin-6-yl)pyridin-3-yl)-N-(methylsulfonyl)methanesulfonamide, MOL-201B To a mixture consisting of 6-(5-amino-6-chloropyridin-3-yl)-N-(3-chlorophenyl)quinazolin-4-amine (255 mg, 0.67 mmol) in pyridine (1.2 mL) was added methanesulfonyl chloride (458 mL, 4.0 mmol) in small portions. The reaction mixture was stirred at room temperature for 5 hours then stored at 3° C. overnight. The crystalline material was filtered, washed with 2 mL of methanol and triturated under 5 mL of methanol for 3 hours. The solid was filtered and dried in high vacuum to give the title compound (125 mg, 23%, 88% purity); MS (ES-API+) m/z 538 (M+1), 541 (Cl isotope), (ES-API−) m/z 535.9 (M-1), 537.9 (Cl isotope); ¹H NMR (400 MHz, DMSO-d6) δ 11.47 (br s, 1H), 9.57 (s, 1H), 9.20 (d, J=2.29 Hz, 1H), 8.97 (d, J=2.29 Hz, 1H), 8.87 (s, 1H), 8.52 (dd, J=1.60, 8.74 Hz, 1H), 8.14 (t, J=1.88 Hz, 1H), 8.02 (d, J=8.78 Hz, 1H), 7.93 (d, J=7.64 Hz, 1H), 7.49 (t, J=8.10 Hz, 1H), 7.30 (d, J=7.57 Hz, 1H), 3.76 (s, 6H).

6-(5-amino-6-methoxypyridin-3-yl)-N-(3-chlorophenyl)quinazolin-4-amine (10O, MOL202A A mixture consisting of 6-bromo-N-(3-chlorophenyl)quinazolin-4-amine—HCl (800 mg 2.15 mmol), 2-methoxy-5-(4,4,5,5-tetramethyl-1,3,2-dioxaborolan-2-yl)pyridin-3-amine (550 mg, 2.20 mmol) and 1.4M K₂CO₃ (6.1 mL) in 10 mL of 1,4-dioxane was degassed (vacuum/nitrogen, 3 times). To the reaction mixture was added SiliCat DPP-Pd (250 mg, 0.26 mmol/g loading). The reaction mixture was sealed and heated at 100° C. for 8 minutes in a Biotage Emrys Optimizer microwave. The reaction mixture was cooled, the aqueous phase removed and the remaining organic phase was filtered through a glass frit. The solids were washed with methanol. This reaction procedure was repeated 9 times. The combined filtrates were concentrated under reduced pressure. The residue was triturated under a mix of ethyl acetate, methanol, dichloromethane, and heptane overnight. The suspension was filtered to give after drying under high vacuum 2.46 g of the title compound as a gray-brown solid. The filtrate was applied to a 120 g silica column and it was eluted with a gradient of 1:1 ethyl acetate-heptane to 100% ethyl acetate to give 1.20 g of the title compound as a dull yellow solid. Total: 3.66 g (45%); MS (ES-API+) m/z 378.1 (M+1), 380.1 (Cl isotope); $^1$H NMR (400 MHz, DMSO-$d_6$) δ 9.97 (s, 1H), 8.74 (d, J=1.55 Hz, 1H), 8.64 (s, 1H), 8.10 (t, J=1.92 Hz, 1H), 8.05 (d, J=8.69 Hz, 1H), 7.81-7.90 (m, 3H), 7.42 (t, J=8.14 Hz, 1H), 7.30 (d, J=2.20 Hz, 1H), 7.17 (d, J=7.67 Hz, 1H), 5.13 (s, 2H), 3.92 (s, 3H).

N-(5-(4-((3-chlorophenyl)amino)quinazolin-6-yl)-2-methoxypyridin-3-yl)methanesulfonamide, MOL-202

To a mixture consisting of 6-(5-amino-6-methoxypyridin-3-yl)-N-(3-chlorophenyl)quinazolin-4-amine (300 mg, 0.79 mmol) in pyridine (2 mL) was added methanesulfonyl chloride (121 mg, 1.06 mmol). The reaction mixture was stirred at room temperature for 2.75 hours. The reaction mixture was filtered and the solids were washed with ethyl acetate and triturated under 2-propanol for 3 hours. The mixture was filtered and dried under high vacuum to give the title compound (267 mg, 74%) as a pale off-white solid; TLC $R_f$ 0.25 (solvent system: 1:1 v/v ethyl acetate-heptane); MS (ES-API+) m/z 456 (M+1), 458 (Cl isotope), (ES-API−) m/z 453.9 (M-1), 456.0 (Cl isotope); $^1$H NMR (400 MHz, DMSO-d6) δ 12.35 (br s, 1H), 9.62 (br s, 1H), 9.40 (s, 1H), 8.89 (s, 1H), 8.72 (d, J=2.29 Hz, 1H), 8.39 (br d, J=8.87 Hz, 1H), 8.17 (d, J=2.10 Hz, 1H), 8.12 (d, J=8.60 Hz, 1H), 8.03 (s, 1H), 7.86 (br d, J=8.33 Hz, 1H), 7.48 (t, J=8.14 Hz, 1H), 7.34 (br d, J=8.42 Hz, 1H), 3.98 (s, 3H), 3.17 (s, 3H).

N-(5-(4-((3-chlorophenyl)amino)quinazolin-6-yl)-2-methoxypyridin-3-yl)-N-(methylsulfonyl)methanesulfonamide, MOL-202B To a mixture consisting of N-(5-(4-((3-chlorophenyl)amino)quinazolin-6-yl)-2-methoxypyridin-3-yl)methanesulfonamide (150 mg, 0.33 mmol) in pyridine (0.5 mL) was added methanesulfonyl chloride (227 mg, 1.98 mmol). The reaction mixture was stirred at room temperature for 2 hours followed by 4 hours at 40° C. The reaction mixture was stored at 0° C. overnight, diluted with 1 mL of dichloromethane and 3 drops of morpholine, (addition of morpholine resulted in a homogeneous solution) and applied directly to a 25 g column of silica gel for purification. The column was eluted with a gradient of 4:6 to 8:2 v/v ethyl acetate-heptane to isolate the title compound (18 mg, 10%) as a pale brown solid; TLC $R_f$ 0.36 (solvent system: 1:1 v/v ethyl acetate-heptane); MS (ES-API+) m/z 534 (M+1), 536 (Cl isotope), (ES-API−) m/z 532 (M-1), 534 (Cl isotope).

N-(5-(4-((3-chlorophenyl)amino)quinazolin-6-yl)-2-methoxypyridin-3-yl)cyclopropanesulfonamide, MOL-204

To a mixture consisting of 6-(5-amino-6-methoxypyridin-3-yl)-N-(3-chlorophenyl)quinazolin-4-amine (200 mg, 0.53 mmol) in pyridine (0.8 mL) was added cyclopropanesulfonyl chloride (278 mg, 1.98 mmol) in two equal portions, 1 hour apart. The reaction mixture was stirred at room temperature for an additional 2.25 hours. To the reaction mixture was added methanol (185 mg, 5.3 mmol) in 1 mL of dichloromethane and 3 drops of morpholine, (addition of morpholine resulted in a homogeneous solution) and the mixture was applied directly to a 40 g column of silica gel for purification. The column was eluted with a gradient of 0:100 to 10:90 v/v methanol-ethyl acetate to isolate the title compound (45 mg, 18%) as a solid; TLC $R_f$ 0.25 (solvent system: 1:1 v/v ethyl acetate-heptane); MS (ES-API+) m/z 482 (M+1), 484 (Cl isotope), (ES-API−) m/z 480 (M-1), 482 (Cl isotope); $^1$H NMR (400 MHz, DMSO-d6) δ 9.97 (s, 1H), 9.44 (s, 1H), 8.80 (s, 1H), 8.65 (s, 1H), 8.53 (d, J=2.10 Hz, 1H), 8.17 (dd, J=1.33, 8.74 Hz, 1H), 8.05-8.11 (m, 2H), 7.88 (d, J=8.69 Hz, 1H), 7.80-7.86 (m, 1H), 7.43 (t, J=8.10 Hz, 1H), 7.15-7.21 (m, 1H), 3.99 (s, 3H), 2.69-2.79 (m, 1H), 1.96 (s, 1H), 0.83-0.98 (m, 4H).

N-(5-(4-((3-chlorophenyl)amino)quinazolin-6-yl)-2-methoxypyridin-3-yl)-2-morpholinoethane-1-sulfonamide, MOL-205

In two separate reaction vessels: To each of the two reaction vessels consisting of a suspension of 6-(5-amino-6-methoxypyridin-3-yl)-N-(3-chlorophenyl)quinazolin-4-amine (300 mg, 0.79 mmol) and N-methylmorpholine (239 mg, 2.37 mmol) in dichloromethane (20 mL) was slowly added 2-chloroethanesulfonyl chloride (258 mg, 1.58 mmol). After 4 hours of stirring at room temperature 2-chloroethanesulfonyl chloride (280 mg, 1.7 mmol) and N-methylmorpholine (276 mg, 2.7 mmol) were added. After about 3 hours, to both reaction mixtures was added morpholine (241 mg, 2.8 mmol) and the reaction was stirred at room temperature overnight. The reaction mixtures were combined and loaded directly onto a 120 gram silica column that had been equilibrated with ethyl acetate-heptane (8:2 v/v) and using enough dichloromethane to help keep the crude material in solution. The silica column was eluted with a gradient of methanol-ethyl acetate (0:100 v/v to 10:90 v/v). The resulting precipitate from the partial concentration of the proper fractions was filtered to give the title compound as a near white solid (125 mg, 28%); TLC $R_f$ 0.13 (solvent system: ethyl acetate); MS (ES-API+) m/z 555 (M+1), 557 (Cl isotope), (ES-API−) m/z 553 (M-1), 555 (Cl isotope); $^1$H NMR (400 MHz, DMSO-d6) δ 9.97 (s, 1H), 9.47 (br s, 1H), 8.79 (s, 1H), 8.65 (s, 1H), 8.51 (d, J=2.01 Hz, 1H), 8.15 (dd, J=1.46, 8.69 Hz, 1H), 8.05-8.12 (m, 2H), 7.88 (d, J=8.69 Hz, 1H), 7.80-7.86 (m, 1H), 7.84 (dd, J=1.88, 8.19 Hz, 1H), 7.43 (t, J=8.14 Hz, 1H), 7.18 (dd, J=2.01, 7.96 Hz, 1H), 3.99 (s, 3H), 3.49 (t, J=4.48 Hz, 4H), 3.34-3.42 (m, 2H), 2.76 (br t, J=7.18 Hz, 2H), 2.37 (m, 4H).

N-(5-(4-((3-chlorophenyl)amino)quinazolin-6-yl)-2-methoxypyridin-3-yl)-4-methylpiperazine-1-sulfonamide, MOL-207

To a mixture consisting of 6-(5-amino-6-methoxypyridin-3-yl)-N-(3-chlorophenyl)quinazolin-4-amine (25 mg, 0.07 mmol) in pyridine (0.5 mL) was added 4-methylpiperazine-1-sulfonyl chloride (40 mg, 0.20 mmol). The reaction mixture was stirred at 40° C. overnight, cooled to room temperature and set idle for 44 days. The mixture was filtered, washed with 2 mL of methanol and dried under high vacuum at room temperature to give the title compound (13 mg, 34%) as a solid; MS (ES-API+) m/z 540.1 (M+1), 542.1 (Cl isotope), (ES-API−) m/z 538.0 (M-1), 540.0 (Cl isotope); $^1$H NMR (400 MHz, DMSO-d6 and $D_2O$) δ δ 8.80 (s, 1H), 8.64

(s, 1H), 8.53 (d, J=1.95 Hz, 1H), 8.12-8.20 (m, 1H), 8.10 (d, J=1.95 Hz, 1H), 8.03 (s, 1H), 7.90 (d, J=8.99 Hz, 1H), 7.80 (br d, J=7.82 Hz, 1H), 7.43 (t, J=8.01 Hz, 1H), 7.19 (br d, J=8.21 Hz, 1H), 3.31-3.50 (m, 4H), 3.00 (br t, J=11.14 Hz, 2H), 2.75 (s, 3H), 2.67 (br t, J=12.51 Hz, 2H).

6-(5-amino-6-chloropyridin-3-yl)-N-(3-chloro-4-fluorophenyl)quinazolin-4-amine (11H), MOL-210

A mixture consisting of 6-bromo-N-(3-chlorophenyl)quinazolin-4-amine—HCl (700 mg 1.80 mmol), 2-methoxy-5-(4,4,5,5-tetramethyl-1,3,2-dioxaborolan-2-yl)pyridin-3-amine (467 mg, 1.80 mmol) and 1.4M $K_2CO_3$ (5.1 mL) in 15 mL of 1,4-dioxane was degassed (vacuum/nitrogen, 3 times). To the reaction mixture was added SiliCat DPP-Pd (300 mg, 0.26 mmol/g loading). The reaction mixture was sealed and heated at 100° C. for 10 minutes in a Biotage Emrys Optimizer microwave. The reaction mixture was cooled, the aqueous phase removed and the remaining organic phase was filtered through a glass frit. The solids were washed with methanol. The filtrate was concentrated under reduced pressure. The residue was dissolved in a mix of ethyl acetate, methanol, dichloromethane, and heptane and was applied to a 120 g silica column and it was eluted with a gradient of 35:65 to 75:25 ethyl acetate-heptane to give 399 mg (55%) of the title compound as a solid; MS (ES-API+) m/z 400.0 (M+1), 402.0 (Cl isotope), (ES-API−) m/z 397.9 (M-1), 400.0 (Cl isotope); $^1$H NMR (400 MHz, DMSO-d6) δ 10.02 (s, 1H), 8.78 (s, 1H), 8.64 (s, 1H), 8.18 (dd, J=2.61, 6.91 Hz, 1H), 8.04-8.12 (m, 2H), 7.88 (d, J=8.69 Hz, 1H), 7.80-7.86 (m, 1H), 7.50 (d, J=2.20 Hz, 1H), 7.41-7.48 (t, 1H), 5.74 (s, 2H).

N-(2-chloro-5-(4-((3-chloro-4-fluorophenyl)amino)quinazolin-6-yl)pyridin-3-yl)methanesulfonamide, MOL-211

To a stirring room temperature mixture consisting of 6-(5-amino-6-chloropyridin-3-yl)-N-(3-chloro-4-fluorophenyl)quinazolin-4-amine (300 mg, 0.75 mmol) in 3 mL of pyridine was added two portions of methanesulfonyl chloride (92 mg, 0.6 mmol (2×)) 4 hours apart. The reaction mixture was then stirred overnight. To the reaction mixture was added 2N NaOH (1.0 mL, 2 mmol) and it was stirred for 30 minutes. The reaction mixture was diluted with a saturated solution of ammonium chloride and 1 mL of 1N HCl (pH=9). The mixture was extracted with ethyl acetate. The organic phase was washed with a saturated solution of ammonium chloride then brine, dried over magnesium sulfate, filtered, and concentrated. The solid residue was chromatographed on an 80 g column of silica eluted with a gradient of 7:3 ethyl acetate-heptane to 100% ethyl acetate. The solid material obtained from the proper fractions was triturated under ethyl acetate (4 mL) and methanol (2 mL), filtered, and dried in high vacuum to give 167 mg (46%, purity 95%) of the title compound; MS (ES-API+) m/z 478.0 (M+1), 480.0 (Cl isotope), (ES-API−) m/z 476.0 (M-1), 478.0 (Cl isotope); $^1$H NMR (400 MHz, DMSO-d6) δ 10.05 (br s, 1H), 9.96 (br s, 1H), 8.88 (s, 1H), 8.80 (d, J=2.10 Hz, 1H), 8.67 (s, 1H), 8.28 (d, J=2.10 Hz, 1H), 8.22-8.27 (m, 1H), 8.18 (dd, J=2.38, 6.86 Hz, 1H), 7.93 (d, J=8.69 Hz, 1H), 7.77-7.89 (m, 1H), 7.49 (t, J=9.06 Hz, 1H), 3.19 (s, 3H).

6-(3-amino-4-chlorophenyl)-N-(3-chloro-4-fluorophenyl)quinazolin-4-amine (11J), MOL-212

A mixture consisting of 6-bromo-N-(3-chlorophenyl)quinazolin-4-amine—HCl (350 mg 0.90 mmol), 2-chloro-5-(4,4,5,5-tetramethyl-1,3,2-dioxaborolan-2-yl)aniline (251 mg, 0.99 mmol) and 1.4M $K_2CO_3$ (2.8 mL) in 10 mL of 1,4-dioxane was degassed (vacuum/nitrogen, 3 times). To the reaction mixture was added SiliCat DPP-Pd (150 mg, 0.26 mmol/g loading). The reaction mixture was sealed and heated at 100° C. for 12 minutes in a Biotage Emrys Optimizer microwave. To the reaction mixture was added additional 2-chloro-5-(4,4,5,5-tetramethyl-1,3,2-dioxaborolan-2-yl)aniline (40 mg, 0.16 mmol) and SiliCat DPP-Pd (30 mg). The reaction mixture was heated again at 100° C. for 6 minutes and cooled. The aqueous phase was removed and the remaining organic phase was filtered through a glass frit. The solids were washed with methanol. The filtrate was concentrated under reduced pressure. The residue was applied to a 120 g silica column and eluted with a gradient of 35:65 to 75:25 ethyl acetate-heptane to give 126 mg (35%) of the title compound as a colorless solid; MS (ES-API+) m/z 399.0 (M+1), 401.0 (Cl isotope), (ES-API−) m/z 397.0 (M-1), 399.0 (Cl isotope); $^1$H NMR (400 MHz, DMSO-d6) δ 10.04 (s, 1H), 8.73 (d, J=1.74 Hz, 1H), 8.64 (s, 1H), 8.20 (dd, J=2.65, 6.86 Hz, 1H), 8.06 (dd, J=1.83, 8.69 Hz, 1H), 7.83-7.90 (m, 2H), 7.47 (t, J=9.10 Hz, 1H), 7.37 (d, J=8.23 Hz, 1H), 7.23 (d, J=2.20 Hz, 1H), 7.03 (dd, J=2.20, 8.23 Hz, 1H), 5.51 (s, 2H).

N-(2-chloro-5-(4-((3-chloro-4-fluorophenyl)amino)quinazolin-6-yl)phenyl)methanesulfonamide, MOL-213

To a stirring room temperature mixture consisting of 6-(3-amino-4-chlorophenyl)-N-(3-chloro-4-fluorophenyl)quinazolin-4-amine (126 mg, 0.32 mmol) in 1.5 mL of pyridine was added methanesulfonyl chloride (45 mg, 0.39 mmol). The reaction mixture was then stirred overnight. To the reaction mixture was added 2N NaOH (1.0 mL, 2 mmol) and it was stirred for 10 minutes. The reaction mixture was diluted with a saturated solution of ammonium chloride and 0.5 mL of 1N HCl. The mixture was extracted with ethyl acetate. The organic phase was washed with a saturated solution of ammonium chloride then brine, dried over magnesium sulfate, filtered, and concentrated. The solid residue was triturated under ethyl acetate (4 mL) and methanol (2 mL) for 20 hours, filtered, and dried in high vacuum to give 83 mg (54%, purity 97%) of the title compound; MS (ES-API+) m/z 477.0 (M+1), 479.0 (Cl isotope), (ES-API−) m/z 474.9 (M-1), 477.0 (Cl isotope); $^1$H NMR (400 MHz, DMSO-d6) δ 10.05 (s, 1H), 9.67 (s, 1H), 8.79 (d, J=1.56 Hz, 1H), 8.64 (s, 1H), 8.12-8.19 (m, 2H), 7.84-7.92 (m, 2H), 7.81 (ddd, J=2.74, 4.30, 9.06 Hz, 1H), 7.73-7.78 (m, 1H), 7.68-7.73 (m, 1H), 7.46 (t, J=9.10 Hz, 1H), 3.10 (s, 3H).

6-bromo-N-(3-chloro-4-(pyridin-2-ylmethoxy)phenyl)quinazolin-4-amine hydrochloride A mixture consisting of 6-bromo-4-chloroquinazoline (1.0 g, 4.1 mmol) and 3-chloro-4-(pyridin-2-ylmethoxy)aniline (1.15 g, 4.9 mmol) in 40 mL of 1,4-dioxane was heated at 80° C. overnight. The reaction mixture was cooled to room temperature, diluted with 20 mL of diethyl ether and filtered. The solids were dried in high vacuum to give 1.98 g (100%, purity 90%) of the title compound; MS (ES-API+) m/z 441.0 (M+1) 443.0 (Cl/Br isotope), (ES-API−) m/z 439.0 (M-1) 441.0 (Cl/Br isotope); $^1$H NMR (400 MHz, DMSO-d6) δ 11.49 (br s, 1H), 9.15 (d, J=1.92 Hz, 1H), 8.91 (s, 1H), 8.61 (d, J=5.03 Hz, 1H), 8.20 (dd, J=2.01, 8.87 Hz, 1H), 7.90-7.96 (m, 2H), 7.87 (d, J=8.97 Hz, 1H), 7.59-7.69 (m, 2H), 7.41 (dd, J=4.99, 6.54 Hz, 1H), 7.34 (d, J=9.06 Hz, 1H), 5.34 (s, 2H).

6-(5-amino-6-chloropyridin-3-yl)-N-(3-chloro-4-(pyridin-2-ylmethoxy)phenyl)quinazolin-4-amine A mixture consisting of 6-bromo-N-(3-chloro-4-(pyridin-2-ylmethoxy)phenyl)quinazolin-4-amine—HCl (900 mg, 1.88 mmol), 2-methoxy-5-(4,4,5,5-tetramethyl-1,3,2-dioxaborolan-2-yl)pyridin-3-amine (832 mg, 4.3 mmol) and 2.0M $K_2CO_3$ (4.4 mL) in 15 mL of 1,4-dioxane was degassed (vacuum/nitrogen, 3 times). To the reaction mixture was added SiliCat DPP-Pd (450 mg, 0.26 mmol/g loading). The reaction mixture was sealed and heated at 100° C. for 20 minutes in a Biotage Emrys Optimizer microwave. The reaction mixture was cooled, the aqueous phase was removed, and the mixture was filtered through a glass frit. The solids were washed with methanol then hot methanol. The filtrate was concentrated under reduced pressure. The residue was diluted with methanol and ethyl acetate, concentrated under reduced pressure to give a solid. The solid was suspended in 20 mL of ethyl acetate. The addition of 2 mL of methanol resulted in a homogeneous solution. The slow addition of 15 mL of heptane resulted in precipitation of a solid and the suspension was stirred for 30 minutes and filtered and dried to give 530 mg of the title compound as a light green/brown solid. The mother liquor was set overnight and produced a precipitate that was filtered to give 300 mg of additional pale green solid. Total: 880 mg (96%, purity 90%); MS (ES-API+) m/z 489.1 (M+1), 491.0 (Cl isotope), (ES-API−) m/z 487.0 (M-1), 489.0 (Cl isotope); $^1$H NMR (400 MHz, DMSO-$d_6$) δ 9.84-10.20 (br s, 1H), 8.79 (br s, 1H), 8.58 (br d, J=4.39 Hz, 1H), 8.50 (br s, 1H), 8.07 (br d, J=1.65 Hz, 1H), 7.95-8.04 (m, 2H), 7.82-7.90 (m, 1H), 7.78 (br d, J=8.88 Hz, 1H), 7.69 (br d, J=7.69 Hz, 1H), 7.53-7.60 (m, 2H), 7.30-7.38 (m, 1H), 7.24 (br d, J=8.78 Hz, 1H), 5.73 (s, 2H), 5.27 (s, 2H).

N-(2-chloro-5-(4-((3-chloro-4-(pyridin-2-ylmethoxy)phenyl)amino)quinazolin-6-yl)pyridin-3-yl)methanesulfonamide, MOL-215

To a stirring room temperature mixture consisting of 6-(5-amino-6-chloropyridin-3-yl)-N-(3-chloro-4-(pyridin-2-ylmethoxy)phenyl)quinazolin-4-amine (300 mg, 0.61 mmol) in 3.5 mL of pyridine was added two portions of methanesulfonyl chloride (140 mg, 2.45 mmol (2×)) 2 hours apart. The reaction mixture was stirred overnight. To the reaction mixture was added 2N NaOH (1.5 mL, 3 mmol). At 0.5 hour an additional amount of 2N NaOH (0.5 mL, 1 mmol) was added and stirring was continued for another 0.5 hour. To the reaction was added 2N NaOH (2.0 mL, 4 mmol) and after 30 minutes the reaction (hydrolysis) appeared to be complete by TLC. The reaction mixture was diluted with a saturated solution of sodium bicarbonate and ethyl acetate and shaken in a separatory funnel. To the mixture was added water, brine, methanol and isopropanol (25 mL) to brake the emulsion. The mixture was extracted twice with ethyl acetate. The combined organic phase was washed with brine, dried over magnesium sulfate, filtered, and concentrated under reduced pressure. The residue was taken up in toluene and concentrated. The solid was taken up in methanol/ethyl acetate, filtered and the filtrate was applied to a 120 g silica column eluted with 9:1 ethyl acetate-heptane to 100% ethyl acetate to 1:9 methanol-ethyl acetate to give 140 mg (40%, purity 97%) of the title compound as a yellow solid; MS (ES-API+) m/z 567.0 (M+1), 569.1 (Cl isotope), (ES-API−) m/z 565.0 (M-1), 567.0 (Cl isotope); $^1$H NMR (400 MHz, DMSO-$d_6$) δ 9.96 (br s, 2H), 8.88 (s, 1H), 8.81 (d, J=2.10 Hz, 1H), 8.62 (s, 1H), 8.60 (br d, J=4.39 Hz, 1H), 8.29 (d, J=2.01 Hz, 1H), 8.24 (br d, J=8.78 Hz, 1H), 8.02 (d, J=2.47 Hz, 1H), 7.86-7.93 (m, 2H), 7.72 (dd, J=2.38, 8.87 Hz, 1H), 7.59 (d, J=7.87 Hz, 1H), 7.34-7.41 (m, 1H), 7.31 (d, J=9.06 Hz, 1H), 5.31 (s, 2H), 3.20 (s, 3H).

6-(5-aminopyridin-3-yl)-N-(3-chlorophenyl)quinazolin-4-amine, MOL-310

A mixture consisting of 6-bromo-N-(3-chlorophenyl)quinazolin-4-amine—HCl (500 mg 1.49 mmol), 5-(4,4,5,5-tetramethyl-1,3,2-dioxaborolan-2-yl)pyridin-3-amine (274 mg, 1.24 mmol) and 2.0M $K_2CO_3$ (3.1 mL) in 15 mL of 1,4-dioxane was degassed (vacuum/nitrogen, 3 times). To the reaction mixture was added SiliCat DPP-Pd (60 mg, 0.26 mmol/g loading). The reaction mixture was sealed and heated at 95° C. for 1.25 hours. To the reaction was added 5-(4,4,5,5-tetramethyl-1,3,2-dioxaborolan-2-yl)pyridin-3-amine (90 mg, 0.41 mmol) and heated again at 95° C. overnight. The reaction mixture was cooled and filtered through a glass frit. The solids were washed with ethanol. The filtrate was concentrated under reduced pressure. The residue was chromatographed on a 40 g silica column using the dry loading method and eluted with a gradient of 1:99 to 15:85 methanol-ethyl acetate to give 126 mg (24%, purity 97.4%) of the title compound; MS (ES-API+) m/z 348.0 (M+1), 350.0 (Cl isotope), (ES-API−) m/z 346.0 (M-1), 348.0 (Cl isotope); $^1$H NMR (400 MHz, DMSO-$d_6$) δ 9.99 (s, 1H), 8.81 (d, J=1.65 Hz, 1H), 8.66 (s, 1H), 8.24 (d, J=1.92 Hz, 1H), 8.05-8.14 (m, 2H), 7.99 (d, J=2.47 Hz, 1H), 7.81-7.93 (m, 2H), 7.42 (t, J=8.10 Hz, 1H), 7.29 (t, J=2.29 Hz, 1H), 7.18 (d, J=8.18 Hz, 1H), 5.48 (s, 2H).

6-(5-(1H-tetrazol-1-yl)pyridin-3-yl)-N-(3-chlorophenyl)quinazolin-4-amine, MOL-311

To a mixture consisting of 6-(5-aminopyridin-3-yl)-N-(3-chlorophenyl)quinazolin-4-amine (100 mg, 0.29 mmol) in 2 mL of acetic acid was added trimethylorthoformate (92 mg, 0.86 mmol) and sodium azide (56 mg, 0.86 mmol). The reaction mixture was heated at 80° C. for 4 hours. The reaction was quenched with a saturated solution of sodium bicarbonate and extracted with ethyl acetate. The organic phase was dried over magnesium sulfate, filtered, and concentrated under reduce pressure to a yellow solid. The solid was triturated under 4:1 dichloromethan-ethyl acetate followed by trituration under dichloromethane-ethyl acetate-tetrahydrofuran and filtered to give 40 mg (34, purity 91%) of the title compound; MS (ES-API+) m/z 401.1 (M+1), 403.0 (Cl isotope), (ES-API−) m/z 399.0 (M-1), 401.0 (Cl isotope); $^1$H NMR (400 MHz, DMSO-$d_6$) δ 10.26 (s, 1H), 10.00 (s, 1H), 9.33 (s, 1H), 9.19 (d, J=2.10 Hz, 1H), 9.01 (s, 1H), 8.76-8.88 (m, 1H), 8.69 (s, 1H), 8.38 (d, J=8.60 Hz, 1H), 8.08 (s, 1H), 7.95 (d, J=8.60 Hz, 1H), 7.84 (br d, J=8.23 Hz, 1H), 7.44 (t, J=8.10 Hz, 1H), 7.20 (d, J=7.96 Hz, 1H).

5-(4-((3-chlorophenyl)amino)quinazolin-6-yl)nicotinonitrile, MOL-312

A mixture consisting of 6-bromo-N-(3-chlorophenyl)quinazolin-4-amine—HCl (500 mg 1.49 mmol), 5-(4,4,5,5-tetramethyl-1,3,2-dioxaborolan-2-yl)nicotinonitrile (286 mg, 1.24 mmol) and 2.0M $K_2CO_3$ (3.1 mL) in 15 mL of 1,4-dioxane was degassed (vacuum/nitrogen, 3 times). To the reaction mixture was added SiliCat DPP-Pd (70 mg, 0.26 mmol/g loading). The reaction mixture was sealed and heated at 95° C. for 4 hous. The reaction mixture was cooled and filtered through a glass frit. The solids were washed with ethanol. The filtrate was concentrated under reduced pressure. Toluene was added to the residue and concentrated under reduced pressure. The residue was chromatographed on a 40 g silica column using the dry loading method and eluted with a gradient of 25:75 to 95:5 ethyl acetate-dichloromethane followed by the addition of 5% methanol up to 9% methanol in the 95:5 ethyl acetate-dichloromethane system to give 147 mg (33%) of the title compound as a pale yellow solid; MS (ES-API+) m/z 358.0 (M+1), 360.0 (Cl isotope), (ES-API−) m/z 356.0 (M−1), 358.0 (Cl isotope); $^1$H NMR (400 MHz, DMSO-d6) δ 9.95 (s, 1H), 9.41 (d, J=2.20 Hz, 1H), 9.08 (d, J=1.83 Hz, 1H), 8.94 (d, J=1.74 Hz, 1H), 8.82 (t, J=2.10 Hz, 1H), 8.69 (s, 1H), 8.34 (dd, J=1.83, 8.69 Hz, 1H), 8.07 (t, J=1.97 Hz, 1H), 7.92 (d, J=8.69 Hz, 1H), 7.84 (dd, J=1.19, 8.23 Hz, 1H), 7.44 (t, J=8.14 Hz, 1H), 7.20 (dd, J=1.33, 7.91 Hz, 1H).

6-(5-(1H-tetrazol-5-yl)pyridin-3-yl)-N-(3-chlorophenyl)quinazolin-4-amine, MOL-313

A mixture consisting of 5-(4-((3-chlorophenyl)amino) quinazolin-6-yl)nicotinonitrile (50 mg, 0.14 mmol), sodium azide (18 mg, 0.28 mmol), ammonium chloride (15 mg, 0.28 mmol) and lithium chloride (1.2 mg) was heated at 100° C. overnight. The reaction was cooled, toluene was added and the mixture was concentrated under reduced pressure to less than 1 mL. To the residue was added a mixture of 0.5:5:95 acetic acid-methanol-dichloromethane and the mixture was filtered. The filtrate was applied to a 25 g silica column which was eluted with a gradient of 0.5:10:90 to 0.5:40:60 acetic acid-methanol-dichloromethane to give 34 mg (60%, purity 96%) of the title compound as a solid; MS (ES-API+) m/z 401.0 (M+1), 403.1 (Cl isotope); $^1$H NMR (400 MHz, DMSO-d$_6$) δ 10.25 (br s, 1H), 9.18 (s, 1H), 9.03 (s, 1H), 9.01 (s, 1H), 8.71 (s, 1H), 8.67 (s, 1H), 8.29 (d, J=8.69 Hz, 1H), 8.13 (s, 1H), 7.92 (d, J=8.69 Hz, 1H), 7.88 (br d, J=8.42 Hz, 1H), 7.42 (t, J=8.10 Hz, 1H), 7.18 (d, J=7.96 Hz, 1H).

Example 9

This example shows the synthesis procedure for additional quinoline based compounds of the present invention.

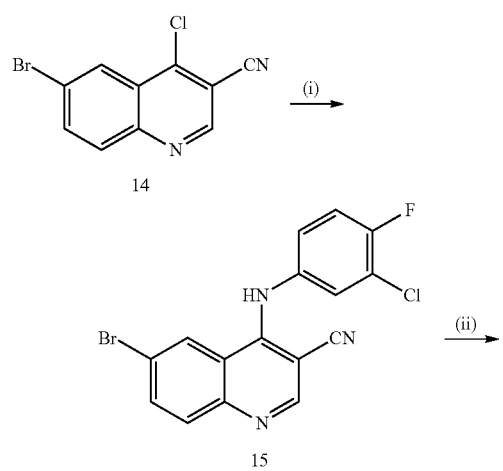

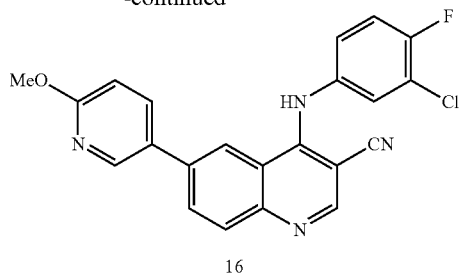

Reaction conditions: (i) 2A, dioxane, 90° C., 2 hr. (ii) 9G, dioxane, Cs$_2$CO$_3$, PdCl$_2$(dppf), 80° C., 2 hour 4-((3-chloro-4-fluorophenyl)amino)-6-(6-methoxypyridin-3-yl)quinoline-3-carbonitrile, MOL-150

A mixture of 6-bromo-4-chloroquinoline-3-carbonitrile (14, 200 mg, 0.75 mmol) and 3-chloro-4-fluoroaniline (2A, 130 mg, 0.90 mmol) in 4 mL of 1,4-dioxane was heated at 90° C. for 2 hour. The reaction mixture was cooled to room temperature, diluted with diethyl ether, cooled to 0° C. and filtered through fritted glass. The solid was washed with diethyl ether and dried to give 6-bromo-4-((3-chloro-4-fluorophenyl)amino)quinoline-3-carbonitrile (15, 280 mg, 100%) as a dull yellow solid. A solution of 6-bromo-4-((3-chloro-4-fluorophenyl)amino)quinoline-3-carbonitrile (278 mg, 0.77 mmol) and (6-methoxypyridin-3-yl)boronic acid (9G, 118 mg, 0.77 mmol) in 1,4-dioxane (15 mL) and water (1.4 mL) was degassed. To the solution was added cesium carbonate (1.0 g, 3.1 mmol) and [1,1'-his(diphenylphosphino)ferrocene]dichloropalladium(II) (44 mg). The reaction mixture was heated at 80° C. under N$_2$ for 2 hours. The reaction mixture was diluted with toluene and the volatiles were removed under vacuum and the crude material was purified by silica gel column chromatography eluting with a gradient of 3/7 to 7/3 ethyl acetate/heptane. The yellow solid was triturated under dichloromethane/diethyl ether, filtered and dried to give 4-((3-chloro-4-fluorophenyl)amino)-6-(6-methoxypyridin-3-yl)quinoline-3-carbonitrile (16, MOL-150, 44 mg, 14%, 100% purity) as a white solid; $^1$H NMR (400 MHz, DMSO-d$_6$) δ 9.95 (s, 1H), 8.75 (d, J=1.9 Hz, 1H), 8.70 (d, J=1.9 Hz, 1H), 8.58 (s, 1H), 8.21 (t, J=6.2 Hz, 2H), 7.99 (d, J=8.4 Hz, 1H), 7.64 (d, J=6.6 Hz, 1H), 7.48 (t, J=8.8 Hz, 1H), 7.3-7.4 (m, 1H), 6.99 (d, J=8.5 Hz, 1H), 3.91 (s, 3H); MS: (ESI$^+$ m/z 405.1, ESI$^−$ m/z 403.1).

6-bromo-4-((4-(pyridin-4-yloxy)phenyl)amino)quinoline-3-carbonitrile hydrochloride, MOL-400

A mixture consisting of 6-bromo-4-chloroquinoline-3-carbonitrile (440 mg, 1.64 mmol) and 4-(pyridin-4-yloxy) aniline (291 mg, 1.56 mmol) in 3 mL of ethoxyethanol was heated at 125° C. for 2 hours in a sealed vessel. The reaction mixture was cooled to room temperature and filtered to give 193 mg of the title compound as a light brown solid. The filtrate was diluted with ethyl acetate and washed with a saturated solution of sodium bicarbonate. The aqueous phase was extracted two time with ethyl acetate. The combined organic phase was washed with brine, dried over magnesium sulfate, filtered, and concentrated under reduced pressure. The residue was chromatographed on 25 g of silica eluted with a gradient of 45:55 ethyl acetate-heptane to 100% ethyl acetate to 2:98 methanol-ethyl acetate to give 160 mg of the title compound as a tan solid. Total: 353 mg (54%). A sample of the light brown solid was mostly dissolved in 5 mL of 2:8 methanol-dichloromethane and while stirring 15 mL of diethyl ether and 5 mL of heptane were added. The suspension was stirred overnight and filtered. The filtrate was set at room temperature and the crystalline material which formed was filtered to give near white solid (99.9% pure); MS (ES-API+) m/z 417.0 (M+1) 419.0 (Br isotope), (ES-API−) m/z 414.9 (M-1) 417.0 (Br isotope); $^1$H NMR (400 MHz, DMSO-d$_6$) δ 10.03 (br s, 1H), 8.78 (d, J=1.92 Hz, 1H), 8.57 (s, 1H), 8.44-8.51 (m, 2H), 7.97 (dd, J=2.10, 8.87 Hz, 1H), 7.85 (d, J=8.87 Hz, 1H), 7.45 (d, J=8.69 Hz, 2H), 7.21-7.30 (m, 2H), 6.97-7.03 (m, 2H).

6-(3-(hydroxymethyl)phenyl)-4-((4-(pyridin-4-yloxy)phenyl)amino)quinoline-3-carbonitrile, MOL-402

A mixture consisting of 6-bromo-4-((4-(pyridin-4-yloxy)phenyl)amino)quinoline-3-carbonitrile hydrochloride (40 mg 0.096 mmol), (3-(hydroxymethyl)phenyl)boronic acid (19 mg, 0.125 mmol) and 2.0M K$_2$CO$_3$ (0.24 mL) in 2 mL of 1,4-dioxane and 1 mL of ethanol was degassed (vacuum/nitrogen, 3 times). To the reaction mixture was added SiliCat DPP-Pd (25 mg, 0.26 mmol/g loading). The reaction mixture was sealed and heated at 95° C. for 2 hours. The reaction mixture was cooled and filtered through a glass frit. The solids were washed with ethanol. The filtrate was concentrated under reduced pressure. The residue was triturated under 1.5 mL of methanol and filtered to give 25 mg (58%, purity 98.4%) of the title compound as a solid; MS (ES-API+) m/z 445.2 (M+1), (ES-API−) m/z 443.2 (M-1); $^1$H NMR (400 MHz, DMSO-d$_6$) δ 10.11 (br s, 1H), 8.75-8.88 (m, 1H), 8.54 (s, 1H), 8.44 (d, J=5.37 Hz, 2H), 8.17 (dd, J=1.69, 8.65 Hz, 1H), 7.99 (d, J=8.60 Hz, 1H), 7.83 (s, 1H), 7.76 (br d, J=7.96 Hz, 1H), 7.43-7.54 (m, 3H), 7.38 (d, J=7.50 Hz, 1H), 7.26 (d, J=8.78 Hz, 2H), 6.93-7.02 (m, 2H), 5.28 (t, J=5.67 Hz, 1H), 4.60 (d, J=5.58 Hz, 2H).

N-(5-(3-cyano-4-((4-(pyridin-4-yloxy)phenyl)amino)quinolin-6-yl)pyridin-3-yl)methanesulfonamide, MOL-401

A mixture consisting of 6-bromo-4-((4-(pyridin-4-yloxy)phenyl)amino)quinoline-3-carbonitrile hydrochloride (80 mg 0.19 mmol), N-(5-(4,4,5,5-tetramethyl-1,3,2-dioxaborolan-2-yl)pyridin-3-yl)methanesulfonamide (74 mg, 0.25 mmol) and 2.0M K$_2$CO$_3$ (0.47 mL) in 4 mL of 1,4-dioxane and 2 mL of ethanol was degassed (vacuum/nitrogen, 3 times). To the reaction mixture was added SiliCat DPP-Pd (50 mg, 0.26 mmol/g loading). The reaction mixture was sealed and heated at 95° C. for 2 hours. The reaction mixture was cooled and filtered through a glass frit. The solids were washed with ethanol. The filtrate was concentrated under reduced pressure. The residue was chromatographed on a 12 g silica column eluted with a gradient of 100% ethyl acetate to 25:75 methanol-ethyl acetate to give 65 mg of a yellow solid. The solid was triturated under a mix of methanol-ethyl acetate-dichloromethane and filtered to give 32 mg of the title compound as a yellow solid (33%, purity 91%); MS (ES-API+) m/z 509.1 (M+1), (ES-API−) m/z 507.0 (M-1); $^1$H NMR (400 MHz, DMSO-d6) δ 10.14 (s, 2H), 8.86 (s, 2H), 8.58 (s, 1H), 8.44-8.51 (m, 2H), 8.13-8.22 (m, 1H), 8.13-8.22 (m, 1H), 8.05 (br d, J=8.60 Hz, 1H), 8.00 (t, J=2.10 Hz, 1H), 7.49 (br d, J=8.33 Hz, 2H), 7.27 (d, J=8.69 Hz, 2H), 6.98 (d, J=5.37 Hz, 2H), 3.13 (s, 3H).

6-(3-hydroxyphenyl)-4-((4-(pyridin-4-yloxy)phenyl)amino)quinoline-3-carbonitrile, MOL-403

A mixture consisting of 6-bromo-4-((4-(pyridin-4-yloxy)phenyl)amino)quinoline-3-carbonitrile hydrochloride (80 mg 0.19 mmol), (3-hydroxyphenyl)boronic acid (34 mg, 0.25 mmol) and 2.0M K$_2$CO$_3$ (0.47 mL) in 4 mL of 1,4-dioxane and 2 mL of ethanol was degassed (vacuum/nitrogen, 3 times). To the reaction mixture was added SiliCat DPP-Pd (50 mg, 0.26 mmol/g loading). The reaction mixture was sealed and heated at 95° C. for 2 hours. The reaction mixture was cooled and filtered through a glass frit. The solids were washed with ethanol. The filtrate was diluted with toluene and concentrated under reduced pressure. The residue was chromatographed on a 12 g silica column eluted with a gradient of 8:2 ethyl acetate-dichloromethane to 100% ethyl acetate then to 1:9 methanol-ethyl acetate to give 15 mg (18%, purity 95.9%) of the title compound; MS (ES-API+) m/z 431.1 (M+1), (ES-API−) m/z 429.1 (M-1); $^1$H NMR (400 MHz, DMSO-d$_6$) δ 9.91-10.48 (br s, 1H), 9.47-9.91 (br s, 1H), 8.75 (s, 1H), 8.38-8.52 (m, 3H), 8.07 (br d, J=7.96 Hz, 1H), 7.92 (br d, J=8.69 Hz, 1H), 7.41 (br d, J=8.05 Hz, 2H), 7.25-7.36 (m, 3H), 7.22 (br d, J=8.60 Hz, 2H), 6.96 (d, J=6.13 Hz, 2H), 6.82 (br d, J=7.23 Hz, 1H).

6-bromo-4-((3-chloro-4-fluorophenyl)amino)quinoline-3-carbonitrile hydrochloride A mixture consisting of 6-bromo-4-chloroquinoline-3-carbonitrile (1.0 g, 3.7 mmol) and 3-chloro-4-fluoroaniline (653 mg, 4.5 mmol) in 40 mL of 1,4-dioxane was heated at 80° C. overnight. The reaction mixture was cooled to room temperature, diluted with 20 mL of diethyl ether and filtered. The solids were dried in high vacuum to give 1.36 g (89%) of the title compound; MS (ES-API+) m/z 376.0 (M+1) 378.0 (Cl/Br isotope), (ES-API−) m/z 373.9 (M-1) 375.9 (Cl/Br isotope); $^1$H NMR (400 MHz, DMSO-d$_6$) δ 9.07 (d, J=1.83 Hz, 1H), 8.99 (s, 1H), 8.16 (dd, J=1.92, 8.97 Hz, 1H), 8.00 (d, J=8.88 Hz, 1H), 7.75 (dd, J=2.52, 6.63 Hz, 1H), 7.50-7.59 (m, 1H), 7.43-7.50 (m, 1H).

6-(5-amino-6-chloropyridin-3-yl)-4-((3-chloro-4-fluorophenyl)amino)quinoline-3-carbonitrile A mixture consisting of 6-bromo-4-((3-chloro-4-fluorophenyl)amino)quinoline-3-carbonitrile—HCl (1.2 g, 2.9 mmol), 2-methoxy-5-(4,4,5,5-tetramethyl-1,3,2-dioxaborolan-2-yl)pyridin-3-amine (1.1 g, 4.3 mmol) and 2.0M K$_2$CO$_3$ (5.8 mL) in 15 mL of 1,4-dioxane was degassed (vacuum/nitrogen, 3 times). To the reaction mixture was added SiliCat DPP-Pd (650 mg, 0.26 mmol/g loading). The reaction mixture was sealed and heated at 100° C. for 20 minutes in a Biotage Emrys Optimizer microwave. The reaction mixture was cooled and filtered through a glass frit. The solids were washed with methanol then hot methanol. The filtrate was concentrated under reduced pressure. The residue was diluted with toluene, concentrated under reduced pressure then triturated under ethyl acetate for one hour. The solid was filtered and dried to give 2.98 g of the title compound as a solid; MS (ES-API+) m/z 424.0 (M+1), 426.0 (Cl isotope), (ES-API−) m/z 422.0 (M-1), 423.9 (Cl isotope); $^1$H NMR (400 MHz, DMSO-d$_6$) δ 8.52 (s, 1H), 7.88 (d, J=2.01 Hz, 1H), 7.78 (s, 1H), 7.62-7.68 (m, 1H), 7.38-7.50 (m, 2H), 7.08 (t, J=9.24 Hz, 1H), 6.77 (br d, J=6.68 Hz, 1H), 6.60-6.69 (m, 1H), 5.61 (s, 2H).

N-(2-chloro-5-(4-(((3-chloro-4-fluorophenyl)amino)-3-cyanoquinolin-6-yl)pyridin-3-yl)methanesulfonamide, MOL-216

To a stirring room temperature mixture consisting of 6-(5-amino-6-chloropyridin-3-yl)-4-((3-chloro-4-fluorophenyl)amino)quinoline-3-carbonitrile (1.00 g, 2.35 mmol) in 12 mL of pyridine was added two portions of methanesulfonyl chloride (0.54 g, 9.4 mmol (2×)) 2 hours apart. The reaction mixture was stirred a total of 5 hours. To the reaction mixture was added 2N NaOH (5.0 mL, 10 mmol). At 1.5 hours an additional amount of 2N NaOH (3 mL, 6 mmol) was added and stirring was continued for another 0.5 hours. To the dark orange/red reaction mixture was added dropwise 6N HCl (1 mL, 6 mmol). The red/brown reaction mixture was diluted with a saturated solution of sodium chloride and the mixture was extracted twice with ethyl acetate. The combined organic phase was washed with brine, dried over magnesium sulfate, filtered, and concentrated. The solid residue was triturated under a mixture of methanol and ethyl acetate and was filtered. The mother liquor was applied to a 120 g silica column eluted with a gradient of 65:35 ethyl acetate-heptane to 100% ethyl acetate to 15:85 methanol-ethyl acetate. The clean fractions containing product were combined and pale yellow solid was allowed to precipitate. It was filtered and dried to give 30 mg (2.5%) of the title compound. The filtered solid from above was dissolved in hot methanol-ethyl acetate (9:1, 250 mL). To the solution was added 25 g of silica and this mixture was used to dry load the sample on to a 220 g silica column eluted with a gradient of 65:35 ethyl acetate-heptane to 100% ethyl acetate to 1:9 methanol-ethyl acetate. The fractions containing clean product were concentrated under reduced pressure to give 52 mg (4.2%) of the title compound as an off-white solid. MS (ES-API+) m/z 502.0 (M+1), 504.0 (Cl isotope), (ES-API−) m/z 500.0 (M-1), 501.9 (Cl isotope); $^1$H NMR (400 MHz, DMSO-$d_6$) δ 10.06 (s, 1H), 9.93 (br s, 1H), 8.84 (s, 1H), 8.80 (s, 1H), 8.62 (s, 1H), 8.28 (s, 1H), 8.24 (br d, J=9.15 Hz, 1H), 8.05 (br d, J=8.51 Hz, 1H), 7.67 (br d, J=4.67 Hz, 1H), 7.45-7.54 (m, 1H), 7.42 (br s, 1H), 3.16 (s, 3H).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound described by Formula II:

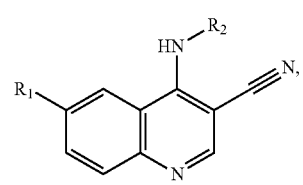

(Formula II)

including pharmaceutically acceptable salts, solvates, and/or prodrugs thereof; wherein R1 is independently selected from:

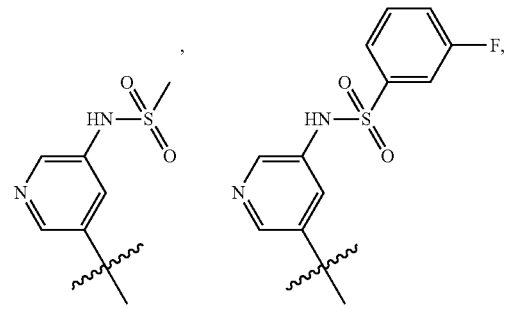

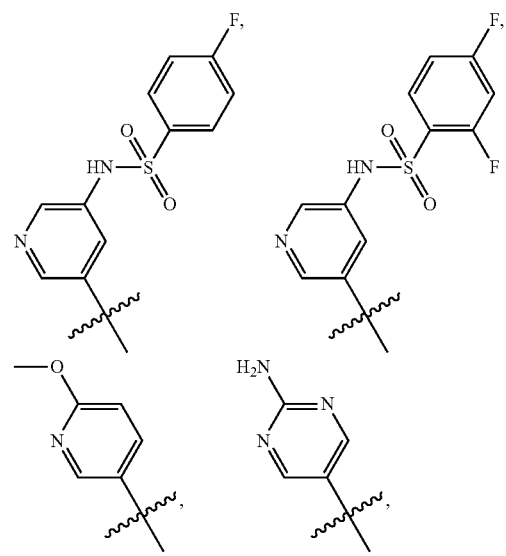

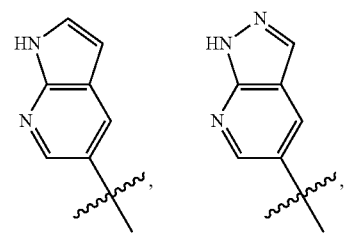

113
-continued
114
-continued
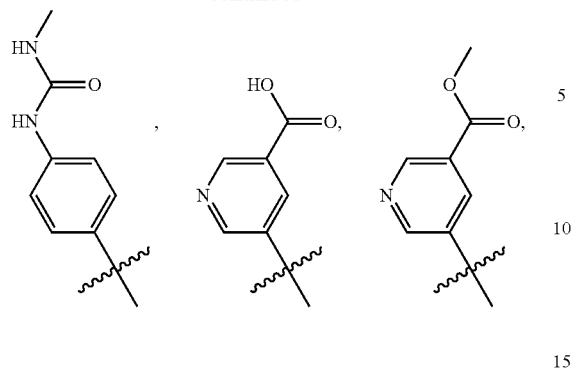
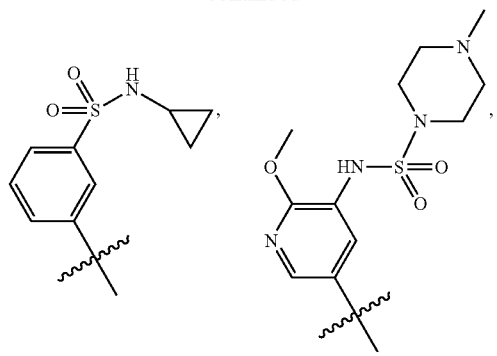
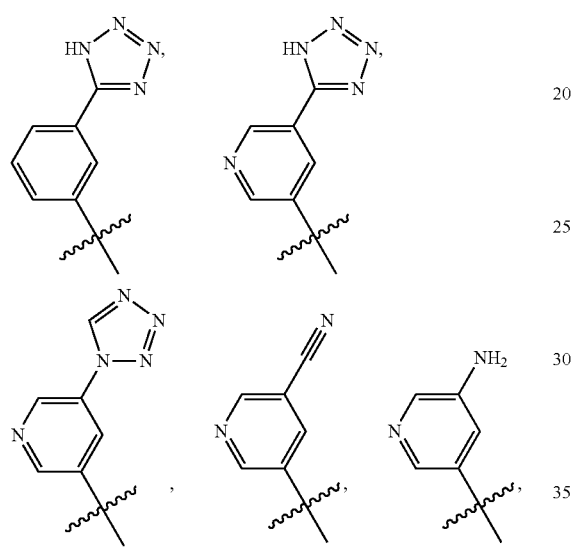
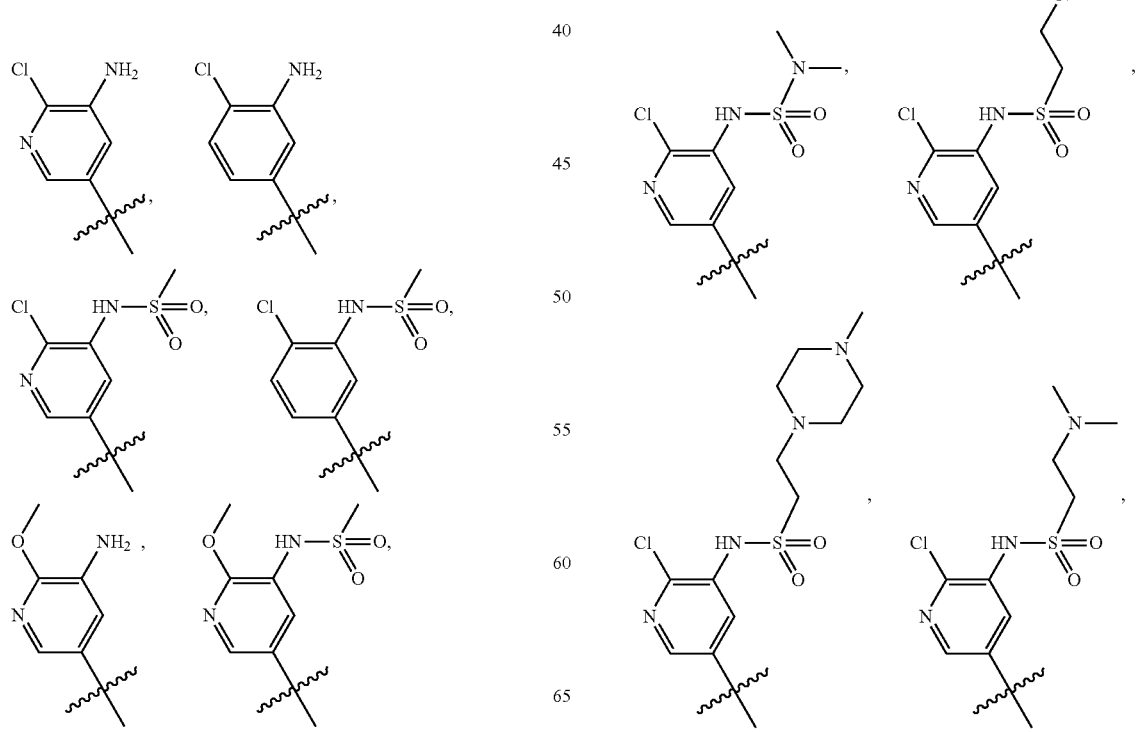

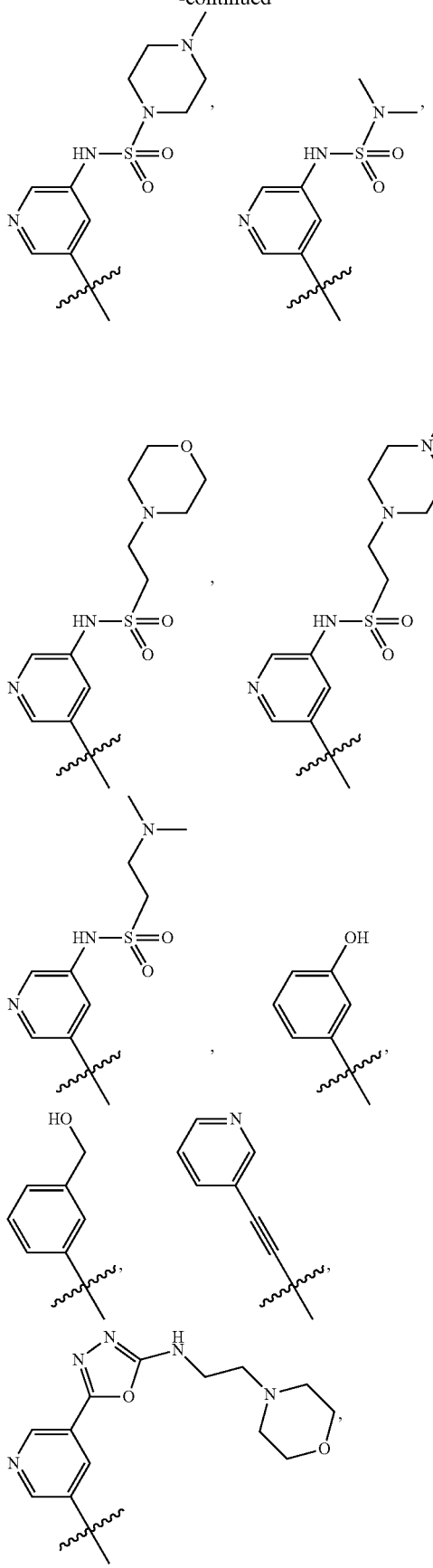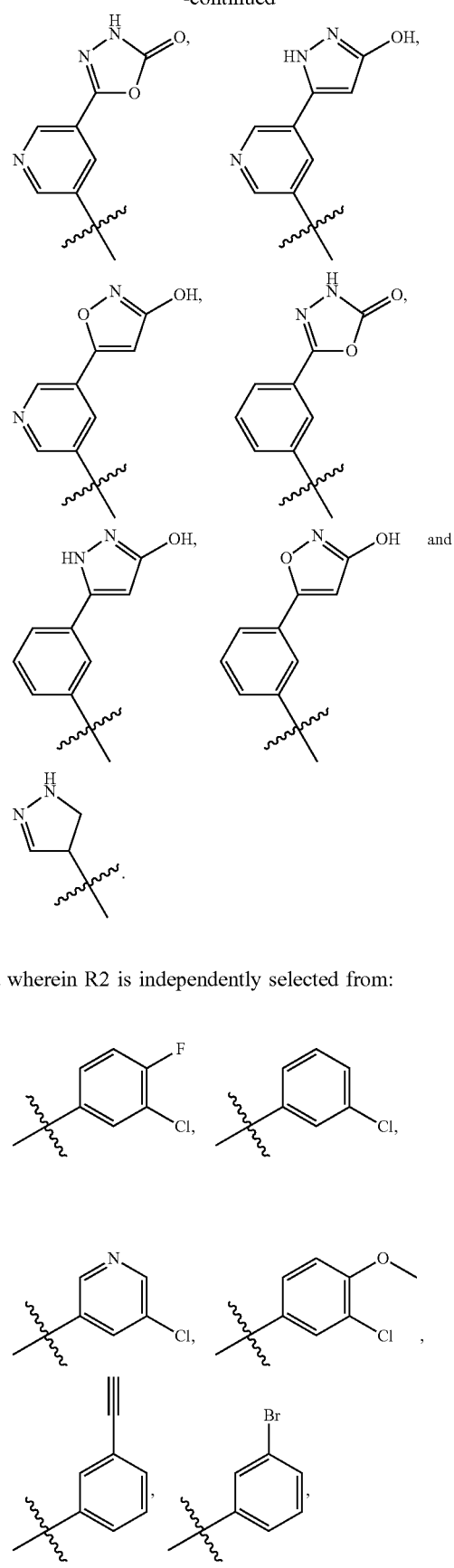
and wherein R2 is independently selected from:

117
-continued
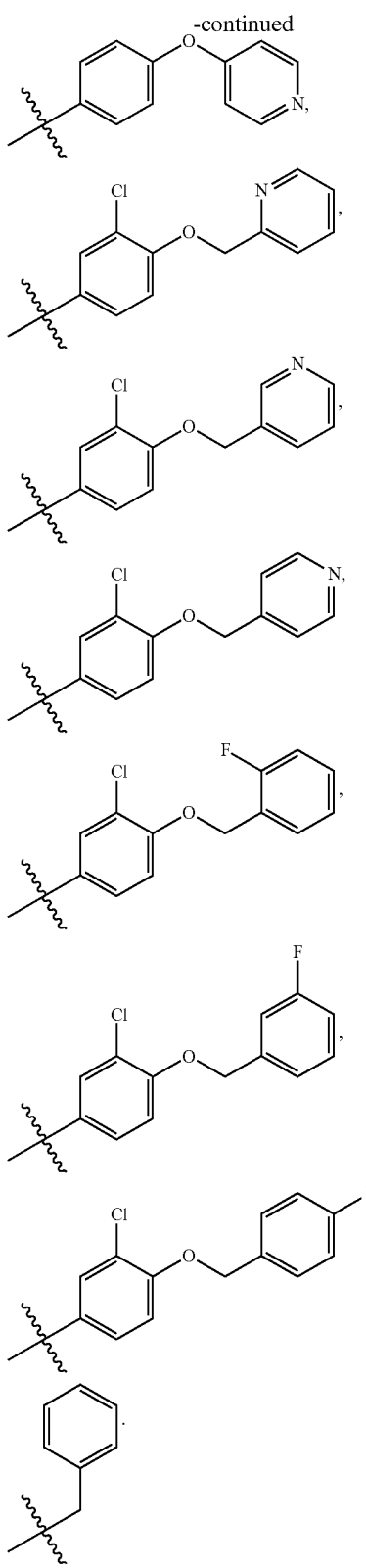
and the resulting compound inhibits an EGFR protein and inhibit a PI3K protein.
2. The compound of claim 1, wherein the EGFR protein is one or more of ERBB1, ERBB2, and ERBB4,
118
wherein the PI3K protein is one or more of PIK3Cα, PIK3δ, PIK3β, PIK3Cγ, and PI3Kα.
3. The compound of claim 1, wherein said compound is selected from the group consisting of
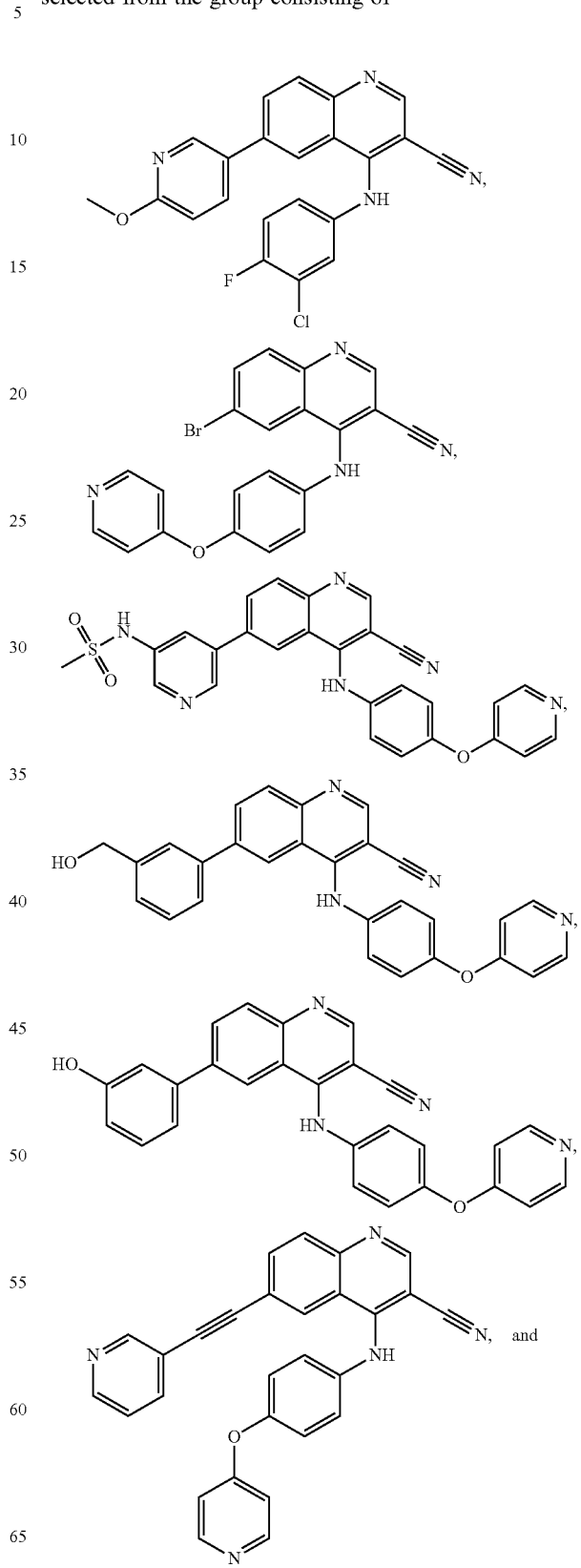

-continued

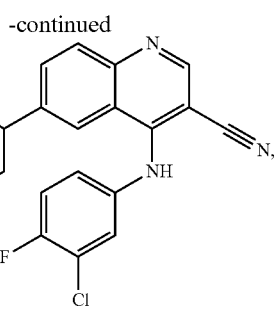

or a pharmaceutically acceptable salt thereof, and a pharmaceutically acceptable carrier.

4. A method of treating, or ameliorating NSCLC, head & neck cancer, glioblastoma multiforme, or colorectal cancer, in a patient in need thereof, comprising administering to said patient a therapeutically effective amount of the compound of claim 1.

5. The method of claim 4, wherein said patient is a human patient.

6. The method of claim 4 further comprising administering to said patient one or more anticancer agents.

7. The method of claim 6, wherein said anticancer agent is a chemotherapeutic agent.

8. The method of claim 6 wherein said anticancer agent is radiation therapy.

9. The method of claim 4, wherein said compound is capable of inhibiting EGFR activity and PI3IK activity.

10. A kit comprising a compound of claim 1 and instructions for administering said compound to a patient having NSCLC, head & neck cancer, glioblastoma multiform, or colorectal cancer.

11. The kit of claim 10 further comprising one or more anticancer agents.

12. The kit of claim 11, wherein said compound is to be administered together with one or more anticancer agents.

* * * * *